US009642361B2

(12) United States Patent
Baroja Fernandez et al.

(10) Patent No.: US 9,642,361 B2
(45) Date of Patent: May 9, 2017

(54) METHOD FOR CHANGING THE DEVELOPMENT PATTERN, INCREASING THE GROWTH AND THE ACCUMULATION OF STARCH, CHANGING THE STRUCTURE OF STARCH AND INCREASING THE RESISTANCE TO WATER STRESS IN PLANTS

(75) Inventors: Miren Edurne Baroja Fernandez, Mutilva (ES); Jun Li, Mutilva (CN); Javier Pozueta Romero, Mutilva (ES); Ignacio Ezquer Garin, Valencia (ES); Abdellatif Bahaji, Mutilva (ES); Francisco Jose Munoz Perez, Mutilva (ES); Miroslav Ovecka, Bratislava (SK)

(73) Assignee: IDEN BIOTECHNOLOGY, S.L., Cordovilla (Navarra) (ES)

( * ) Notice: Subject to any disclaimer, the term of this patent is extended or adjusted under 35 U.S.C. 154(b) by 480 days.

(21) Appl. No.: 13/642,310

(22) PCT Filed: Apr. 15, 2011

(86) PCT No.: PCT/ES2011/000125
§ 371 (c)(1),
(2), (4) Date: Oct. 19, 2012

(87) PCT Pub. No.: WO2011/135121
PCT Pub. Date: Nov. 3, 2011

(65) Prior Publication Data
US 2013/0116124 A1 May 9, 2013

(30) Foreign Application Priority Data

Apr. 19, 2010 (ES) .................................. 201000499
Aug. 13, 2010 (ES) .................................. 201001068
Apr. 7, 2011 (ES) .................................. 201100405

(51) Int. Cl.
*A01N 37/02* (2006.01)
*A01N 63/04* (2006.01)
*A01N 63/02* (2006.01)
*A01N 35/02* (2006.01)
*C05F 11/08* (2006.01)
*A01N 63/00* (2006.01)

(52) U.S. Cl.
CPC ............. *A01N 37/02* (2013.01); *A01N 35/02* (2013.01); *A01N 63/00* (2013.01); *A01N 63/02* (2013.01); *A01N 63/04* (2013.01); *C05F 11/08* (2013.01)

(58) Field of Classification Search
CPC ........ A01N 37/02; A01N 63/04; A01N 63/02; A01N 35/02; A01N 63/00; C05F 11/08
USPC ...................................................... 504/320
See application file for complete search history.

(56) References Cited

U.S. PATENT DOCUMENTS 6,524,998 B1 * 2/2003 Kloepper et al. ............. 504/100

FOREIGN PATENT DOCUMENTS

CN 101167452 4/2008
JP 2004 256508 9/2004

OTHER PUBLICATIONS

Murashige, T. et al., A Revised Medium for Rapid Growth and Bio Assays with Tabacco Tissue Cultures, 1962, Physiologia Plantarum, vol. 15, pp. 473-497.*
Contreras-Cornejo, Trichoderma virens, a Plant Beneficial Fungus, Enhances Biomass Production and Promotes Lateral Root Growth through Auxin-Dependent Mechanism in Arabidopsis, Mar. 2009, Plant Physiology, vol. 149, pp. 1579-1592.*
Supplementary European Search Report issued Mar. 13, 2014, in corresponding European Application No. EP 11774436.7, filed Apr. 15, 2011, 4 pages.
Xitao Xie, et al., "Sustained growth promotion in Arabidopsis with long-term exposure to the beneficial soil bacterium *Bacillus subtilis* (GB03)," Plant Signaling & behavior, vol. 4, Issue 10, Jan. 1, 2009, pp. 948-953.
Francisca M. Gutierrez-Luna, et al., "Plant growth-promoting rhizobacteria modulate root-system architecture in *Arabidopsis thaliana* through volatile organic compound emission," Symbiosis, vol. 51, No. 1, May 23, 2010, pp. 75-83.
Huiming Zhang, et al., "Rhizobacterial volatile emissions regulate auxin homeostasis and cell expansion in Arabidopsis," Planta—AN International Journal of Plant Biology, Springer, Berlin, Germany, vol. 226, No. 4, May 12, 2007, pp. 839-851.
Ryu, C.M., et al., "Bacterial volatiles promote growth in Arabidopsis," PNAS, vol. 100, No. 8, pp. 4927-4932, (Apr. 15, 2003).

(Continued)

*Primary Examiner* — Sue Liu
*Assistant Examiner* — Andriae M Holt
(74) *Attorney, Agent, or Firm* — Oblon, McClelland, Maier & Neustadt, L.L.P.

(57) ABSTRACT

The invention relates to a method for changing the development pattern, increasing the growth and starch accumulation, changing the structure of starch and increasing the resistance to water stress in plants. The method involves culturing plants in an atmosphere containing volatile elements emitted by a microorganism, without there being any physical contact between the microorganism and the plant. The method is based on the discovery that the volatile elements emitted by Gram-positive or Gram-negative bacteria, yeasts and microscopic fungi stimulate an increase in the growth of plants in general, with an increase in the height, the number of leaves and/or the number of branches of the plant, as well as an increase in the accumulated starch and structural change of this biopolymer, and modification of the development pattern, with an increase in floral buds. An increased resistance to water stress can also be observed, in addition to an increase in starch in leaves separated from whole plants.

42 Claims, 45 Drawing Sheets

(56) References Cited

OTHER PUBLICATIONS

Vespermann, A., et al., "Rhizobacterial Volatiles Affect the Growth of Fungi and Arabidopsis thaliana," Applied and Environmental Microbiology, vol. 73, No. 17, pp. 5639-5641 (Sep. 2007).

Cho, S.M., et al., "2R,3R-Butanediol, a Bacterial Volatile Produced by Pseudomonas chloroaphis 06, Is Invloved in Induction of Systemic Tolerance to Drought in Arabidopsis thaliana," MPMI, vol. 21, No. 8, pp. 1067-1075, (2008).

Ezquer, I., et al., "Microbial Volatile Emissions Promote Accumulation of Exceptionally High Levels of Starch in Leaves in Mono- and Dicotyledonous Plants," Plant & Cell Physiology, vol. 51, No. 10, pp. 1674-1693, (2010).

Wallace, J.M., et al., "Adverse synergistic effects between acetic, propionic, butyric and valeric acids on the growth of wheat seedling roots," Soil Biol. Biochem., vol. 12, pp. 445-446, (1980).

Zhang, H., et al., "Soil bacteria augment Arabidopsis photosynthesis by decreasing glucose sensing and abscisic acid levels in planta," The Plant Journal, vol. 56, pp. 264-273, (2008).

Ortiz-Castro, R., et al., "The role of microbial signals in plant growth and development," Plant Signaling & Behavior, vol. 4, No. 8, pp. 701-712, (Aug. 2009).

Sharma, S., et al., "Carboxylic acids affect induction, development and quality of potato (*Solanum tuberosum* L.) microtubers grown in vitro fron single-node explants," Plant Growth Regulation, vol. 44, pp. 219-229, (2004).

Pelacho, A.M., et al., "In vitro induction of potato tubrerization by organic acids," Potato Research, vol. 42, pp. 585-591, (1999).

Yang, J., et al., "Rhizosphere bacteria help plants tolerate abiotic stress," Trends in Plant Science, vol. 14, No. 1, pp. 1-4, (2009).

International Search Report Issued Dec. 20, 2011 in PCT/ES11/00125 Filed Apr. 15, 2011.

\* cited by examiner

SEQUENCE LISTING

```
<160> NUMBER OF SEQ ID NOS: 78

<210> SEQ ID NO 1
<211> LENGTH: 20
<212> TYPE: DNA
<213> ORGANISM: Artificial sequence
<220> FEATURE:
<223> OTHER INFORMATION: RT-PCT forward primer for SNF4

<400> SEQUENCE: 1
ccccgtagat ctcagaagca                                                20

<210> SEQ ID NO 2
<211> LENGTH: 20
<212> TYPE: DNA
<213> ORGANISM: Artificial sequence
<220> FEATURE:
<223> OTHER INFORMATION: RT-PCT reverse primer for SNF4

<400> SEQUENCE: 2
cagcgtggct gtatatggaa                                                20
```

```
<210> SEQ ID NO 3
<211> LENGTH: 20
<212> TYPE: DNA
<213> ORGANISM: Artificial sequence
<220> FEATURE:
<223> OTHER INFORMATION: RT-PCT forward primer for
      1-phosphatidylinositol-4-phosphate 5-kinase

<400> SEQUENCE: 3
acacaagaag tggggaatgg                                                20

<210> SEQ ID NO 4
<211> LENGTH: 20
<212> TYPE: DNA
<213> ORGANISM: Artificial sequence
<220> FEATURE:
<223> OTHER INFORMATION: RT-PCT reverse primer for
      1-phosphatidylinositol-4-phosphate 5-kinase

<400> SEQUENCE: 4
ttttctgctg ccttcctagc                                                20

<210> SEQ ID NO 5
<211> LENGTH: 20
<212> TYPE: DNA
<213> ORGANISM: Artificial sequence
<220> FEATURE:
<223> OTHER INFORMATION: RT-PCT forward primer for pullulanase

<400> SEQUENCE: 5
gcgtaaacaa taccgccagt                                                20

<210> SEQ ID NO 6
<211> LENGTH: 20
<212> TYPE: DNA
<213> ORGANISM: Artificial sequence
<220> FEATURE:
<223> OTHER INFORMATION: RT-PCT reverse primer for pullulanase

<400> SEQUENCE: 6
caggtcaaac cgaaatccat                                                20

<210> SEQ ID NO 7
<211> LENGTH: 20
<212> TYPE: DNA
<213> ORGANISM: Artificial sequence
<220> FEATURE:
<223> OTHER INFORMATION: RT-PCT forward primer for
      triose-phosphate/3-phosphoglycerate translocator

<400> SEQUENCE: 7
caagatttcc cccattgcta                                                20

<210> SEQ ID NO 8
<211> LENGTH: 20
<212> TYPE: DNA
<213> ORGANISM: Artificial sequence
<220> FEATURE:
<223> OTHER INFORMATION: RT-PCT forward primer for triose
      phosphate/3-phosphoglycerate translocator

<400> SEQUENCE: 8
ttccaaccgc atgtgtaaga                                                20

<210> SEQ ID NO 9
<211> LENGTH: 20
<212> TYPE: DNA
```

```
<213> ORGANISM: Artificial sequence
<220> FEATURE:
<223> OTHER INFORMATION: RT-PCT forward primer for nitrite transporter

<400> SEQUENCE: 9
caaatacctc cagccagcat                                              20

<210> SEQ ID NO 10
<211> LENGTH: 20
<212> TYPE: DNA
<213> ORGANISM: Artificial sequence
<220> FEATURE:
<223> OTHER INFORMATION: RT-PCT reverse primer for nitrite transporter

<400> SEQUENCE: 10
tgtgaatcga cgagcaaaag                                              20

<210> SEQ ID NO 11
<211> LENGTH: 20
<212> TYPE: DNA
<213> ORGANISM: Artificial sequence
<220> FEATURE:
<223> OTHER INFORMATION: RT-PCT forward primer for trehalose-6-phosphate
      synthase

<400> SEQUENCE: 11
cgattttcag tggatgcaga                                              20

<210> SEQ ID NO 12
<211> LENGTH: 20
<212> TYPE: DNA
<213> ORGANISM: Artificial sequence
<220> FEATURE:
<223> OTHER INFORMATION: RT-PCT reverse primer for trehalose-6-phosphate
      synthase

<400> SEQUENCE: 12
gatgatgcca aacaagagca                                              20

<210> SEQ ID NO 13
<211> LENGTH: 21
<212> TYPE: DNA
<213> ORGANISM: Artificial sequence
<220> FEATURE:
<223> OTHER INFORMATION: RT-PCT forward primer for starch phosphorylase
      (plastidial form)

<400> SEQUENCE: 13
aaccaagtgg acaggatctg a                                            21

<210> SEQ ID NO 14
<211> LENGTH: 20
<212> TYPE: DNA
<213> ORGANISM: Artificial sequence
<220> FEATURE:
<223> OTHER INFORMATION: RT-PCT reverse primer for starch phosphorylase
      (plastidial form)

<400> SEQUENCE: 14
cttttgcctt cctccactca                                              20

<210> SEQ ID NO 15
<211> LENGTH: 20
<212> TYPE: DNA
<213> ORGANISM: Artificial sequence
<220> FEATURE:
<223> OTHER INFORMATION: RT-PCT forward primer for beta-amylase BMYI
```

```
<400> SEQUENCE: 15
gaggtaacac gaggcttcca                                                    20

<210> SEQ ID NO 16
<211> LENGTH: 20
<212> TYPE: DNA
<213> ORGANISM: Artificial sequence
<220> FEATURE:
<223> OTHER INFORMATION: RT-PCT reverse primer for beta-amylase BMYI

<400> SEQUENCE: 16
cacaactgca acctctgcat                                                    20

<210> SEQ ID NO 17
<211> LENGTH: 20
<212> TYPE: DNA
<213> ORGANISM: Artificial sequence
<220> FEATURE:
<223> OTHER INFORMATION: RT-PCT forward primer for thioredoxin M4

<400> SEQUENCE: 17
aagttacccg tcctggttga                                                    20

<210> SEQ ID NO 18
<211> LENGTH: 20
<212> TYPE: DNA
<213> ORGANISM: Artificial sequence
<220> FEATURE:
<223> OTHER INFORMATION: RT-PCT reverse primer for thioredoxin M4

<400> SEQUENCE: 18
acttgccagc gtattcctgt                                                    20

<210> SEQ ID NO 19
<211> LENGTH: 20
<212> TYPE: DNA
<213> ORGANISM: Artificial sequence
<220> FEATURE:
<223> OTHER INFORMATION: RT-PCT forward primer for nitrite reductase

<400> SEQUENCE: 19
tgcagacatt ggattcatgg                                                    20

<210> SEQ ID NO 20
<211> LENGTH: 21
<212> TYPE: DNA
<213> ORGANISM: Artificial sequence
<220> FEATURE:
<223> OTHER INFORMATION: RT-PCT reverse primer for nitrite reductase

<400> SEQUENCE: 20
ctcccaaatg tgaatcactc c                                                  21

<210> SEQ ID NO 21
<211> LENGTH: 20
<212> TYPE: DNA
<213> ORGANISM: Artificial sequence
<220> FEATURE:
<223> OTHER INFORMATION: RT-PCT forward primer for cysteine synthase

<400> SEQUENCE: 21
tgcctgcatc aatgagtctt                                                    20

<210> SEQ ID NO 22
```

```
<211> LENGTH: 20
<212> TYPE: DNA
<213> ORGANISM: Artificial sequence
<220> FEATURE:
<223> OTHER INFORMATION: RT-PCT reverse primer for cysteine synthase

<400> SEQUENCE: 22
cagcctttga aacagctcct                                                     20

<210> SEQ ID NO 23
<211> LENGTH: 20
<212> TYPE: DNA
<213> ORGANISM: Artificial sequence
<220> FEATURE:
<223> OTHER INFORMATION: RT-PCT forward primer for inorganic
      pyrophosphatase

<400> SEQUENCE: 23
acagcccgaa accctagatt                                                     20

<210> SEQ ID NO 24
<211> LENGTH: 20
<212> TYPE: DNA
<213> ORGANISM: Artificial sequence
<220> FEATURE:
<223> OTHER INFORMATION: RT-PCT reverse primer for inorganic
      pyrophosphatase

<400> SEQUENCE: 24
tgaaaacacc atcacccaaa                                                     20

<210> SEQ ID NO 25
<211> LENGTH: 20
<212> TYPE: DNA
<213> ORGANISM: Artificial sequence
<220> FEATURE:
<223> OTHER INFORMATION: RT-PCT forward primer for acid invertase

<400> SEQUENCE: 25
aatggagcag cacgactctt                                                     20

<210> SEQ ID NO 26
<211> LENGTH: 20
<212> TYPE: DNA
<213> ORGANISM: Artificial sequence
<220> FEATURE:
<223> OTHER INFORMATION: RT-PCT reverse primer for acid invertase

<400> SEQUENCE: 26
agtcttgcaa ggggaaggat                                                     20

<210> SEQ ID NO 27
<211> LENGTH: 20
<212> TYPE: DNA
<213> ORGANISM: Artificial sequence
<220> FEATURE:
<223> OTHER INFORMATION: RT-PCT forward primer for glucose-6-phosphate
      dehydrogenase (plastidial form)

<400> SEQUENCE: 27
cgaggagggt actttgacca                                                     20

<210> SEQ ID NO 28
<211> LENGTH: 20
<212> TYPE: DNA
<213> ORGANISM: Artificial sequence
<220> FEATURE:
```

<223> OTHER INFORMATION: RT-PCT reverse primer for glucose-6-phosphate
      dehydrogenase (plastidial form)

<400> SEQUENCE: 28
caagctgaca ggtgtttcca                                                20

<210> SEQ ID NO 29
<211> LENGTH: 20
<212> TYPE: DNA
<213> ORGANISM: Artificial sequence
<220> FEATURE:
<223> OTHER INFORMATION: RT-PCT forward primer for starch synthase III

<400> SEQUENCE: 29
cgaaagggtg cgtatatggt                                                20

<210> SEQ ID NO 30
<211> LENGTH: 20
<212> TYPE: DNA
<213> ORGANISM: Artificial sequence
<220> FEATURE:
<223> OTHER INFORMATION: RT-PCT reverse primer for starch synthase III

<400> SEQUENCE: 30
tccggactaa atccaccttg                                                20

<210> SEQ ID NO 31
<211> LENGTH: 20
<212> TYPE: DNA
<213> ORGANISM: Artificial sequence
<220> FEATURE:
<223> OTHER INFORMATION: RT-PCT forward primer for inositol-3-phosphate
      synthase

<400> SEQUENCE: 31
caagagggca atggatgagt                                                20

<210> SEQ ID NO 32
<211> LENGTH: 20
<212> TYPE: DNA
<213> ORGANISM: Artificial sequence
<220> FEATURE:
<223> OTHER INFORMATION: RT-PCT reverse primer for inositol-3-phosphate
      synthase

<400> SEQUENCE: 32
attggagcag ccaaaagaga                                                20

<210> SEQ ID NO 33
<211> LENGTH: 20
<212> TYPE: DNA
<213> ORGANISM: Artificial sequence
<220> FEATURE:
<223> OTHER INFORMATION: RT-PCT forward primer for
      fructose-2,6-bisphosphatase

<400> SEQUENCE: 33
tgggacagat ggcactatca                                                20

<210> SEQ ID NO 34
<211> LENGTH: 20
<212> TYPE: DNA
<213> ORGANISM: Artificial sequence
<220> FEATURE:
<223> OTHER INFORMATION: RT-PCT reverse primer for
      fructose-2,6-bisphosphatase

<400> SEQUENCE: 34
atccgggaca attacttcca                                              20

<210> SEQ ID NO 35
<211> LENGTH: 25
<212> TYPE: DNA
<213> ORGANISM: Artificial sequence
<220> FEATURE:
<223> OTHER INFORMATION: RT-PCT forward primer for 18S RNA

<400> SEQUENCE: 35
gggcattcgt atttcatagt cagag                                        25

<210> SEQ ID NO 36
<211> LENGTH: 26
<212> TYPE: DNA
<213> ORGANISM: Artificial sequence
<220> FEATURE:
<223> OTHER INFORMATION: RT-PCT reverse primer for 18S RNA

<400> SEQUENCE: 36
cggttcttga ttaatgaaaa catcct                                       26

<210> SEQ ID NO 37
<211> LENGTH: 20
<212> TYPE: DNA
<213> ORGANISM: Artificial sequence
<220> FEATURE:
<223> OTHER INFORMATION: RT-PCT forward primer for glucose-6-phosphate
      translocator

<400> SEQUENCE: 37
tgactggaga tggatgtgga                                              20

<210> SEQ ID NO 38
<211> LENGTH: 20
<212> TYPE: DNA
<213> ORGANISM: Artificial sequence
<220> FEATURE:
<223> OTHER INFORMATION: RT-PCT reverse primer for glucose-6-phosphate
      translocator

<400> SEQUENCE: 38
gatgggaatt gcagctagga                                              20

<210> SEQ ID NO 39
<211> LENGTH: 20
<212> TYPE: DNA
<213> ORGANISM: Artificial sequence
<220> FEATURE:
<223> OTHER INFORMATION: RT-PCT forward primer for protease inhibitor I

<400> SEQUENCE: 39
tgaaactctc atggcacgaa                                              20

<210> SEQ ID NO 40
<211> LENGTH: 20
<212> TYPE: DNA
<213> ORGANISM: Artificial sequence
<220> FEATURE:
<223> OTHER INFORMATION: RT-PCT reverse primer for protease inhibitor I

<400> SEQUENCE: 40
tggccagctt agttttccat                                              20

<210> SEQ ID NO 41
<211> LENGTH: 19
<212> TYPE: DNA
<213> ORGANISM: Artificial sequence
<220> FEATURE:
<223> OTHER INFORMATION: RT-PCT forward primer for the alpha-glucan
      branching enzyme

<400> SEQUENCE: 41
aatttggtgg ccatggaag                                              19

<210> SEQ ID NO 42
<211> LENGTH: 20
<212> TYPE: DNA
<213> ORGANISM: Artificial sequence
<220> FEATURE:
<223> OTHER INFORMATION: RT-PCT reverse primer for the alpha-glucan
      branching enzyme

<400> SEQUENCE: 42
aggaatttgg acgaccattg                                             20

<210> SEQ ID NO 43
<211> LENGTH: 21
<212> TYPE: DNA
<213> ORGANISM: Artificial sequence
<220> FEATURE:
<223> OTHER INFORMATION: RT-PCT forward primer for ADP-glucose
      pyrophosphorylase L3

<400> SEQUENCE: 43
caggtgaggc taagttgaag g                                           21

<210> SEQ ID NO 44
<211> LENGTH: 20
<212> TYPE: DNA
<213> ORGANISM: Artificial sequence
<220> FEATURE:
<223> OTHER INFORMATION: RT-PCT reverse primer for ADP-glucose
      pyrophosphorylase L3

<400> SEQUENCE: 44 gaggggggaaa agacgagttc                                            20

<210> SEQ ID NO 45
<211> LENGTH: 20
<212> TYPE: DNA
<213> ORGANISM: Artificial sequence
<220> FEATURE:
<223> OTHER INFORMATION: RT-PCT forward primer for ADP-glucose
      pyrophosphorylase L1

<400> SEQUENCE: 45
ggtgaaagat cgcgcttaga                                             20

<210> SEQ ID NO 46
<211> LENGTH: 20
<212> TYPE: DNA
<213> ORGANISM: Artificial sequence
<220> FEATURE:
<223> OTHER INFORMATION: RT-PCT reverse primer for ADP-glucose
      pyrophosphorylase L1

<400> SEQUENCE: 46
ctgctaacag ggaggcaatc                                             20

<210> SEQ ID NO 47

```
<211> LENGTH: 20
<212> TYPE: DNA
<213> ORGANISM: Artificial sequence
<220> FEATURE:
<223> OTHER INFORMATION: RT-PCT forward primer for the Kunitz-type tuber
      invertase inhibitor

<400> SEQUENCE: 47
aaaccttcaa tgcccaaatg                                              20

<210> SEQ ID NO 48
<211> LENGTH: 20
<212> TYPE: DNA
<213> ORGANISM: Artificial sequence
<220> FEATURE:
<223> OTHER INFORMATION: RT-PCT reverse primer for the Kunitz-type tuber
      invertase inhibitor

<400> SEQUENCE: 48
attccgactc cgacttacga                                              20

<210> SEQ ID NO 49
<211> LENGTH: 20
<212> TYPE: DNA
<213> ORGANISM: Artificial sequence
<220> FEATURE:
<223> OTHER INFORMATION: RT-PCT forward primer for sucrose synthase 4

<400> SEQUENCE: 49
tgggaataca tccgtgtgaa                                              20

<210> SEQ ID NO 50
<211> LENGTH: 20
<212> TYPE: DNA
<213> ORGANISM: Artificial sequence
<220> FEATURE:
<223> OTHER INFORMATION: RT-PCT reverse primer for sucrose synthase 4

<400> SEQUENCE: 50
gctccgtcga caagttcttc                                              20

<210> SEQ ID NO 51
<211> LENGTH: 20
<212> TYPE: DNA
<213> ORGANISM: Artificial sequence
<220> FEATURE:
<223> OTHER INFORMATION: RT-PCT forward primer for the Dnak-type
      chaperone Hsc70

<400> SEQUENCE: 51
tgcaagctgc aatcttgagt                                              20

<210> SEQ ID NO 52
<211> LENGTH: 20
<212> TYPE: DNA
<213> ORGANISM: Artificial sequence
<220> FEATURE:
<223> OTHER INFORMATION: RT-PCT reverse primer for the Dnak-type
      chaperone Hsc70

<400> SEQUENCE: 52
acacctccag cagtctccag                                              20

<210> SEQ ID NO 53
<211> LENGTH: 20
<212> TYPE: DNA
<213> ORGANISM: Artificial sequence
```

```
<220> FEATURE:
<223> OTHER INFORMATION: RT-PCT forward primer for starch synthase IV

<400> SEQUENCE: 53
catcgtctct tgcgcctaat                                                     20

<210> SEQ ID NO 54
<211> LENGTH: 20
<212> TYPE: DNA
<213> ORGANISM: Artificial sequence
<220> FEATURE:
<223> OTHER INFORMATION: RT-PCT reverse primer for starch synthase IV

<400> SEQUENCE: 54
atggccttac tgctgacgtt                                                     20

<210> SEQ ID NO 55
<211> LENGTH: 20
<212> TYPE: DNA
<213> ORGANISM: Artificial sequence
<220> FEATURE:
<223> OTHER INFORMATION: RT-PCT forward primer for the Real-SpoT-like
      RSH4 protein

<400> SEQUENCE: 55
acaagggcgg tgttactgat                                                     20

<210> SEQ ID NO 56
<211> LENGTH: 20
<212> TYPE: DNA
<213> ORGANISM: Artificial sequence
<220> FEATURE:
<223> OTHER INFORMATION: RT-PCT reverse primer for the Real-SpoT-like
      RSH4 protein

<400> SEQUENCE: 56
tcgccgaagg aaaatctcta                                                     20

<210> SEQ ID NO 57
<211> LENGTH: 20
<212> TYPE: DNA
<213> ORGANISM: Artificial sequence
<220> FEATURE:
<223> OTHER INFORMATION: RT-PCT forward primer for
      sedoheptulose-1,7-bisphosphatase

<400> SEQUENCE: 57
gaaccatctt tggcgtatgg                                                     20

<210> SEQ ID NO 58
<211> LENGTH: 20
<212> TYPE: DNA
<213> ORGANISM: Artificial sequence
<220> FEATURE:
<223> OTHER INFORMATION: RT-PCT reverse primer for
      sedoheptulose-1,7-bisphosphatase

<400> SEQUENCE: 58
catatgtagt tcgcggtcca                                                     20

<210> SEQ ID NO 59
<211> LENGTH: 20
<212> TYPE: DNA
<213> ORGANISM: Artificial sequence
<220> FEATURE:
<223> OTHER INFORMATION: RT-PCT reverse primer for fructose-bisphosphate
      aldolase
```

<400> SEQUENCE: 59
ggaaaggtat tttggcagca                                                    20

<210> SEQ ID NO 60
<211> LENGTH: 20
<212> TYPE: DNA
<213> ORGANISM: Artificial sequence
<220> FEATURE:
<223> OTHER INFORMATION: RT-PCT reverse primer for fructose-bisphosphate
      aldolase

<400> SEQUENCE: 60
gttgacgaag tgcttgacga                                                    20

<210> SEQ ID NO 61
<211> LENGTH: 20
<212> TYPE: DNA
<213> ORGANISM: Artificial sequence
<220> FEATURE:
<223> OTHER INFORMATION: RT-PCT forward primer for chloroplast
      fructose-1,6-bisphosphatase

<400> SEQUENCE: 61
ttcgatggct tgtaagcaga                                                    20

<210> SEQ ID NO 62
<211> LENGTH: 20
<212> TYPE: DNA
<213> ORGANISM: Artificial sequence
<220> FEATURE:
<223> OTHER INFORMATION: RT-PCT reverse primer for chloroplast
      fructose-1,6-bisphosphatase

<400> SEQUENCE: 62
ttttggtcct ctccatgagc                                                    20

<210> SEQ ID NO 63
<211> LENGTH: 20
<212> TYPE: DNA
<213> ORGANISM: Artificial sequence
<220> FEATURE:
<223> OTHER INFORMATION: RT-PCT reverse primer for cytosolic
      fructose-1,6-bisphosphatase

<400> SEQUENCE: 63
tatcccgctg atggttcttc                                                    20

<210> SEQ ID NO 64
<211> LENGTH: 20
<212> TYPE: DNA
<213> ORGANISM: Artificial sequence
<220> FEATURE:
<223> OTHER INFORMATION: RT-PCT reverse primer for cytosolic
      fructose-1,6-bisphosphatase

<400> SEQUENCE: 64
ctccggggta caagaagatg                                                    20

<210> SEQ ID NO 65
<211> LENGTH: 20
<212> TYPE: DNA
<213> ORGANISM: Artificial sequence
<220> FEATURE:
<223> OTHER INFORMATION: RT-PCT forward primer for
      glyceraldehyde-3-phosphate dehydrogenase (plastidial isoform)

<400> SEQUENCE: 65
cacaccgtga cttgaggaga                                                20

<210> SEQ ID NO 66
<211> LENGTH: 20
<212> TYPE: DNA
<213> ORGANISM: Artificial sequence
<220> FEATURE:
<223> OTHER INFORMATION: RT-PCT reverse primer for
      glyceraldehyde-3-phosphate dehydrogenase (plastidial isoform)

<400> SEQUENCE: 66
cccttgagct gaggtagcac                                                20

<210> SEQ ID NO 67
<211> LENGTH: 324
<212> TYPE: DNA
<213> ORGANISM: Solanum tuberosum
<220> FEATURE:
<221> NAME/KEY: CDS
<222> LOCATION: (1)..(324)
<223> OTHER INFORMATION: Sequence encoding the potato protease inhibitor

<400> SEQUENCE: 67

```
atg gag tca aag tgt gct cac atc att gtt ttc ttt ctt ctt gca act        48
Met Glu Ser Lys Cys Ala His Ile Ile Val Phe Phe Leu Leu Ala Thr
1               5                   10                  15 tcc ttt gaa act ctc atg gca caa aaa gaa agt gat gga cta gaa gcc        96
Ser Phe Glu Thr Leu Met Ala Gln Lys Glu Ser Asp Gly Leu Glu Ala
                20                  25                  30 ata gaa ctt cta aag gaa ttt gaa tgc aaa gga aaa cta agc tgg cca       144
Ile Glu Leu Leu Lys Glu Phe Glu Cys Lys Gly Lys Leu Ser Trp Pro
            35                  40                  45 gaa ctt att ggt gta cca aca aag ctt gct aag ggg ata att gag aag       192
Glu Leu Ile Gly Val Pro Thr Lys Leu Ala Lys Gly Ile Ile Glu Lys
        50                  55                  60 caa aat tca ctc ata agt aat gtt cat ata tta ttg aat ggt tct cca       240
Gln Asn Ser Leu Ile Ser Asn Val His Ile Leu Leu Asn Gly Ser Pro
65                  70                  75                  80 gtc aca ttg gat att cgt tgt gat cga gtt cgt ctt ttt gat aac atc       288
Val Thr Leu Asp Ile Arg Cys Asp Arg Val Arg Leu Phe Asp Asn Ile
                85                  90                  95 ttg ggt tct gtt gta cag att cct gtg gtt ggt taa                       324
Leu Gly Ser Val Val Gln Ile Pro Val Val Gly
                100                 105
```

<210> SEQ ID NO 68
<211> LENGTH: 107
<212> TYPE: PRT
<213> ORGANISM: Solanum tuberosum

<400> SEQUENCE: 68

Met Glu Ser Lys Cys Ala His Ile Ile Val Phe Phe Leu Leu Ala Thr
1               5                   10                  15

Ser Phe Glu Thr Leu Met Ala Gln Lys Glu Ser Asp Gly Leu Glu Ala
                20                  25                  30

Ile Glu Leu Leu Lys Glu Phe Glu Cys Lys Gly Lys Leu Ser Trp Pro
            35                  40                  45

Glu Leu Ile Gly Val Pro Thr Lys Leu Ala Lys Gly Ile Ile Glu Lys
        50                  55                  60

Gln Asn Ser Leu Ile Ser Asn Val His Ile Leu Leu Asn Gly Ser Pro
65                  70                  75                  80

```
Val Thr Leu Asp Ile Arg Cys Asp Arg Val Arg Leu Phe Asp Asn Ile
             85                  90                  95

Leu Gly Ser Val Val Gln Ile Pro Val Val Gly
        100                 105

<210> SEQ ID NO 69
<211> LENGTH: 1764
<212> TYPE: DNA
<213> ORGANISM: Solanum tuberosum
<220> FEATURE:
<221> NAME/KEY: CDS
<222> LOCATION: (1)..(1764)
<223> OTHER INFORMATION: Sequence encoding potato nitrite reductase

<400> SEQUENCE: 69 atg gca tct ttt tct atc aaa ttt ttg gca cct tca ttg cca aat cca      48
Met Ala Ser Phe Ser Ile Lys Phe Leu Ala Pro Ser Leu Pro Asn Pro
1               5                   10                  15 act aga ttt tcc aag agt act att gtc aag ctc aat gca act ccg ccg      96
Thr Arg Phe Ser Lys Ser Thr Ile Val Lys Leu Asn Ala Thr Pro Pro
            20                  25                  30 cag aca gtg gct gcg gtg ggg cct cca gag gtt gct gct gag aga cta     144
Gln Thr Val Ala Ala Val Gly Pro Pro Glu Val Ala Ala Glu Arg Leu
        35                  40                  45 gaa cca aga gtt gag gaa aaa gat gga tat tgg ata caa aaa gag cag     192
Glu Pro Arg Val Glu Glu Lys Asp Gly Tyr Trp Ile Gln Lys Glu Gln
    50                  55                  60 ttt agg caa ggt att aat cct caa gag aag gtg aag att gag aag gaa     240
Phe Arg Gln Gly Ile Asn Pro Gln Glu Lys Val Lys Ile Glu Lys Glu
65                  70                  75                  80 cct atg aag ttg ttc atg gaa aat ggt att gaa gag tta gct aag att     288
Pro Met Lys Leu Phe Met Glu Asn Gly Ile Glu Glu Leu Ala Lys Ile
                85                  90                  95 cca att gaa gag ata gat caa tct aag ctt act aag gat gac atc gat     336
Pro Ile Glu Glu Ile Asp Gln Ser Lys Leu Thr Lys Asp Asp Ile Asp
            100                 105                 110 gtt agg ctt aag tgg ctt ggc ctc ttc cat agg aga aag aat caa tat     384
Val Arg Leu Lys Trp Leu Gly Leu Phe His Arg Arg Lys Asn Gln Tyr
        115                 120                 125 ggg aga ttc atg atg agg ttg aaa ctt cca aat gga gta aca acg agt     432
Gly Arg Phe Met Met Arg Leu Lys Leu Pro Asn Gly Val Thr Thr Ser
    130                 135                 140 gct caa act cga tat ttg gca agt gtg ata agg aaa tac ggg gag gaa     480
Ala Gln Thr Arg Tyr Leu Ala Ser Val Ile Arg Lys Tyr Gly Glu Glu
145                 150                 155                 160 gga tgt gct gat att acg aca agg caa aat tgg cag att cgt gga gtt     528
Gly Cys Ala Asp Ile Thr Thr Arg Gln Asn Trp Gln Ile Arg Gly Val
                165                 170                 175 gtg cta cct gat gtg cct gag att ctg aag gga ctt gaa gaa gtt ggc     576
Val Leu Pro Asp Val Pro Glu Ile Leu Lys Gly Leu Glu Glu Val Gly
            180                 185                 190 ttg act agt ttg cag agt ggc atg gat aat gtc agg aat cca gtt gga     624
Leu Thr Ser Leu Gln Ser Gly Met Asp Asn Val Arg Asn Pro Val Gly
        195                 200                 205 aat cct ctg gct gga att gat cct gaa gaa att gtt gac aca aga cct     672
Asn Pro Leu Ala Gly Ile Asp Pro Glu Glu Ile Val Asp Thr Arg Pro
    210                 215                 220 tac act aat ttg ctc tcc caa ttt atc act ggt aat tca cga ggc aat     720
Tyr Thr Asn Leu Leu Ser Gln Phe Ile Thr Gly Asn Ser Arg Gly Asn
225                 230                 235                 240
```

```
ccg gca gtt tct aac ttg cca agg aag tgg aat ccg tgt gta gta ggc      768
Pro Ala Val Ser Asn Leu Pro Arg Lys Trp Asn Pro Cys Val Val Gly
                245                 250                 255 tct cat gat ctt tat gag cac cct cat atc aat gat ctt gca tac atg      816
Ser His Asp Leu Tyr Glu His Pro His Ile Asn Asp Leu Ala Tyr Met
                260                 265                 270 cct gcc ata aaa gat gga cga ttc gga ttc aac ctg ctt gtg gga ggg      864
Pro Ala Ile Lys Asp Gly Arg Phe Gly Phe Asn Leu Leu Val Gly Gly
                275                 280                 285 ttc ttc agt gcc aaa cga tgt gat gag gca att cct ctt gat gca tgg      912
Phe Phe Ser Ala Lys Arg Cys Asp Glu Ala Ile Pro Leu Asp Ala Trp
                290                 295                 300 gtt cca gct gat gat gtt gtt ccg gtt tgc aaa gca atc ctg gaa gct      960
Val Pro Ala Asp Asp Val Val Pro Val Cys Lys Ala Ile Leu Glu Ala
305                 310                 315                 320 ttt aga gat ctt ggt ttc aga ggg aac agg cag aaa tgt aga atg atg     1008
Phe Arg Asp Leu Gly Phe Arg Gly Asn Arg Gln Lys Cys Arg Met Met
                325                 330                 335 tgg tta atc gat gaa ctg ggt gta gaa gga ttc agg gca gag gtt gaa     1056
Trp Leu Ile Asp Glu Leu Gly Val Glu Gly Phe Arg Ala Glu Val Glu
                340                 345                 350 aag aga atg cct cag caa gag cta gag aga gca tct ccg gaa gac ttg     1104
Lys Arg Met Pro Gln Gln Glu Leu Glu Arg Ala Ser Pro Glu Asp Leu
                355                 360                 365 gtt cag aaa caa tgg gaa aga aga gat tat ctt ggt gta cat cca caa     1152
Val Gln Lys Gln Trp Glu Arg Arg Asp Tyr Leu Gly Val His Pro Gln
                370                 375                 380 aaa cag gaa ggc tat agt ttt att ggt ctt cac att cca gtg ggt cgt     1200
Lys Gln Glu Gly Tyr Ser Phe Ile Gly Leu His Ile Pro Val Gly Arg
385                 390                 395                 400 gtc caa gca gac gac atg gat gat cta gct cgt ttg gct gat gag tat     1248
Val Gln Ala Asp Asp Met Asp Asp Leu Ala Arg Leu Ala Asp Glu Tyr
                405                 410                 415 ggc tca gga gag cta cgg ctg act gtg gaa cag aac att att att ccc     1296
Gly Ser Gly Glu Leu Arg Leu Thr Val Glu Gln Asn Ile Ile Ile Pro
                420                 425                 430 aac att gag aac tca aag att gag gca ctg cta aaa gag cct att ttg     1344
Asn Ile Glu Asn Ser Lys Ile Glu Ala Leu Leu Lys Glu Pro Ile Leu
                435                 440                 445 agc aaa ttt tca cct gat cca cct att ctc atg aaa ggt tta gtg gct     1392
Ser Lys Phe Ser Pro Asp Pro Pro Ile Leu Met Lys Gly Leu Val Ala
                450                 455                 460 tgt act ggt aac cag ttt tgt gga caa gcc ata att gag aca aaa gct     1440
Cys Thr Gly Asn Gln Phe Cys Gly Gln Ala Ile Ile Glu Thr Lys Ala
465                 470                 475                 480 cgt tcc ctg aag atc acc gaa gag gtt caa agg caa gta tct cta acg     1488
Arg Ser Leu Lys Ile Thr Glu Glu Val Gln Arg Gln Val Ser Leu Thr
                485                 490                 495 agg cca gta agg atg cac tgg aca ggc tgc ccg aat acg tgt gca caa     1536
Arg Pro Val Arg Met His Trp Thr Gly Cys Pro Asn Thr Cys Ala Gln
                500                 505                 510 gtt caa gtt gca gac att gga ttc atg gga tgc ctg act aga gat aag     1584
Val Gln Val Ala Asp Ile Gly Phe Met Gly Cys Leu Thr Arg Asp Lys
                515                 520                 525 gac aag aag act gtg gaa ggc gcc gat gtt ttc tta gga ggc aga ata     1632
Asp Lys Lys Thr Val Glu Gly Ala Asp Val Phe Leu Gly Gly Arg Ile
530                 535                 540 ggg agt gat tca cat ttg gga gaa gta tac aag aaa gcc gtt ccg tgt     1680
Gly Ser Asp Ser His Leu Gly Glu Val Tyr Lys Lys Ala Val Pro Cys
545                 550                 555                 560
```

```
gat gaa tta gta cca ctt att gtg gac tta cta gtt aac aac ttt ggt      1728
Asp Glu Leu Val Pro Leu Ile Val Asp Leu Leu Val Asn Asn Phe Gly
                565                 570                 575 gca gtt cca cga gaa aga gaa gaa aca gaa gat taa                      1764
Ala Val Pro Arg Glu Arg Glu Glu Thr Glu Asp
            580                 585
```

<210> SEQ ID NO 70
<211> LENGTH: 587
<212> TYPE: PRT
<213> ORGANISM: Solanum tuberosum

<400> SEQUENCE: 70

```
Met Ala Ser Phe Ser Ile Lys Phe Leu Ala Pro Ser Leu Pro Asn Pro
1               5                   10                  15

Thr Arg Phe Ser Lys Ser Thr Ile Val Lys Leu Asn Ala Thr Pro Pro
            20                  25                  30

Gln Thr Val Ala Ala Val Gly Pro Pro Glu Val Ala Ala Glu Arg Leu
        35                  40                  45

Glu Pro Arg Val Glu Glu Lys Asp Gly Tyr Trp Ile Gln Lys Glu Gln
    50                  55                  60

Phe Arg Gln Gly Ile Asn Pro Gln Glu Lys Val Lys Ile Glu Lys Glu
65                  70                  75                  80

Pro Met Lys Leu Phe Met Glu Asn Gly Ile Glu Glu Leu Ala Lys Ile
                85                  90                  95

Pro Ile Glu Glu Ile Asp Gln Ser Lys Leu Thr Lys Asp Asp Ile Asp
            100                 105                 110

Val Arg Leu Lys Trp Leu Gly Leu Phe His Arg Lys Asn Gln Tyr
        115                 120                 125

Gly Arg Phe Met Met Arg Leu Lys Leu Pro Asn Gly Val Thr Thr Ser
    130                 135                 140

Ala Gln Thr Arg Tyr Leu Ala Ser Val Ile Arg Lys Tyr Gly Glu Glu
145                 150                 155                 160

Gly Cys Ala Asp Ile Thr Thr Arg Gln Asn Trp Gln Ile Arg Gly Val
                165                 170                 175

Val Leu Pro Asp Val Pro Glu Ile Leu Lys Gly Leu Glu Glu Val Gly
            180                 185                 190

Leu Thr Ser Leu Gln Ser Gly Met Asp Asn Val Arg Asn Pro Val Gly
        195                 200                 205

Asn Pro Leu Ala Gly Ile Asp Pro Glu Glu Ile Val Asp Thr Arg Pro
    210                 215                 220

Tyr Thr Asn Leu Leu Ser Gln Phe Ile Thr Gly Asn Ser Arg Gly Asn
225                 230                 235                 240

Pro Ala Val Ser Asn Leu Pro Arg Lys Trp Asn Pro Cys Val Val Gly
                245                 250                 255

Ser His Asp Leu Tyr Glu His Pro His Ile Asn Asp Leu Ala Tyr Met
            260                 265                 270

Pro Ala Ile Lys Asp Gly Arg Phe Gly Phe Asn Leu Leu Val Gly Gly
        275                 280                 285

Phe Phe Ser Ala Lys Arg Cys Asp Glu Ala Ile Pro Leu Asp Ala Trp
    290                 295                 300

Val Pro Ala Asp Asp Val Val Pro Val Cys Lys Ala Ile Leu Glu Ala
305                 310                 315                 320

Phe Arg Asp Leu Gly Phe Arg Gly Asn Arg Gln Lys Cys Arg Met Met
                325                 330                 335
```

```
Trp Leu Ile Asp Glu Leu Gly Val Glu Gly Phe Arg Ala Glu Val Glu
            340                 345                 350

Lys Arg Met Pro Gln Gln Glu Leu Arg Ala Ser Pro Glu Asp Leu
        355                 360                 365

Val Gln Lys Gln Trp Glu Arg Arg Asp Tyr Leu Gly Val His Pro Gln
    370                 375                 380

Lys Gln Glu Gly Tyr Ser Phe Ile Gly Leu His Ile Pro Val Gly Arg
385                 390                 395                 400

Val Gln Ala Asp Asp Met Asp Asp Leu Ala Arg Leu Ala Asp Glu Tyr
            405                 410                 415

Gly Ser Gly Glu Leu Arg Leu Thr Val Glu Gln Asn Ile Ile Pro
        420                 425                 430

Asn Ile Glu Asn Ser Lys Ile Glu Ala Leu Leu Lys Glu Pro Ile Leu
            435                 440                 445

Ser Lys Phe Ser Pro Asp Pro Pro Ile Leu Met Lys Gly Leu Val Ala
    450                 455                 460

Cys Thr Gly Asn Gln Phe Cys Gly Gln Ala Ile Ile Glu Thr Lys Ala
465                 470                 475                 480

Arg Ser Leu Lys Ile Thr Glu Glu Val Gln Arg Gln Val Ser Leu Thr
                485                 490                 495

Arg Pro Val Arg Met His Trp Thr Gly Cys Pro Asn Thr Cys Ala Gln
            500                 505                 510

Val Gln Val Ala Asp Ile Gly Phe Met Gly Cys Leu Thr Arg Asp Lys
        515                 520                 525

Asp Lys Lys Thr Val Glu Gly Ala Asp Val Phe Leu Gly Gly Arg Ile
    530                 535                 540

Gly Ser Asp Ser His Leu Gly Glu Val Tyr Lys Lys Ala Val Pro Cys
545                 550                 555                 560

Asp Glu Leu Val Pro Leu Ile Val Asp Leu Leu Val Asn Asn Phe Gly
                565                 570                 575

Ala Val Pro Arg Glu Arg Glu Thr Glu Asp
            580                 585

<210> SEQ ID NO 71
<211> LENGTH: 1161
<212> TYPE: DNA
<213> ORGANISM: Solanum tuberosum
<220> FEATURE:
<221> NAME/KEY: CDS
<222> LOCATION: (1)..(1161)
<223> OTHER INFORMATION: Sequence encoding potato cysteine synthase

<400> SEQUENCE: 71 atg gca tct ttc atc aac aat ccc tta act tct ctc tgt aac act aag    48
Met Ala Ser Phe Ile Asn Asn Pro Leu Thr Ser Leu Cys Asn Thr Lys
1               5                   10                  15 tct gaa gct aat aat ctc ttc aaa att tcc cct tta aga gct caa tca    96
Ser Glu Ala Asn Asn Leu Phe Lys Ile Ser Pro Leu Arg Ala Gln Ser
                20                  25                  30 ctg ggt ttt tcc aag ctt aat ggc agc aga aaa gtt gct ttc cct tct   144
Leu Gly Phe Ser Lys Leu Asn Gly Ser Arg Lys Val Ala Phe Pro Ser
            35                  40                  45 gtt gtt tgc aaa gcg gtg tct gta cca acg aaa tcg agt aca gag att   192
Val Val Cys Lys Ala Val Ser Val Pro Thr Lys Ser Ser Thr Glu Ile
        50                  55                  60 gaa ggg ctt aac atc gct gaa gat gtt aca cag ctt att ggg aac aca   240
Glu Gly Leu Asn Ile Ala Glu Asp Val Thr Gln Leu Ile Gly Asn Thr
```

```
                65                  70                  75                  80
cca atg gtt tac ctt aac acc atc gct aag ggt tgt gta gca aac att          288
Pro Met Val Tyr Leu Asn Thr Ile Ala Lys Gly Cys Val Ala Asn Ile
                    85                  90                  95 gct gct aaa ctt gag att atg gag cca tgt tgc agt gtt aag gac agg          336
Ala Ala Lys Leu Glu Ile Met Glu Pro Cys Cys Ser Val Lys Asp Arg
            100                 105                 110 ata ggg ttc agt atg ata gtt gat gca gag gag aag gga ctt ata tct          384
Ile Gly Phe Ser Met Ile Val Asp Ala Glu Glu Lys Gly Leu Ile Ser
        115                 120                 125 ccg ggg aag act gtt cta gtt gag cct aca agt gga aac aca ggc att          432
Pro Gly Lys Thr Val Leu Val Glu Pro Thr Ser Gly Asn Thr Gly Ile
    130                 135                 140 ggg ctt gcc ttc att gct gct tcc aga gga tat aag ctc atc tta acg          480
Gly Leu Ala Phe Ile Ala Ala Ser Arg Gly Tyr Lys Leu Ile Leu Thr
145                 150                 155                 160 atg cct gca tca atg agt ctt gaa aga agg gtc att cta aaa gct ttt          528
Met Pro Ala Ser Met Ser Leu Glu Arg Arg Val Ile Leu Lys Ala Phe
                165                 170                 175 gga gct gaa ctt gtt tta act gac cca gcc aaa ggg atg aaa gga gct          576
Gly Ala Glu Leu Val Leu Thr Asp Pro Ala Lys Gly Met Lys Gly Ala
            180                 185                 190 gtt tca aag gct gaa gaa ata ttg aat aac aca cca gat gcc tat atc          624
Val Ser Lys Ala Glu Glu Ile Leu Asn Asn Thr Pro Asp Ala Tyr Ile
        195                 200                 205 ctt caa caa ttt gac aat ccc gcc aac ccc aag ata cac tat gaa aca          672
Leu Gln Gln Phe Asp Asn Pro Ala Asn Pro Lys Ile His Tyr Glu Thr
    210                 215                 220 acg ggt cca gag atc tgg gaa gac aca aaa ggc aag att gac ata ctt          720
Thr Gly Pro Glu Ile Trp Glu Asp Thr Lys Gly Lys Ile Asp Ile Leu
225                 230                 235                 240 gtt gct ggc att gga act ggt gga acc att aca gga aca ggc cga ttc          768
Val Ala Gly Ile Gly Thr Gly Gly Thr Ile Thr Gly Thr Gly Arg Phe
                245                 250                 255 ctt aaa gag caa aat cca aac att aag att att ggt gtg gag ccc aca          816
Leu Lys Glu Gln Asn Pro Asn Ile Lys Ile Ile Gly Val Glu Pro Thr
            260                 265                 270 gaa agt aac gtt cta tca ggg ggc aaa cct ggc cct cac aaa att caa          864
Glu Ser Asn Val Leu Ser Gly Gly Lys Pro Gly Pro His Lys Ile Gln
        275                 280                 285 ggg att gga gca ggt ttt att cca gga aac ttg gat caa gat gta atg          912
Gly Ile Gly Ala Gly Phe Ile Pro Gly Asn Leu Asp Gln Asp Val Met
    290                 295                 300 gat gaa gtg ata gag ata tcg agt gac gaa gct gtt gaa act gcg aag          960
Asp Glu Val Ile Glu Ile Ser Ser Asp Glu Ala Val Glu Thr Ala Lys
305                 310                 315                 320 caa tta gcg cta caa gaa ggg ttg ttg gtt ggg att tct tcc gga gca         1008
Gln Leu Ala Leu Gln Glu Gly Leu Leu Val Gly Ile Ser Ser Gly Ala
                325                 330                 335 gct gct ctt gct gcc att cag gtt ggg aag aga cct gag aat gca gga         1056
Ala Ala Leu Ala Ala Ile Gln Val Gly Lys Arg Pro Glu Asn Ala Gly
            340                 345                 350 aag ctt att ggg gtt gta ttt cca agc tat ggg gaa cga tac ctc tcc         1104
Lys Leu Ile Gly Val Val Phe Pro Ser Tyr Gly Glu Arg Tyr Leu Ser
        355                 360                 365 tct att ctt ttc cag tca ata cga gag gaa tgc gag aaa atg aag cca         1152
Ser Ile Leu Phe Gln Ser Ile Arg Glu Glu Cys Glu Lys Met Lys Pro
    370                 375                 380 gaa ttg tga                                                             1161
```

Glu Leu
385

<210> SEQ ID NO 72
<211> LENGTH: 386
<212> TYPE: PRT
<213> ORGANISM: Solanum tuberosum

<400> SEQUENCE: 72

```
Met Ala Ser Phe Ile Asn Asn Pro Leu Thr Ser Leu Cys Asn Thr Lys
1               5                   10                  15

Ser Glu Ala Asn Asn Leu Phe Lys Ile Ser Pro Leu Arg Ala Gln Ser
            20                  25                  30

Leu Gly Phe Ser Lys Leu Asn Gly Ser Arg Lys Val Ala Phe Pro Ser
        35                  40                  45

Val Val Cys Lys Ala Val Ser Val Pro Thr Lys Ser Ser Thr Glu Ile
    50                  55                  60

Glu Gly Leu Asn Ile Ala Glu Asp Val Thr Gln Leu Ile Gly Asn Thr
65                  70                  75                  80

Pro Met Val Tyr Leu Asn Thr Ile Ala Lys Gly Cys Val Ala Asn Ile
                85                  90                  95

Ala Ala Lys Leu Glu Ile Met Glu Pro Cys Cys Ser Val Lys Asp Arg
            100                 105                 110

Ile Gly Phe Ser Met Ile Val Asp Ala Glu Lys Gly Leu Ile Ser
        115                 120                 125

Pro Gly Lys Thr Val Leu Val Glu Pro Thr Ser Gly Asn Thr Gly Ile
    130                 135                 140

Gly Leu Ala Phe Ile Ala Ala Ser Arg Gly Tyr Lys Leu Ile Leu Thr
145                 150                 155                 160

Met Pro Ala Ser Met Ser Leu Glu Arg Arg Val Ile Leu Lys Ala Phe
                165                 170                 175

Gly Ala Glu Leu Val Leu Thr Asp Pro Ala Lys Gly Met Lys Gly Ala
            180                 185                 190

Val Ser Lys Ala Glu Glu Ile Leu Asn Asn Thr Pro Asp Ala Tyr Ile
        195                 200                 205

Leu Gln Gln Phe Asp Asn Pro Ala Asn Pro Lys Ile His Tyr Glu Thr
    210                 215                 220

Thr Gly Pro Glu Ile Trp Glu Asp Thr Lys Gly Lys Ile Asp Ile Leu
225                 230                 235                 240

Val Ala Gly Ile Gly Thr Gly Gly Thr Ile Thr Gly Thr Gly Arg Phe
                245                 250                 255

Leu Lys Glu Gln Asn Pro Asn Ile Lys Ile Ile Gly Val Glu Pro Thr
            260                 265                 270

Glu Ser Asn Val Leu Ser Gly Gly Lys Pro Gly Pro His Lys Ile Gln
        275                 280                 285

Gly Ile Gly Ala Gly Phe Ile Pro Gly Asn Leu Asp Gln Asp Val Met
    290                 295                 300

Asp Glu Val Ile Glu Ile Ser Ser Asp Glu Ala Val Glu Thr Ala Lys
305                 310                 315                 320

Gln Leu Ala Leu Gln Glu Gly Leu Leu Val Gly Ile Ser Ser Gly Ala
                325                 330                 335

Ala Ala Leu Ala Ala Ile Gln Val Gly Lys Arg Pro Glu Asn Ala Gly
            340                 345                 350

Lys Leu Ile Gly Val Val Phe Pro Ser Tyr Gly Glu Arg Tyr Leu Ser
        355                 360                 365
```

Ser Ile Leu Phe Gln Ser Ile Arg Glu Glu Cys Glu Lys Met Lys Pro
    370                 375                 380

Glu Leu
385

<210> SEQ ID NO 73
<211> LENGTH: 55
<212> TYPE: DNA
<213> ORGANISM: Artificial sequence
<220> FEATURE:
<223> OTHER INFORMATION: PCR primer for potato protease inhibitor
<220> FEATURE:
<221> NAME/KEY: misc_feature
<222> LOCATION: (1)..(29)
<223> OTHER INFORMATION: attB1 sequence
<220> FEATURE:
<221> NAME/KEY: misc_feature
<222> LOCATION: (32)..(55)
<223> OTHER INFORMATION: sequence complementary to the potato protease
      inhibitor gene

<400> SEQUENCE: 73
ggggacaagt ttgtacaaaa aagcaggctt aatggagtca agtgtgctc acatc         55

<210> SEQ ID NO 74
<211> LENGTH: 54
<212> TYPE: DNA
<213> ORGANISM: Artificial sequence
<220> FEATURE:
<223> OTHER INFORMATION: PCR primer for potato protease inhibitor
<220> FEATURE:
<221> NAME/KEY: misc_feature
<222> LOCATION: (1)..(29)
<223> OTHER INFORMATION: attB2 sequence
<220> FEATURE:
<221> NAME/KEY: misc_feature
<222> LOCATION: (31)..(54)
<223> OTHER INFORMATION: sequence complementary to the potato protease
      inhibitor gene

<400> SEQUENCE: 74
ggggaccact ttgtacaaga aagctgggta ttaaccaacc acaggaatct gtac          54

<210> SEQ ID NO 75
<211> LENGTH: 57
<212> TYPE: DNA
<213> ORGANISM: Artificial sequence
<220> FEATURE:
<223> OTHER INFORMATION: PCR primer for potato nitrite reductase
<220> FEATURE:
<221> NAME/KEY: misc_feature
<222> LOCATION: (1)..(29)
<223> OTHER INFORMATION: attB1 sequence
<220> FEATURE:
<221> NAME/KEY: misc_feature
<222> LOCATION: (32)..(57)
<223> OTHER INFORMATION: sequence complementary to the potato nitrite
      reductase gene

<400> SEQUENCE: 75
ggggacaagt ttgtacaaaa aagcaggctt attaatcttc tgtttcttct ctttctc       57

<210> SEQ ID NO 76
<211> LENGTH: 57
<212> TYPE: DNA
<213> ORGANISM: Artificial sequence
<220> FEATURE:
<223> OTHER INFORMATION: PCR primer for potato nitrite reductase
<220> FEATURE:
<221> NAME/KEY: misc_feature

```
<222> LOCATION: (1)..(29)
<223> OTHER INFORMATION: attB2 sequence
<220> FEATURE:
<221> NAME/KEY: misc_feature
<222> LOCATION: (31)..(57)
<223> OTHER INFORMATION: sequence complementary to the potato nitrite
      reductase gene

<400> SEQUENCE: 76
ggggaccact ttgtacaaga aagctgggta atggcatctt tttctatcaa atttttg          57

<210> SEQ ID NO 77
<211> LENGTH: 55
<212> TYPE: DNA
<213> ORGANISM: Artificial sequence
<220> FEATURE:
<223> OTHER INFORMATION: PCR primer for potato cysteine synthase
<220> FEATURE:
<221> NAME/KEY: misc_feature
<222> LOCATION: (1)..(29)
<223> OTHER INFORMATION: attB1 sequence
<220> FEATURE:
<221> NAME/KEY: misc_feature
<222> LOCATION: (32)..(55)
<223> OTHER INFORMATION: sequence complementary to the potato cysteine
      synthase gene

<400> SEQUENCE: 77
ggggacaagt ttgtacaaaa aagcaggctt atcacaattc tggcttcatt ttctc            55

<210> SEQ ID NO 78
<211> LENGTH: 53
<212> TYPE: DNA
<213> ORGANISM: Artificial sequence
<220> FEATURE:
<223> OTHER INFORMATION: PCR primer for potato nitrite reductase
<220> FEATURE:
<221> NAME/KEY: misc_feature
<222> LOCATION: (1)..(29)
<223> OTHER INFORMATION: attB2 sequence
<220> FEATURE:
<221> NAME/KEY: misc_feature
<222> LOCATION: (31)..(53)
<223> OTHER INFORMATION: sequence complementary to the potato cysteine
      synthase gene

<400> SEQUENCE: 78
ggggaccact ttgtacaaga aagctgggta atggcatctt tcatcaacaa tcc              53
```

METHOD FOR CHANGING THE DEVELOPMENT PATTERN, INCREASING THE GROWTH AND THE ACCUMULATION OF STARCH, CHANGING THE STRUCTURE OF STARCH AND INCREASING THE RESISTANCE TO WATER STRESS IN PLANTS

TECHNICAL FIELD

The invention relates to a method for increasing the growth of plants, causing an increase in its biomass, its robustness, the amount of starch accumulated and the number of flowers and branches with respect to the plants grown in normal conditions. This method further allows reducing flowering, increasing the size of the starch granule, changing the amylose/amylopectin balance and the degree of starch branching, increasing the amount of starch granule-associated proteins and even increasing the amount of chlorophyll accumulated and increasing the plant resistance to stressful conditions such as water stress. Additionally, the invention also relates to a method for increasing the amount of starch accumulated in leaves separated from the plants.

BACKGROUND OF THE INVENTION

Plants perceive biotic stimuli by recognizing many different signaling compounds produced by the organisms with which they interact. Some of these substances have pathogen-associated molecular patterns generally acting as the triggers of defense reactions. They are perceived at low concentrations and comprise different structures including carbohydrates, proteins, glycoproteins, peptides, lipids and sterols (Hahlbrock et al. 2003: Proc Natl. Acad. Sci. USA 100 (supl 2), 14569-14576).

Microorganisms also synthesize and emit many volatile compounds with molecular weights less than 300 Da, low polarity, and a high vapor pressure (Schóller et al. 2002: J. Agrie. Food Chem. 50, 2615-2621; Schultz and Dickschat 2007: Nat. Prod. Rep. 24, 814-842; Splivallo et al. 2007a: Phytochemistry 68, 2584-2598). The contact with microorganisms or the plant defense reaction triggering agents does not only affect said defense reactions, but, very often, lead to photosynthesis reduction, and a transition from the source state (in which digestible organic compounds are produced) to the sink state (in which said digestible compounds are imported from tissues in which they are stored) (as a review, see Berger et al. 2007: J. Exp. Bot. 58, 4019-4026). An indication of the sink state in infected leaves is the up-regulation of the cell wall invertase, which results in the reduction of sucrose exportation from the infected leaf to other parts of the plant. In some cases, saccharolytic enzyme sucrose synthase (SuSy) is up-regulated after contacting microorganisms, which can serve to distribute the sucrose to the callus deposition and promote the biosynthesis of cell wall polysaccharides in the infection sites (Essmann et al. 2008: Plant Signaling & Behavior 3, 885-887). The contact with pathogens can also result in the down-regulation of genes involved in starch metabolism (Cartieaux et al. 2008: Mol. Plant-Microbe Interact. 21, 244-259; Fabro et al. 2008: Plant Physiol. 146, 1421-1439), which can make simple sugars available to the pathogen in the infection sites. These branched homoplysaccharides are synthesized by starch/glycogen synthase using ADPglucose (ADPG) as sugar donating molecule.

Starch and glycogen are the main storage carbohydrates in plants and bacteria, respectively, their mechanisms relate closely to that of amino acids by mechanisms which are still poorly understood. In *Escherichia coli*, amino acid deprivation triggers the response to stringent conditions, a pleiotropic physiological change switching the cell from a growth related mode to a maintenance/survival/biosynthesis mode. In conditions with limited nutrient (amino acids) supply, cell division stops and the demand for ATP-dependent proteins drops and in the nucleic acid synthesis and degradation. Excess ATP is then diverted from nucleic acid/protein metabolism towards glycogen biosynthesis if it is present in the medium with excessive carbon sources (Eydallin et al., 2007b: FEBS Lett 581, 2947-2953; Montero et al. 2009: Biochem. J. 424, 129-141). The typical sign of this pleiotropic physiological response is the accumulation of alarmone guanosine 5'-diphosphate 3'-diphosphate (ppGpp), a nucleotide which binds to the bacterial RNA polymerase to stimulate the expression of genes (included those involved in the metabolism of glycogen) expressed at the start of the stationary phase. The levels of ppGpp are controlled by RelA (a ppGpp synthase) and SpoT (a bi-functional enzyme showing ppGpp synthase and hydrolase activity) (Potrykus and Cashel 2008: Annu. Rev. Microbiol. 62, 35-51). *E. coli* mutants with damaged relA function, and the cells over-expressing spoT show a glycogen-deficient phenotype (Montero et al. 2009: Biochem. J. 424, 129-141). In contrast, *E. coli* mutants with damaged amino acid synthesis such as cysteine synthesis show a glycogen-excess phenotype as a result of the stringent response (Eydallin et al., 2007b: FEBS Left 581, 2947-2953). These mutants show a normal glycogen phenotype when they are cultured in medium supplemented with cysteine, which points to the existence of close connections between the metabolisms of sulfur, nitrogen and carbon.

Recent studies have shown that plants have a ppGpp-mediated regulating system similar to that in bacteria, which has been shown to play a crucial role in aspects such as plant fertility. ppGpp accumulates in the chloroplast of stressed leaves through the regulation of homologs RelA/SpoT (RSH) expression (Takahashi et al. 2004 Proc. Natl. Acad. Sci. USA 101, 4320-4324).

Starch degradation in plants is mainly hydrolytic, α-amylases and β-amylases playing important roles in endosperm and leafy cereals starch degradation, respectively (Scheidig et al. 2002: Plant J. 30, 581-591; Fulton et al. 2008: Plant Cell 20, 1040-1058) unlike in bacteria, where glycogen degradation occurs through the phosphorolytic pathway. From the initial demonstration that ADPG serves as precursor molecule for the biosynthesis of both bacterial glycogen and plant starch, the consideration that ADPG pyrophosphorylase (AGP) is the only enzyme catalyzing ADPG production has been rather widespread. The genetic evidence that bacterial glycogen biosynthesis occurs only through the AGP pathway (GlgC) has been obtained with glgC mutants. However, recent studies have shown that these mutants accumulate substantial amounts of glycogen and a normal content of ADPG. Furthermore, evidence has been provided demonstrating the existence of various important ADPG sources, different from GlgC, linked to the glycogen biosynthesis in different bacterial species.

Starch biosynthesis in leaves has generally been considered as occurring exclusively in chloroplast, and is segregated from the sucrose biosynthetic process occurring in cytosol (FIG. 1A). According to this classic view, starch is considered the end product of a unidirectional pathway in which AGP exclusively catalyzes ADPG synthesis, and works as the main regulating step of the starch biosynthetic process (Neuhaus et al. 2005: Trends Plant Sci. 10, 154-156;

Streb et al. 2009: Plant Physiol. 151, 1769-1772). However, recent evidence has indicated the existence of an additional pathway in which ADPG linked to starch biosynthesis is produced de novo in the cytosol by means of SuSy. The sucrolytic enzyme SuSy is the main determinant of the sink strength intensively controlling the channelling of incoming sucrose towards starch and cell wall polysaccharides (Amor et al. 1995: Proc. Natl. Acad. Sci. USA 92, 9353-9357). It catalyzes the reversible conversion of sucrose and a nucleoside diphosphate into the corresponding nucleoside diphosphate glucose and fructose. Although UDP is the preferred nucleoside diphosphate substrate so that SuSy produces UDPG, ADP also acts as an accepting molecule effective for producing ADPG.

According to this alternative view, both the sucrose and starch biosynthetic pathways closely interconnected by means of SuSy ADPG-producing activity (Muñoz et al., 2006: Plant Cell Physiol. 46, 1366-1376; Baroja-Fernández et al., 2009: Plant Cell Physiol. 50, 1651-1662), and by means of the action of a still to be identified ADPG translocator located in the membrane enveloping the chloroplasts. The "alternative" view of the starch biosynthesis in the leaves illustrated in FIG. 1B also assumes that both plastidial phosphoglucomutase and the AGP play an important role in removing glucose units derived from starch degradation.

Most of the studies on the plant-microorganism interactions have been carried out in conditions with physical contact between the host plant and the microorganism. However, little is known on how microbial volatile emissions can affect plant physiology in the absence of physical contact. However what is known is that microorganisms such as *Pseudomonas* spp., *Streptomyces* spp., *Botrytis cinérea* and different truffles produce ethylene (Splivallo et al. 2007b: New Phytologist 175, 417-424), a gaseous plant hormone which plays important roles in several aspects of plant growth and development, including seed germination, hypocotyl elongation, start of root hairiness, leaf and flower senescence, fruit ripening, starch accumulation, etc. Splivallo et al. (Splivallo et al. 2009: Plant Physiol. 150, 2018-2029) only recently provided evidence that the ethylene produced by truffles induces changes in *Arabidopsis* plant development, which are presumably accompanied by significant metabolism changes.

Regarding bacteria, the scarce work in which the effect of microbial volatiles on plant growth is described revolve around a limited number of specialized strains of plant growth promoting rhizobacteria (PGPR). Certain symbiotic bacteria existing in the ground and colonizing plant roots are called rhizobacteria. Most of the strains the culturing of which results in a positive effect on the growth of plants cultured in its presence, without the need of physical contact, belongs to the *Bacillus* genus or to the genus which is closely related to *Bacillus*, the *Paenibacillus*, to which bacteria belong which in the past were classified as belonging to the genus *Bacillus*. Therefore, it has been shown that volatiles emitted by rhizobacteria from strains belonging to the species *Bacillus subtilis, Bacillus amyloliquefaciens* or *Bacillus cepacia*, for example, promote *Arabidopsis* plant growth, facilitating nutrient uptake, photosynthesis and defense response, and reducing glucose sensitivity and the levels of abscisic acid (Ryu et al. 2003: Proc. Natl. Acad. Sci. USA 100, 4927-4932; Ryu et al. 2004: Plant Phylio 134, 1017-1026; Vespermann et al. 2007; Appl. Environ. Microbiol. 73, 5639-5641, Xie et al. 2009: Plant Signal. Behav. 10, 948-953). Specifically, Ryu et al. (Ryu et al. 2003: Proc. Natl. Acad. Sci. USA 100, 4927-4932) describe an increase in *Arabidopsis thaliana* seedling growth triggered by the organic volatiles released by specific PGPR strains, specifically *Bacillus subtilis* GB03 and *Bacillus amyloliquefaciens* IN937a, further commenting that their data demonstrate that the release of volatile organic compounds is not the common growth stimulation mechanism of all rhizobacteria. Since they are cultured in the amino acid-rich medium trypticase soy agar, both bacteria release 3-hydroxy-2-butanone(acetoin) and 2,3-butanediol, compounds not emitted by other tested PGPR the volatiles of which did not affect *Arabidopsis* growth, but which are also released by other bacterial strains for which capacity of increasing the germination and growth of plants such as *Brassica olerácea* without there being physical contact between plant and bacteria has been detected, such as the case of the *Bacillus subtilis* strain WG6-14 object of patent application US 2008/0152684 A1. However, there are many bacteria releasing these substances (some belonging to the *Bacillus* genus) which do not promote plant growth. As well as the mentioned GB03 and IN937a strains of the *Bacillus* genus, Ryu et al. only mention that the growth increase effect due to the release of volatiles will be detected for another one of the tested bacteria, *Enterobacter cloacae* JM22, although no data corroborating this result is shown nor the profile of volatile emitted by this bacterium is mentioned. Furthermore, an earlier article from the same research group (Ryu et al. 2004: Plant Phylio 134, 1017-1026) shows significant differences between the high capacity of the volatiles emitted by the two *Bacillus* strains for protecting the *Arabidopisis thaliana* plants from the effect of the pathogen *Erwinia carotovora* and the limited protective effect of the volatiles emitted by *Enterobacter cloacae* JM22.

Other strains of the *Bacillus* or *Paenibacillus* genera emitting volatiles capable of promoting the growth of different plants also have been described but, in these cases, the effect seems to be linked mainly to the capacity of controlling the growth of pathogens which are affecting the plant. This is the case, for example, of the *bacillus* Kyu-W63 described in Japanese Patent JP 10033064, the volatiles of which are capable of controlling the pathopoiesis due to the presence of fungi of the *Cercospora* genus in cucumber leaves, facilitating plant growth therewith. The description suggests that the effect could be similar by using other filamentous bacteria, provided that the culture is produced in a sugar-rich medium such as the PDA agar, a medium which is not defined in more detail; neither is proof demonstrating the influence of the suggested medium or the applicability of the method for any other filamentous bacterium provided. The method for increasing plant growth, based on compositions comprising a volatile metabolite produced by a bacterium which is claimed in the Korean Patent Application KR20090066412 also simultaneously relates to inducing protection against diseases and insect attacks and to promoting the growth of different plants, monocotyledons and dicotyledons. Examples of possibly useful metabolites include 3-acetyl-1-propanol, 3-methyl-1-butanol, indole, isoamyl acetate and butyl acetate. The abstract mentioned that the possible microorganisms which produce a volatile metabolite with the desired effect comprise bacteria belonging to the *Bacillus* or *Paenibacillus* genera, a strain of the species *Paenibacillus polymyxa* being the preferred microorganism.

As has been mentioned above, in addition to activating the defense system and promoting growth it has also been detected that the volatile compounds emitted by some bacteria have other effects in the plants. Therefore, Zhang et al. (Zhang et al. 2008: The Plant Journal 56, 264-273), describe how exposing *Arabidopsis thaliana* plants to the volatiles emitted by *Bacillus subtilis* GB03, again cultured in the culture medium trypticase soy agar, suppress plant glucose sensitivity, simultaneously causing a slight increase in sugar accumulation and an increase in photosynthesis, the latter being a process which is normally inhibited when the levels of soluble sugars accumulated in the plants increase. The plants contacting the volatiles emitted by *B. subtilis* GB03 show increases of 50-62% of the soluble sugar content with respect to the control plants which accumulate approximately 2 micromoles of hexose per gram of fresh weight (cf. FIG. 2, Zhang et al. 2008: The Plant Journal 56, 264-273). The increase in the soluble sugar content is generally associated with a reduction of the intracellular starch levels (Caspar et al. (1985) Plant Physiol. 79:11-17; Jones et al. (1986) Plant Physiol. 81: 367-371; Lin et al. (1988) Plant Physiol. 86:1 131-1135; Neuhaus and Stitt (1990) Plant 182:445-454; Szydlowski et al. (2009) Plant Cell 21, 2443-2457). Therefore, it is foreseeable that, in the conditions used by Zhang et al., the plants contacting the volatiles emitted by *B. subtilis* GB03 accumulate little starch. The method used by the group of Zhang et al. only allows measuring the content of glucose, fructose, fructose-6-phosphate and glucose-6-phosphate, although not the accumulated starch, although the absence of variations in the expression levels of genes involved in starch metabolism such as starch synthase or starch degrading enzymes shown by transcriptomic analysis of chloroplast proteins in plants exposed to the volatile shown in Supplementary Table 1 do not seems to indicate that an increase in this storage polysaccharide was foreseeable as the plant is subjected to the effects of the volatiles emitted by *B. subtilis* GB03. This interpretation is supported by the fact that the tests relating to the inhibition of hypocotyl height and seed germination indicate that the volatiles of *B. subtilis* GB03 do not cause a metabolic response to the treatment, since they do not seem to affect sugar metabolism, but do affect the sensitivity to said compounds.

According to what is known until now, all these effects on the plants are not common to the volatiles emitted by any bacteria. Therefore, for example, as discussed above, the tests performed by Ryu et al. (Ryu et al. 2003: Proc. Natl. Acad. Sci. USA 100, 4927-4932) demonstrate that several strains of *Bacillus* species, such as *Bacillus pumilus* T4 or *Bacillus pasteurii* C-9, as well as bacteria belonging to other genera such as *Pseudomonas fluorescens* 89B-61 or *Serratia marcescens* 90-166, were not capable of increasing the growth of *Arabidopsis thaliana* plants subjected to the effect of the volatiles emitted by said bacteria, despite the fact of having been equally cultured in the same culture medium, rich in sugars and amino acids: the trypticase soy agar. Another bacterium included in the same test, *Escherichia coli* DH5a, was used in the same test as control, since it is known as a strain which does not increase the growth of plants subjected to the action of the volatiles emitted by it.

Furthermore, it has also been shown that the volatiles of bacteria such as *Pseudomonas* spp., *Serratia* spp. and *Stenotrophomonas* spp., and of some species of fungi exert inhibitory effects on *Arabidopsis* plant growth (Splivallo et al. 2007b: New Phytologist 175, 417-424, Tarkka and Piechulla 2007: New Phytologist 175, 381-383)

Due to the lack of knowledge about how the microbial volatiles can affect the reprogramming of the cell metabolism, particularly primary carbohydrate metabolism, today it is not possible to act on the plant metabolism with microbial volatiles to promote its growth, since the mechanisms involved in promoting or inhibiting microorganism-activated growth mentioned above, or the conditions in which one or another is activated or the possible differences among microorganisms producing one effect or another are not clear. However, it would be interesting to know these mechanisms to enable designing a method for activating plant growth and/or flowering, and increasing the growth, biological and mechanical resistance thereof by means of using microbial volatiles and, preferably, for increasing starch synthesis in plants, since it is a product of great interest today in some industries. It would be particularly interesting for the method to be applicable to every type of plant and/or, particularly, to plants of agricultural interest in general, and which would be easy to apply. The present invention provides a solution to this problem.

DESCRIPTION OF THE INVENTION

The invention is based on the surprising discovery that, as plants grow in the presence of any type of microorganism (gram-positive or gram-negative bacteria, yeasts or fungi), without there being any contact between the plant and the microorganism, the volatiles emitted by the microorganism result in a change in the development pattern and an increase in growth, fertility, dry weight and starch accumulation of the plants. Furthermore, the exposure to such volatiles induces the accumulation of a starch with structural characteristics different from those of the starch accumulated by plants not exposed to the volatiles, both in terms of that relating to the structure of the starch molecule itself and to size of the accumulation granules. These effects are observed both in monocotyledon and dicotyledon plants {*Arabidopsis*, maize, barley, tobacco, potato, pepper . . . ), and are independent of whether or not the microorganism is a pathogen for the plant and whether it belongs or does not belong to a species that does not co-exist with the plant in natural conditions. These effects are observed both if the plants are cultured in vitro and on soil, provided that the plant is cultured in the presence of a microorganism culture emitting volatiles or in the presence of the microbial volatiles emitted by the microorganism. These seem to be responsible for the observed effects. Therefore, although there is no physical contact between the plant and the microorganism, the latter must be close enough to the plant so that the volatile compounds emitted by the microorganism do contact the plant and can exert their effect thereon.

Growth increase can be apparent in an increase in plant length, in an increase in leaves, in an increase in stem thickness and/or in an increase in root size. It should be highlighted that, as can be seen below in the examples of the present application, the effect of the presence of fungal volatiles on pepper plant root development is spectacular.

The change of growth pattern can be shown in an increase in the number of leaves, an increase in the number of branches, an increase in the number of flower buds, flowers and seeds of angiosperm plants, flowering induction or combinations of the above.

This effect has been observed with all kinds of microorganisms and, particularly in the case of studies conducted on leaves, it seems to be the consequence of a transition from the source state to the sink state. Therefore, the results presented in the present application show that the volatile emissions from all microbial species analyzed promoted a plant biomass increase and led to the accumulation of high starch content, in comparison with the control plants grown in the same conditions, except for the absence of the microorganism culture. The effect observed is independent of the presence of sucrose in the culture medium and is strongly suppressed by cysteine supplementation. The effect occurs both in monocotyledon and dicotyledon plants. This occurs not only for volatiles emitted by rhizobacteria plant growth promoters such as certain volatiles isolated from *Bacillus subtilis*, but surprisingly also for the volatiles emitted for different fungal plant pathogens and bacteria from species such as *E. coli* or *Pseudomonas* spp., and they contradict the results obtained previously with said species and some species of fungi in which the opposite effect had been observed, their volatiles inhibiting the growth of plants cultured in their presence). Thus, the present invention demonstrates that the capacity of emitting volatiles positively influencing plant biomass in general and its growth in particular is not restricted to rhizobacteria, provided that the microorganism is cultured in the suitable medium. The positive effect on growth and starch accumulation is especially observed when the microorganism is cultured in a minimal medium (such medium is understood as a medium lacking amino acids but containing various salts, which may vary according to the species of microorganism and the conditions of growth, which are those that provides essential elements such as magnesium, nitrogen, phosphorus and sulfur so that the microorganism can synthesize proteins and nucleic acids) supplemented with an organic carbon source (generally, a sugar, such as glucose or sucrose). It seems that the use of such medium prevents the microorganisms from generating volatile ammonium from amino acids or other organic nitrogen sources present in amino acid-rich media such as those used in tests in which other authors have observed growth inhibition by microbial volatiles (such as LB medium or Kornberg medium), and this difference seems to be the reason causing the culture of plants in the presence of microorganisms with which they contact to result in an increase in growth, flowering, branching, fertility, robustness, biomass in general and in starch accumulation in particular. In fact, the present application discloses tests in which it is shown that the ammonium, when the plants are cultured in an atmosphere in which said compound is present, is responsible for plant depigmentation and growth inhibition. This result reinforces the idea that the microorganisms cultured in amino acid-rich media (and generally with organic compounds which have amino groups), produce growth-inhibitory volatiles (ammonium); such compounds, however, are not produced when the microorganisms are cultured in minimal medium such as M9 or MOPS which lack amino acids.

When the plants grow in the presence of microbial volatiles not only changes related to growth, development pattern or starch accumulation are observed, but, as shown below in the examples of the present application, the growth increase and the change of development pattern observed when the plants grow in the presence of microbial volatiles are accompanied by an increase in the amount of chlorophyll.

Furthermore, the data provided in the present patent application demonstrates that plant growth in the presence of microbial volatiles has another effect: the increase in the plant resistance to water stress. It is observed that if *Arabidopsis thaliana* plants are grown in a culture medium in which the amount of water is less than that which would be suitable for an optimum growth, the growth of the plants growing in the presence of microbial volatiles (specifically, fungal volatiles produced by *Alternaria alternata*) are less affected than the control plants growing in the absence of such microbial volatiles.

Water stress is the situation occurring in plants during drought, i.e., when the water available in the soil is insufficient and it causes difficulties for the plant to absorb water from the ground. Plant water absorbing capacity is determined by the so-called water potential, $\Psi w$, which is determined by the osmotic potential, the wall potential, the matrix potential and the gravitational force. Water potential defines plant difficulty in obtaining water. A mechanism for resisting stress due to water deficiency is reducing the osmotic pressure and keeping the wall pressure, i.e., the cell turgescen constant, whereby the water potential drops which, if it is less than that of the dry ground, will allow the plant to capture water.

It is know that one of the main effects of water stress is the reduction of cell growth. Plant tissue growth is caused by the division and elongation of cellular components, resulting in adaptive forms of the plants. In this context, the loss of turgor pressure as a consequence of water content imbalance can result in reduced growth or the complete absence of growth under dry ground conditions. Furthermore, plants under water stress have a lower transpiration capacity because they close their stomas preventing water losses through same, but also complicating the passage of $CO_2$, which is one of the reasons of photosynthesis reduction.

The latter is the first occasion in which it is reported that microbial volatiles are capable of inducing growth, flowering, branching, starch accumulation, as well as structural change of this polymer in the plants growing under their effect and that they are even capable of causing an increase in chlorophyll accumulation and an increase in plant resistance to water stress. Therefore, the authors of the invention seem to have found the culture conditions allowing any type of microorganism (may or may not be pathogen for the plant) to release a mixture of volatiles capable of exerting a positive effect both on growth, flowering, branching and on starch accumulation, as well as a positive effect on that relating to the resistance to water stress and to chlorophyll accumulation.

The results obtained by the authors of the invention further contradict some previous ideas with respect to the culture medium to be used so that a bacterium produces the volatiles suitable for promoting the growth of plants cultured in the presence of said volatiles, such as the idea which seems to be suggested by the Japanese patent JP 10033064 that culturing in a sugar-rich medium may be sufficient for some bacteria to emit a mixture of volatiles capable of inducing the growth of plants and protect them against pathogens. Therefore, the tests described below in the examples of the present application show that volatiles emitted by bacteria and other microorganisms, grown in LB with 50 mM glucose exert a negative effect not only on growth, but also on starch accumulation in plants contacting said volatiles.

The increase in the amount of accumulated starch is observed in different organs of the plant: leaves (not only when they are attached to the whole plant, but also in leaves detached from the plant, located in the presence of volatiles emitted by microorganisms of different species); roots; stems; tubers (in which the amount of accumulated starch, for example in potato plants, is greater than that accumulated in control plants . . . ).

The discovery that the microbial volatiles induce the over-starch accumulation in leaves and other organs of the plant forms a mechanism which has not been reported previously, establishing an additional function for the volatiles such as signaling molecules mediating the plant-microorganism interactions and aiding the elucidation of the plant carbohydrate metabolism induction process by means of microorganisms. The increase in the amount of accumulated starch also seems to be accompanied by structural changes of the starch, both in that relating to the biopolymer structure and granule structure. Therefore, on one hand it is observed that the starch granules are larger than those of the control plants cultured in the absence of volatiles. This is a rather important feature since the size of the starch granule has great importance at industrial level due to being an important determinant of the physicochemical properties of the starch granule suspension, such that the size and form differences of the starch granules of species such as potato, wheat, maize, etc., is what largely determines that these starches have different industrial applications. Furthermore, it is observed that the starch accumulated by the plants growing in atmospheres containing microbial volatiles have a significant reduction in relative amylose content, whereby the amylose/amylopectin ratio is less than that of the control plants. This modification in the structure of the starch molecule is accompanied by changes in the amylopectin chain degree of polymerization, which is lower in the plants treated with microbial volatiles. Furthermore, the tests conducted with the green fluorescent protein (GFP) bound to the granule-bound starch synthase (GBSS) confirm that the plants growing in the presence of microbial volatiles not only accumulate more amount of starch, but this increase is accompanied by an increase in the amount of starch granule-bound proteins in said plants. Therefore, plant culture in atmospheres containing volatiles emitted by microorganisms allows obtaining plants which do not only have a higher starch production but also result in a starch the characteristics of which allow industrial applications different from those of the starch synthesized by the plants cultured in the absence of volatiles.

The authors of the present invention have gone a step further and have attempted to elucidate if, among all the volatiles emitted by the different microorganisms, there are volatiles responsible, for example, for the effect of growth increase in plants, and other volatiles responsible for other effects, such as the effect of the increase in the starch accumulated by thereof or if both effects were due to the same volatiles. The present invention presents tests demonstrating that not all the volatiles produced by the microorganisms are capable of influencing the increase in biomass and starch accumulation observed in plants growing in atmospheres in which said volatiles are present. Said tests further demonstrate that some volatiles which were known in the state of the art as compounds capable of promoting plant growth do not affect the starch content accumulated by thereof. However, other volatile compounds, such as propanoic acid, acetic acid, acetaldehyde, formic acid and butyric acid are identified (which are compounds produced, for example, by several species of bacteria), which have a positive effect on starch accumulation, and which also seem to have effect on growth, biomass and flower induction: that is the case, for example, of formic acid, for which tests demonstrating its capacity of increasing starch accumulation and also plant growth are shown. Furthermore, data indicating that its effect is dose-dependent is also provided.

The identification of specific volatile compounds having positive effects on growth and starch accumulation has several points of interest. On one hand, it corroborates the usefulness of certain known specific microorganism cultures, producers of one or several of the mentioned volatiles, to cause an increase in growth and/or starch accumulation when the plants grow in the presence of a culture of said microorganisms, without there being contact between the plants and said cultures. These microorganisms can include:

Formic acid and acetic acid producing microorganisms:
Escherichia coli. These two substances are two of the products produced by E. coli in mix acid fermentation (Clark D P 1989: FEMS Microbiol Rev. 5(3), 223-234 (review); Maupin et al. 1990: J Bacteriol. 172(9): 4798-4806).

Acetaldehyde producing microorganisms:
Escherichia coli. Normally, E. coli does not produce acetaldehyde, although practical work describing acetaldehyde-producing lineages can be found (Salaspuro et al. 1999: Scand J Gastroenterol. 34(19), 967-973.

Butyric acid-accumulating bacteria:
Some species of the Clostridium and Butyrivibrio genera, as well as Porphyromonas gingivalis, Prevotella loescheii and Fusobacterium nucleatum (Kopecn et al. 2003: Int J Syst Evol Microbiol 53, 201-209; Zhu et al. 2005: Biotechnol Bioeng 90(2), 154-166; David White: "The physiology and biochemistry of prokaryotes", 2nd edition, Oxford University Press).

Propanoic acid-accumulating bacteria: Some species of the Clostridium and Propionibacterium genera, as well as Porphyromonas gingivalis, Prevotella loescheii and Fusobacterium nucleatum (Leaver et al. 1955: J Bacteriol 70(5):521-30; Jin et al., 1998: Biotechnol Prog. 14(3):457-465; David White: "The physiology and biochemistry of prokaryotes", 2nd edition, Oxford University Press).

Multiple volatile compounds-producing bacteria:
Actinomycetes produce more than 120 volatile compounds, including some from the formic acid, acetic acid, propanoic acid and butyric acid and acetaldehyde group, and some alcohols, esters, ketones, isoprenes, etc. (Scholler et al., 2002: J. Agrie. Food Chem. 50, 2615-2621).

Myxococcus xanthus is also a good volatile producer (Dicjschat et al., 2004: Chem. Biol. Chem. 5, 778-787).

A summary of all known volatile compounds (346) emitted by bacteria can found in Schulz et al., 2007: Nat. Prod. Rep. 24, 814-842).

In addition, the knowledge of volatile compounds resulting in a plant growth increase and/or an increase in starch accumulation allows obtaining said effects without needing the presence of a microorganism culture in the plant culture site, but it is possible to choose one or more volatile compounds which are known to have the desired effect and provoke its presence in the culture atmosphere by various means from the evaporation of a solution present in the plant culture site or insufflating an atmosphere already containing the compound or volatile compounds to the culture site from the outside thereof as part of the insufflated atmosphere, or in that the volatile compound itself is administered to the atmosphere of the plant culture site from the outside.

With respect to the metabolic changes resulting in the observed effects, particularly in the increase starch accumulation, the transcriptomic analyses of, among others, leaves of potato plants exposed to fungal volatiles (specifically, produced by fungi of the genus Alternaria) have revealed that the changes in starch metabolism are accompanied by changes in multiple biological processes and in the activity or expression of different enzymes, such as:

the up-regulation of: sucrose synthase, invertase inhibitors, starch synthase Class IV, starch branching enzyme, proteins involved in endocytosis and vesicle trafficking, glucose-6-phosphate transporter from the stroma to the cytosol, and enzymes involved in glycolytic, respiratory and fermentative pathways;

the down-regulation of: acid invertase, plastidial thioredoxins, starch degradation enzymes, proteins involved in plastidial triose-phosphate to cytosolic glucose-6-phosphate conversion, proteins involved in internal amino acid provision such as nitrite reductase, plastidial glyceraldehyde-3-phosphate dehydrogenase, cysteine synthase, plastidial glucose-6-phosphate dehydrogenase, etc. . . .

FIG. 21 illustrates a suggested metabolic model for the process triggered by the microbial volatiles deduced from the studies conducted in leaves of potato plants which are described below in the examples of the present application, comprising variation studies both in enzymatic activities and transcriptomic activity, as well as analysis by means of RT-PCR of the levels of different specific transcripts particularly related to the metabolism of N, C and S.

As discussed in the examples which are shown below in the present specification, the up-regulation of sucrose synthase (SuSy) seems to be one of the determining factors of starch accumulation in plants subjected to the effect of microbial volatiles. But the effects observed on other enzymes, particularly the reduction of cysteine synthase, the reduction of nitrite reductase, the reduction of plastidial glyceraldehyde-3-phosphate dehydrogenase, the reduction of plastidial glucose-6-phosphate dehydrogenase, the over-expression of glucose-6-phosphate translocator and the over-expression of protease inhibitor, alone or combined with one another, seem to be capable of increasing the starch content without the need of an increase in sucrose synthase activity.

The tests shown in the examples of the present application also provide data supporting an involvement of allosteric activation of ADPglucose pyrophosphorylase in the increase in starch accumulation caused by the presence of microbial volatiles in the culture atmosphere. Therefore, data demonstrating that the 3-PGA/Pi ratio (3-phosphoglyceric acid ratio with respect to orthophosphate) increases in the case of plants cultured in the presence of light and fungal volatiles in the culture atmosphere is provided, there also seems to be a ratio between the increase in starch and the increase in time of the value obtained in that ratio.

The authors of the present invention have complemented the knowledge about the mechanisms by means of which the effects which are observed in plants are produced when the same are grown in the presence of microbial volatiles, as well as of the factors controlling them, defining the most suitable plants for carrying out the method of the invention, as well as the most ideal type of light for it. Therefore, on one hand, examples are provided in which it is shown that the increase in starch accumulation shown by plants growing in the presence of microbial volatiles is controlled by light, since mutants with active phytochrome and cryptochrome deficiencies accumulate less starch than wild-type plants, therefore mutants with active phytochrome and cryptochrome deficiencies can be considered as less efficient for applying the aspect of the method of the invention relating to the increase in starch accumulation in plants. Other gene deficiencies also influence starch accumulation: therefore, plants with NTRC deficiency, as well as plants with soluble starch synthase deficiency SSIV and/or SSIII, accumulate less starch, in the presence of microbial volatiles, than wild-type plants which demonstrates the significant role of these genes in increasing starch accumulation when the plants grow in the presence of microbial volatiles in the atmosphere. Furthermore, the involvement of β-amylase in controlling starch accumulation is confirmed, since (a) the mutants with BAM4 and SEX1 deficiencies accumulate more starch than the wild-type plants also grown in the presence of microbial volatiles and (b) the wild plants accumulate maltose when they are subjected to the action of microbial volatiles. Lastly, a greater knowledge on the influence of light is provided, since it is shown that starch accumulation under blue light, or the far-red light, is less than under white or red light, which indicates that if higher yields are to be obtained in the starch accumulation method of the invention, it will be advisable to use white or red light, light having the wavelength corresponding to the blue region or the far-red region being advisable if the starch accumulation is desired to be greater than that of plants growing in the absence of microbial volatiles, but in a smaller magnitude than that observed under the action of white light.

All these findings open the door for considering methods for increasing the growth of plants and/or their starch production by means of culturing them in the presence of microorganisms producing volatiles, without there being contact between them, or by means of culturing the plants in the presence of the mixture of volatiles produced by the microorganism previously cultured in a space different from that of plant growth. Therefore, it opens up the possibility of increasing the productivity of plants cultured, for example, in greenhouses, co-culturing therewith volatile compound-emitting microorganisms; alternatively, the plants could contact the volatiles because the volatiles will be applied directly to the greenhouses, after having cultured the microorganisms in large reactors, in the suitable media (in general, minimal medium such as M9, MOPS, Murashige&Skoog (MS) etc.). Applying the volatiles produced by previously cultured microorganisms to the culture atmosphere could be performed by applying them by means of techniques of great agronomic interest, such as fumigating or spraying; it would further enable performing the administration thereof to the plant culture atmosphere together with other compounds of interest, such as fertilizers or pesticides. Another possible alternative is to supply the volatile compounds produced by any microorganism together with the irrigation water, volatiles which will evaporate from the irrigation water into the plant culture atmosphere and produce therein the effects which would be observed if the plant is cultured in the presence of a microorganism culture that produces those exact volatiles: the tests shown below in the examples of the present application, in which the plants are irrigated with a filtered culture medium of *Alternaria alternata*, demonstrate the validity of this second alternative. These alternatives include the possibility of supplying, to the plant culture atmosphere, one or more specific volatiles, selected from those which are produced by microorganism cultures, for which the fact that they have a positive effect on plant growth and/or starch accumulation are known, such as formic acid, acetic acid, propanoic acid or butyric acid or acetaldehyde; said compounds can be administered to the culture atmosphere, for example, by insufflating them therein or allowing their evaporation from a solution containing them present in the plant culture sites, which solution can be the irrigation water itself. These specific compounds could be introduced in the culture atmosphere by applying them by means of techniques of great agronomic interest, such as fumigating or spraying, such as in the case of applying the mixture of volatiles produced by previously cultured microorganisms to the culture atmosphere, which again would further facilitate performing the administration thereof to the plant culture atmosphere together with other compounds of interest, such as fertilizers or pesticides.

Furthermore, the fact that the leaves accumulate more starch in the presence of microorganisms producing volatiles, even when said leaves are separated from the plant, allows designing an alternative mechanism for obtaining starch in which leaves detached from plants are used, which can be the waste products from the processing thereof. Enzyme elucidation in the activity/expression of which changes occur promoting starch accumulation allow increasing starch accumulation by means of alternative methods, based on the same inventive principle, in which the changes in specific enzymes occur in the plant due to the fact of using transgenic plants which over-express the gene or genes of interest or in which an inhibitor thereof is expressed, the activity of which drops due to the presence of the microbial volatiles.

In addition, the fact that the leaves separated from the whole plant are also capable of producing starch, when they are kept in the presence of microorganism cultures producing volatiles, is very important from the industrial viewpoint. In a matter of 2-3 days, the leaves are capable of producing large amounts of starch with only 4 ingredients, which could be considered as "cheap": a little water, natural $CO_2$, natural light and microbial volatiles. It can be considered that the leaf would act as a starch producing bio-factory powered by solar light. In addition to the interest that the starch produced could be advantageous to the starch industry, the advantage involving the ability to use leaves separated from the whole plants must be taken into account, since the rests of the prunings which are normally destroyed (for example, potato leaves), could be used for producing a type of starch of industrial interest.

Therefore, the invention relates to a method for increasing the size of a plant, its development pattern (including characteristics relating to its fertility, the biomass in general and starch in particular by growing thereof in the presence of volatiles emitted by a microorganism, microorganism which can be cultured in the same space as the plant, so that the plant contacts therewith due to the fact that the microorganism releases said volatiles to the atmosphere in which the plant is growing, or that the volatiles may have previously been collected and artificially added to the plant growth atmosphere.

Therefore, an object of the present invention is a method for increasing the growth of a plant and/or changing its development pattern, characterized in that the plant is cultured in the presence of a volatile compound-producing microorganism, without there being any contact between the plant and the microorganism, or in the presence of the volatiles emitted by the microorganism, in which the microorganism is different from the isolated *Bacillus subtilis* GB03 and *Bacillus amyloliquefaciens* IN937. The growth increase in the plant can be shown in an increase in the size (in length) of the plant and increase in the size of leaves. In terms of the change of development pattern, it can be shown as an increase in the number of leaves, an increase in the number of branches or as effects more closely related to fertility, such as an increase in the number of flowers and seeds of angiosperm plants, and/or flower induction, or in combinations of the above effects.

The microorganism can be a bacterium, a yeast or a microscopic multicellular fungus. When the microorganism is chosen from bacteria, it can be chosen from a genus different from *Bacillus* or *Paenibacillus*, which are the genera to which the specific strains of rhizobacteria belong in which a positive effect of the volatile emissions thereof on plant growth has previously been detected when grown in very rich media.

Given that the specific volatile compounds the presence of which in the atmosphere in which the plant grows also results in a growth increase in the plant and/or the change of its development pattern, also being capable of producing an increase in the starch accumulated in the whole plant has also been identified, another aspect of the invention relates to a method for increasing the growth of a plant and/or changing its development pattern characterized in that the plant is cultured in an atmosphere in which at least one volatile compound is present which is selected from propanoic acid, acetic acid, acetaldehyde, formic acid and butyric acid. Among them, formic acid is preferred. In a possible embodiment of this aspect of the improvements of the invention, the volatile compound is present in the atmosphere through evaporation from a solution containing it which is in the plant culture site, which solution can be, for example, the irrigation water of the plant. In another possible embodiment the volatile compound is supplied to the culture atmosphere; the possibilities for performing thereof include: the possibility of insufflating the volatile compound to the culture atmosphere (a particularly interesting possibility if the plant is cultured in a greenhouse); application by means of fumigating or spraying. Whatever the method of application to the culture atmosphere is, it is preferably performed together with one or more compounds of interest, such as a fertilizer, a pesticide, or mixtures thereof. In any of the cases, like the variant of the method which is carried out with an atmosphere containing the mixture of volatiles produced by a microorganism, cultured or not cultured in the same site as the plant, without there being any physical contact therebetween, the growth increase can be shown in an increase in length of the plant and/or in an increase in the size of the leaves, and the change of the growth pattern can be shown in an increase in the number of leaves, an increase in the number of branches and/or in the number of flowers and seeds of angiosperm plants, flower induction, or combinations of the above Due to the effect observed, specifically on the increase in starch accumulation, another object of the invention is a method for increasing starch production of a plant, characterized in that the plant is cultured in the presence of a volatile compound-producing microorganism, without there being any contact between the plant and the microorganism, or in the presence of the volatiles emitted by the microorganism. Furthermore, particularly, the starch produced preferably has modifications with respect to the normal plant structure, which can refer to both the increase in size of the starch granules and the structure of the starch molecule itself, specifically, in a reduction of amylose/amylopectin ratio (which, as has been mentioned previously, drops with respect to the ratio found in the control plants, due to a significant reduction in the relative amylose content), and in the reduction of amylopectin chain degree of polymerization, which is less in the plants treated with microbial volatiles with respect to that observed in the control plants, such as shown below in the examples relating to the structural analysis of the starch obtained by growing the plants in the presence of microbial volatiles.

Given that the starch increase, as shown in the examples of the present application has been observed in different plant organs (leaves, stems, roots and tubers), those in which the increase in starch production occurs at least in one plant organ, preferably selected from leaf, stem, root, seeds or, in the plants having it, the tuber, are possible embodiments of the method for increasing the starch accumulation, preferably starch with a modified structure. Such as when a growth increase and/or the change of development pattern is sought, when the specific objective is starch accumulation, the plant can an angiosperm, monocotyledon or dicotyledon. Potato or maize plants are particularly preferred. Among the microorganisms, a possible option is the fungi of the *Alternaria* or *Penicillium* genera, the usefulness of which is shown below in the examples of the present application.

By taking advantage the knowledge acquired by the authors on the modifications in plant metabolism by means of which the microbial volatiles cause the increase in starch accumulation, an alternative to the method for increasing the starch accumulation consists of directly provoking the accumulation by means of using transgenic plants, based on the same inventive principle in which the expressed transgene or transgenes results in the over-expression of some of the up-regulated enzymes due to the exposure to the volatiles or consists of an activity or expression inhibitor (by means of interfering RNAs, for example) inhibiting some of the down-regulated enzymes. Therefore, an alternative aspect of the invention is a method for increasing starch production of a plant, characterized in that the plant is a transgenic plant in which at least one transgene is present the expression of which results in a product selected from the group of: a plant protease inhibitor (such as, for example, that having the GenBank accession number DQ 16832), starch branching enzyme, an acid invertase inhibitor (such as for example, that having the GenBank accession number FN691928), an antisense RNA directed against cysteine synthase (which can be deduced, for example, from the sequence corresponding to the cysteine synthase of the potato plant, with GenBank accession number AB029512), an antisense RNA directed against plastidial glyceraldehyde-3-phosphate dehydrogenase (such as for example, that having the GenBank accession number FN691929), an antisense RNA directed against plastidial glucose-6-phosphate dehydrogenase (which can be deduced, for example, from the sequence corresponding to the potato glucose-6-phosphate dehydrogenase, with GenBank accession number X83923) or an antisense RNA directed against nitrite reductase (such as for example, that having the GenBank accession number FN691930). Those in which the plant expresses at least one transgene are preferred embodiments the expression of which results in a product selected from the group of: plant protease inhibitor, an antisense RNA directed against cysteine synthase or an antisense RNA directed against nitrite reductase. In the latter, the coding sequences of the transgene can be derived, for example, from that corresponding to potato genome, i.e., the transgene can be a transgene that expresses protease inhibitor the coding sequence of which is represented by SEQ ID NO:67 (coding sequence which must be operatively bound to a promoter such that its expression occurs in the direction resulting in the natural protein) or in which the antisense RNA expressed by the transgene is directed against cysteine synthase the coding sequence of which is represented by SEQ ID NO:71 (coding sequence which must be operatively bound to a promoter such that its expression occurs in antisense) or against nitrite reductase the coding sequence of which is represented by SEQ ID NO:69 (coding sequence which, similarly to the case above, must be operatively bound to a promoter such that its expression occurs in antisense). Particularly the plant preferably expresses more than one transgene of any of those mentioned above and/or any embodiments in which the plant, in addition to one or more transgenes of one of the groups above, also has at least one transgene resulting in the ectopic expression of the enzyme sucrose synthase (SuSy) (such as a transgene expressing the potato enzyme, the mRNA of which has the GenBank accession number AJ537575) or the expression of the glucose-6-phosphate transporter (such as a transgene expressing the potato transporter, the coding sequence and promoter of which have the GenBank accession number AY163867).

Plasmids suitable for generating some of the transgenic plants mentioned in the paragraph above are also provided in the present application. Therefore, a possible embodiment of the aspect of the invention relating to a method for increasing starch production in a plant by means of using transgenic plants, where the embodiment is characterized in that the method includes a step in which a transgene is introduced in a plant by means of a plasmid comprising at least one sequence which is selected from those represented by SEQ ID NO:67 (proteinase inhibitor coding sequence, sequence which must be operatively bound to a promoter such that its expression occurs in the direction resulting in natural protein), SEQ ID NO:69 (nitrite reductase coding sequence, sequence which must be operatively bound to a promoter such that its expression occurs in antisense) and SEQ ID NO: 71 (coding sequence of cysteine synthase, sequence which must be operatively bound to a promoter such that its expression occurs in antisense). The plasmid can be used for biolistic transformation of the plants or by means of *Agrobacterium tumefaciens*. Particularly the plasmid preferably contains Tnos sequences. In another possible embodiment of the method for increasing starch accumulation by means of using transgenic plants, the coding sequence represented by SEQ ID NO:67, the sequence antisense to that represented by SEQ ID NO:69 or the sequence antisense to that represented by SEQ ID NO:71 is operatively bound to the constitutive promoter S35 of the cauliflower mosaic virus (CaMV). Preferably the plasmid comprises at least one selection marker, which can be an antibiotic resistance gene such as kanamycin, chloramphenicol, ampicillin, zeomycin or hygromycin and, more preferably, comprising at least two selection markers, such as, for example, a gene conferring kanamycin resistance and a gene conferring hygromycin resistance. A possible embodiment of the method for increasing the production by means of using transgenic plants would consist of using at least one of the plasmids the production process of which is described in example 16 of the present invention, i.e., a plasmid comprising the sequence represented by SEQ ID NO:67, the sequence antisense to that represented by SEQ ID NO:69 or the sequence antisense to that represented by SEQ ID NO:71, operatively bound to the promoter 35S of CaMV, which additionally comprises *Agrobacterium tumefaciens* Tnos sequences, a kanamycin resistance gene and a hygromycin resistance gene.

Another possible alternative for increasing the content of starch in a plant is by resorting to the presence of some of the specific volatiles in the atmosphere in which the plant grows, which can be produced by microorganisms, for those which are known to have that effect. Therefore, yet another aspect of the invention relates to a method for increasing the amount of starch accumulated in a plant, characterized in that the plant is cultured in an atmosphere in which at least one volatile compound is present which is selected from propanoic acid, acetic acid, acetaldehyde, formic acid and butyric acid. As in the case above, in a possible embodiment of this aspect of the invention, the volatile compound is present in the atmosphere through evaporation from a solution containing it which is in the plant culture site; within that possible embodiment, a possibility is that the solution is, for example, the irrigation water of the plant. In another possible embodiment the volatile compound is supplied to the culture atmosphere; the possibilities for performing thereof include: the possibility of insufflating the volatile compound to the culture atmosphere (a particularly interesting possibility if the plant is cultured in a greenhouse); application by means of fumigating or spraying. Whatever the method of application to the culture atmosphere is, it is preferably performed together with one or more compounds of interest, such as a fertilizer, a pesticide, or mixtures thereof.

In addition, the fact that the increase in the starch accumulated is also observed in leaves which are not part of whole plants, but separated therefrom, when the leaf is maintained together with a microorganism culture, allows contemplating yet another aspect of the invention. A method for obtaining starch from leaves of plants separated from same, comprising a step in which the leaves are kept in the presence (but without physical contact) of a microorganism culture or of the volatiles emitted by this microorganism would be the same. Once again the microorganism is preferably a bacterium, yeast or microscopic fungus which does not contact the plant in natural culture conditions. A possible preference is the fungi of the genera *Alternaria* or *Penicillium*, particularly when the leaves are potato leaves.

In another aspect, the present invention relates to a method for increasing the amount of starch-associated proteins in a plant, characterized in that the plant is cultured in the presence of a volatile compound-producing microorganism culture, without there being any contact between the plant and the microorganism, or in the presence of the volatiles emitted by the microorganism. This aspect has a special interest in that the plants are genetically modified plants expressing granule-bound starch proteins (such as GBSS) fused with other proteins of interest, particularly if the granule-bound starch protein is that which is found in the part of the protein of interest containing the amino group since, as described in Spanish Patent Application P201001115, the entire fusion protein will also linked to the starch granule. This, on one hand, facilitates isolating the fusion protein. If the part corresponding to a protein which is associated with the starch granule (such as, for example, the GBSS) is further bound to the part corresponding to the protein of interest by an amino acid sequence containing the protease recognition sequence, the treatment of the starch granules with the protease would allow releasing the protein of interest. Therefore a preferred embodiment of this aspect of the invention is that in which the plants are genetically modified plants, expressing a fusion protein at the amino end of which a granule-bound starch protein (such as GBSS) is located and, within said embodiment, that specific embodiment in which the granule-bound starch protein and the other protein are bound by an amino acid sequence comprising the protease recognition sequence, which can be, for example, trypsin (cleaving after amino acids lysine or arginine).

In yet another aspect, the present invention relates to a method for increasing the amount of chlorophyll accumulated by a plant, characterized in that the plant is cultured in the presence of a volatile compound-producing microorganism culture, without there being any contact between the plant and the microorganism, or in the presence of the volatiles emitted by the microorganism. In a possible embodiment of this aspect of the invention, the method for increasing the amount of chlorophyll accumulated by a plant can be characterized, for example, in that the plant is a maize plant or a pepper plant, which is cultured in the presence of a fungus belonging to the *Alternaria* or *Penicillium* genus, which is left to grow in a minimal medium supplemented with an organic carbon source, without there being any contact between the plant and the fungus, such as described in the tests described in the examples of the present application.

Finally, an additional aspect of the present invention is a method for increasing the resistance to water stress in a plant in which the plant is cultured in the presence of a volatile compound-producing microorganism culture without there being any contact between the plant and the microorganism, or in the presence of the volatiles emitted by the microorganism. This is so, as has been mentioned above, since in water stress conditions, the growth of plants growing in the presence of microbial volatiles decreases less with respect to the control plants than in the cases in which the microbial volatiles are not present, therefore the method of the invention for culturing plants in the presence of microbial volatiles can also be described as a method for increasing plant resistance to water stress.

As has been mentioned, the method of the invention, in any of its aspects (except that relating to the use of transgenic plants) requires that the cultivation of the plant or the placement of the detached leaves in which starch accumulation is to be induced, is performed such that the volatiles emitted by the microorganism are present in the atmosphere in which the plant is cultured. Having achieved this condition, the method of the invention can be carried out in different manners. A possibility is that the plant and the microorganism are cultured simultaneously in one and the same recipient, or that the leaves are introduced in a recipient in which the microorganism culture is being produced; in that case, to make sure that the plant contacts the volatiles emitted by the microorganism, the recipient is preferably a closed recipient which in turn contains the specific recipient, such as a Petri dish, in which the microorganism is preferably cultured in a solid medium. The common culturing recipient of the plant and the microorganism can be a greenhouse in which, preferably, the conditions of humidity, temperature and, even, air circulation speed are artificially controlled.

Since the method of the invention does not require contact between the microorganism and the plant, but requires the volatiles emitted by the microorganism, it is not necessary to cultivate the microorganism and plant in close proximity, but the plant can in turn be cultured in the presence of the volatiles emitted by the microorganism without the need for thereof to be located close to the plant. It is therefore possible to culture the microorganisms previously, in the culture site and conditions of choice, collecting the volatiles emitted to subsequently make the plant grow in the presence of said volatiles, making sure that the volatiles are present in the atmosphere in which the plant is cultured. The mixture of volatiles can reach the atmosphere through evaporation from a solution containing them which is in the plant culture site, allowing the mixture of volatiles used to be the mixture of volatiles present in the culture medium of the microorganism, after filtering it and mixing it with the solution from which they will be evaporated, such as that performed in one of the examples shown below, a possibility that can be carried out preferably when the culture medium of the microorganism was a liquid medium; in terms of the solution from which the volatiles evaporate, a possibility is that the solution is, for example, the irrigation water of the plant. In another possible embodiment the mixture of volatile compounds is supplied to the culture atmosphere; the possibilities for performing thereof include: the possibility of insufflating the volatile compound to the culture atmosphere (a particularly interesting possibility if the plant is cultured in a greenhouse); application by means of fumigating or spraying. Whatever the method of application to the culture atmosphere is, it is preferably performed together with one or more compounds of interest, such as a fertilizer, a pesticide, or mixtures thereof.

As used herein, the term "microorganism" includes bacteria, yeasts, algae and protozoa, all those which are generally unicellular, as well as multicellular microscopic fungi such as molds, which can be propagated and manipulated in a laboratory.

The microorganism used can belong to a species which are pathogenic or non-pathogenic to the plant, which may or may not coexist with the plant in natural conditions. Said microorganism can be a bacterium, a yeast or a microscopic fungus. Among them, the following are particularly preferred, fungi belonging to the *Penicillium* (for example *Penicillium charlessi, Penicillium aurantiogriseum*) or *Alternaria* (for example *Alternaria alternata*) genus, the yeasts of the *Saccharomyces cerevisiae* species and the bacteria belonging to the *Bacillus* genera (particularly, *Bacillus subtilis* and, for example, *Bacillus subtilis* 168), *Salmonella* (for example, *Salmonella enterica* LT2), *Escherichia* (particularly, *Escherichia coli* and, very particularly, *Escherichia coli* BW25113), *Agrobacterium* (particularly, *Agrobacterium tumefaciens* and, very particularly, *Agrobacterium tumefaciens* EHA105 or GV2260) or *Pseudomonas* (particularly, *Pseudomonas syringae* and, very particularly, *Pseudomonas syringae* 1448A9, 49a/90 or PK2).

As has been described previously, when the microorganism is chosen from bacteria, it can be chosen from a genus different from *Bacillus* or *Paenibacillus*, which are the genera to which the specific strains of rhizobacteria belong in which a positive effect of the volatile emissions thereof on plant growth had previously been detected when grown in very rich media: both genera can be excluded from the group of eligible bacteria. In any case, it has been observed that the volatiles emitted by bacteria belonging to these genera, of strains different from *Bacillus subtilis* GB03 and *Bacillus amyloliquefaciens* IN937, are capable of producing the effect of growth increase in plants when the bacteria are cultured in a medium lacking organic compounds having amino groups, particularly amino acids and/or proteins, such as minimal medium supplemented with an organic carbon source, also causing an increase in starch accumulation: none of these effects were expected from the prior results obtained with rhizobacteria volatiles, which seemed to indicate that the effect on the growth was exclusive of the volatiles emitted by certain strains. Furthermore, starch accumulation induction, has not been previously described for mixture of volatiles emitted by microorganisms and, as shown below in the examples of the invention, is observed for all the microorganisms with which the experiments were performed: therefore, as has been mentioned above, it is considered that any bacteria, microscopic fungus or yeast can be chosen for carrying out the aspect of the method of the invention relating specifically to starch accumulation, be it in growing whole plants or in detached leaves.

In any of the aspects of the method of the invention which do not relate to the specific use of transgenic plants (method for increasing plant growth, method for increasing starch accumulation, method for increasing chlorophyll accumulation, method for increasing the amount of starch-associated proteins in a plant, method for increasing the resistance to water stress . . . ), particularly the growth of the microorganism preferably occurs in a medium lacking organic compounds including nitrogen in its formula or, at least, lacking organic compounds having amino groups, such as amino acids and/or proteins. Culturing in a minimal medium containing an organic compound as carbon source, which can be, for example, sucrose or glucose or other organic compounds such as succinate is of very special preference. Therefore, it has thus been performed, for example, in the tests presented in the examples of the present application in which the fungus *Alternaria alternata* has been used as fungal volatile producer resulting in the desired effects of growth increase, modification of the growth pattern and an increase in starch accumulation: for the culture of said fungus, solid MS medium supplemented with 90 mM sucrose has been resorted to.

In any of the aspects of the invention, as has already been mentioned, the plant can be an angiosperm, a monocotyledon or a dicotyledon. Specific examples thereof can be those plants used in the tests of the present application, such as maize, pepper, *Arabidopsis thaliana*, potato, tobacco or other plants, preferably plants of agricultural or industrial interest.

Among the plants, angiosperms (both monocotyledons and dicotyledons) are preferred, in which an increase in the number of branching and the number of flowers with respect to the control plants have been observed. This effect also allows another aspect of the invention to be a method for inducing flowering and for increasing the number of branching and/or flowers produced by a plant, in which the objective is achieved by culturing the plant in the presence of a volatile compound-producing microorganism, without there being any contact between the plant and the microorganism. When the effect sought is increasing the number of flowers, the plant would logically be a plant capable of producing them: an angiosperm, both monocotyledon and dicotyledon.

The invention will now be explained in more detail by means of the examples and drawings shown below.

Panel (A) illustrates the "classic model", according to which the starch biosynthesis process takes place exclusively in the chloroplast, separately from the sucrose biosynthesis process occurring in the cytosol.

Panel (B) illustrates the "alternative model" in which both the sucrose and starch biosynthesis pathways are interconnected by means of ADPG-producing SuSy activity (sucrose synthase).

Compounds involved: FBP: fructose-1,6-bisphosphate; F6P: fructose-6-bisphosphate; G6P: glucose-6-phosphate; G1P: glucose-1-phosphate; ADPG; ADP-glucose; UDPG: UDP-glucose. Enzymatic activities: 1,1': fructose-1,6-bisphosphate aldolase; 2,2': fructose-1,6-bisphosphatase; 3: PPi: fructose-6-phosphate phosphotransferase; 4,4': phosphoglucose isomerase; 5,5': phosphoglucomutase; 6: UDPG pyrophosphorylase; 7: sucrose phosphate synthase; 8: sucrose-phosphate-phosphatase; 9: AGP; 10: SS (starch synthase); 11: starch phosphorylase; 12, SuSy (sucrose synthase).

Figure 1:
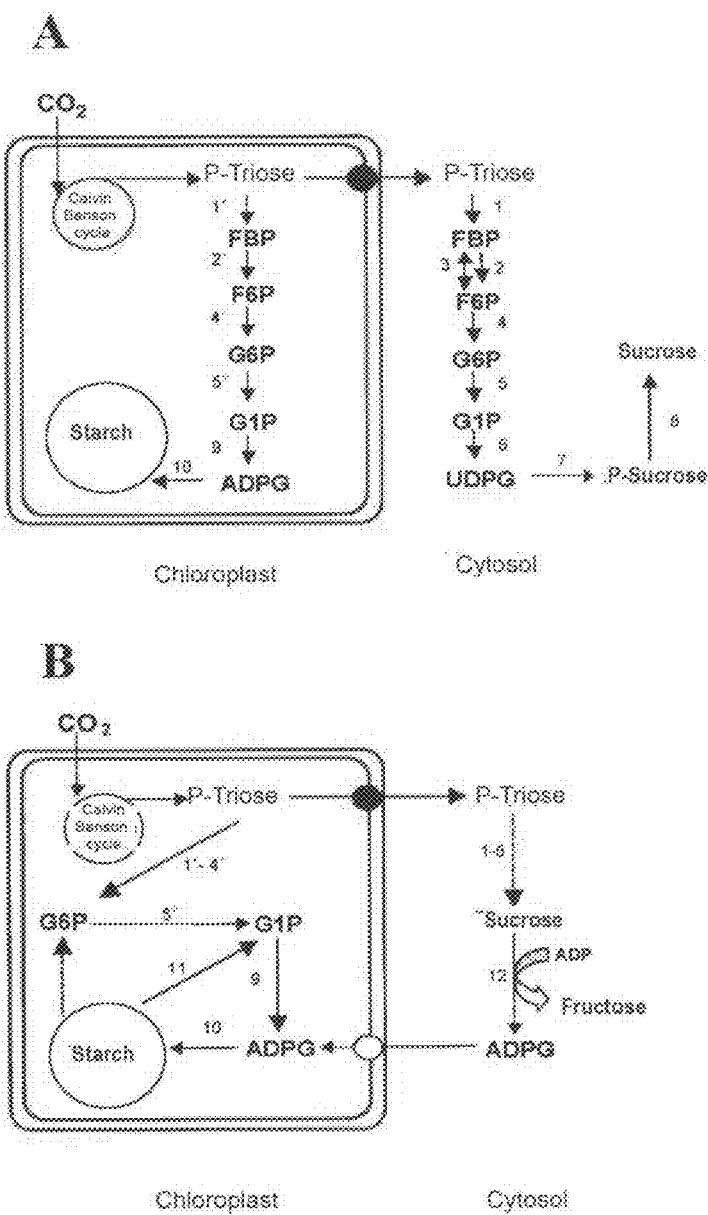
FIG. 1: Suggested starch synthesis pathways in leaves of origin.
Figure 2:
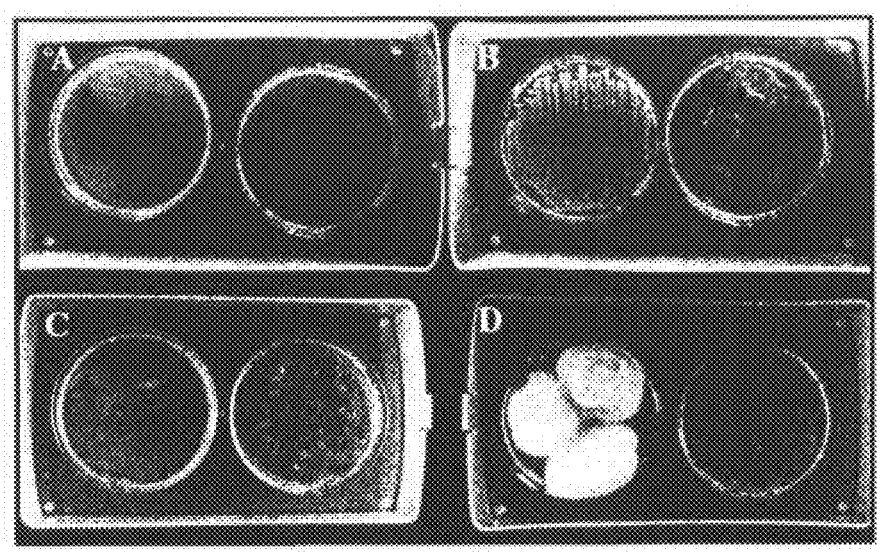

FIG. 2: *Arabidopsis* plant culture conditions and the effect of microbial volatiles on said conditions.

Panels (A), (B), (C) and (D): Photographs illustrating *Arabidopsis* plant culture conditions in the absence (A and C) and the presence (B and D) of microbial volatiles. In order to see the effect of the volatile, Petri dishes containing completely developed plants were introduced in plastic boxes in which there had previously been included cultures of *E. coli* BW25113 grown in solid M9 medium supplemented with 50 mM glucose (panel B) and *Alternaria alternata* grown in solid MS medium supplemented with 90 mM sucrose (panel D). The boxes were sealed and the plants were harvested at the indicated incubation times to perform the analyses.

Figure 3:
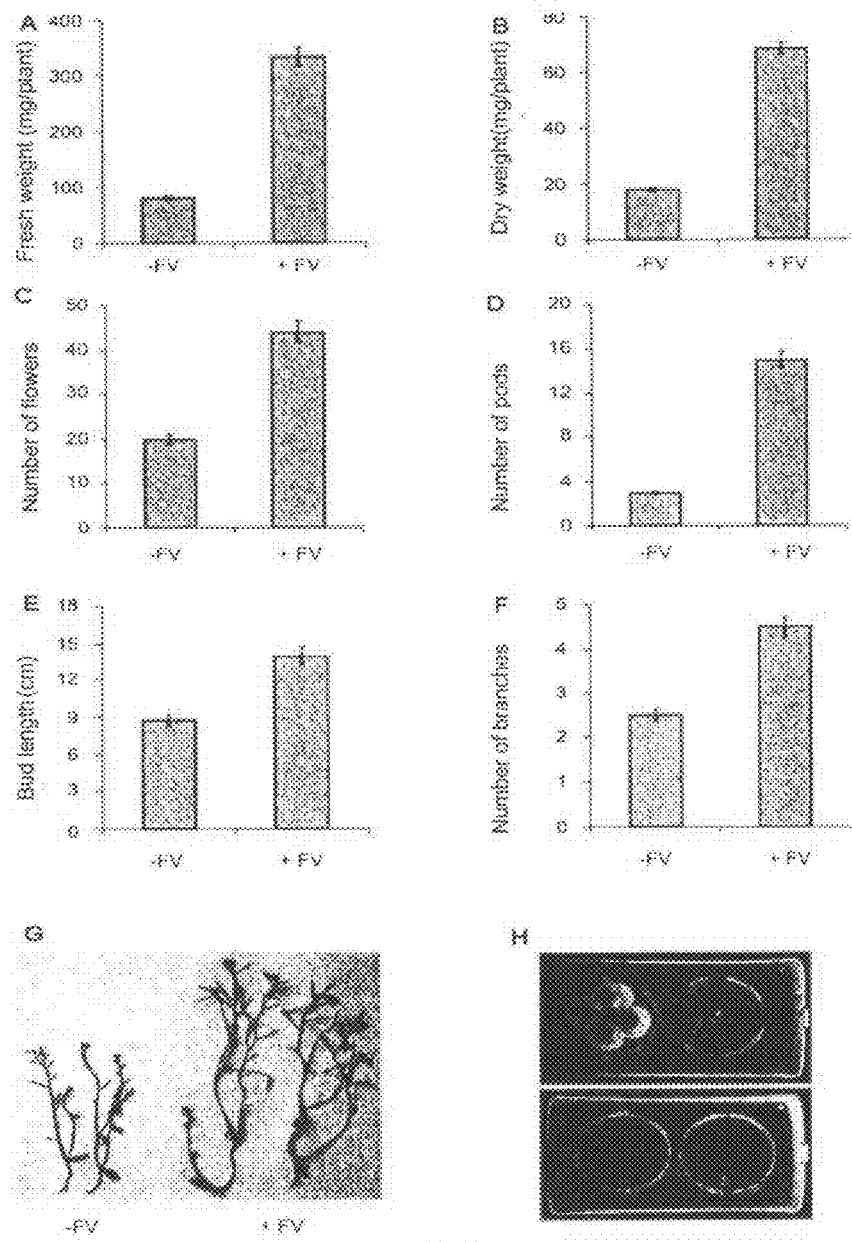

FIG. 3: Effect of the volatiles produced by *Alternaria alternata* on the fresh weight (panel A), dry weight (panel B), number of flowers (panel C), number of pods (panel D), length of the shoot (panel E) and number of branches (panel F) of *Arabidopsis*. The photographs of panels G and H illustrate the positive effect of fungal volatiles (FVs) on the number of flowers, pods, length of the shoot and number of branches in plants exposed for 6 days to the FVs. *A. alternata* was cultured in solid MS medium supplemented with 90 mM sucrose.

Figure 4:
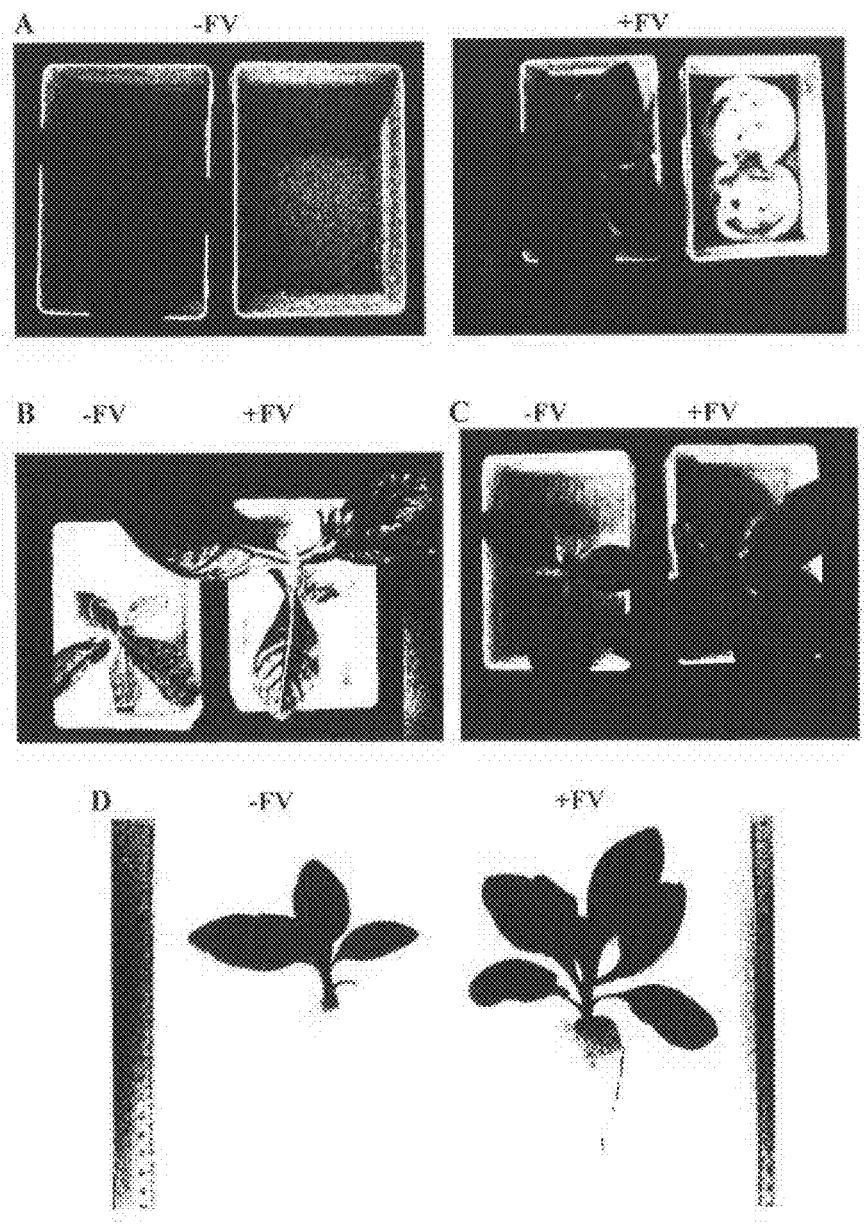

FIG. 4: Tobacco plant culture conditions and the effect of microbial volatiles on the development and growth of the plants:

Panel A: Photographs illustrating the conditions of tobacco plant culture in the absence (−FV) or in the presence (+FV) of fungal volatiles (FV) emitted by a culture of *Alternaria alternata*. The plants were cultured for 6 days and were then compared.

Panels B and C: Comparison of tobacco plants cultured in the same conditions, except the absence (−FV) or presence (+FV) of the *Alternaria alternata* culture. It is observed that the plants grown in the presence of fungal volatiles emitted by *A. alternata* are larger, which is seen particularly in the leaves, and they even have a higher number of leaves (panel C). It is further observed that FV-treated plants blossom sooner.

Panel D: Photographs showing whole tobacco plants, including the roots, grown in the absence (−FV) or presence (+FV) of the *Alternaria alternata* culture. It is seen that the size of the root is larger in the case of the plants grown in +FV conditions. *A. alternata* was cultured in solid MS medium supplemented with 90 mM sucrose.

Figure 5:
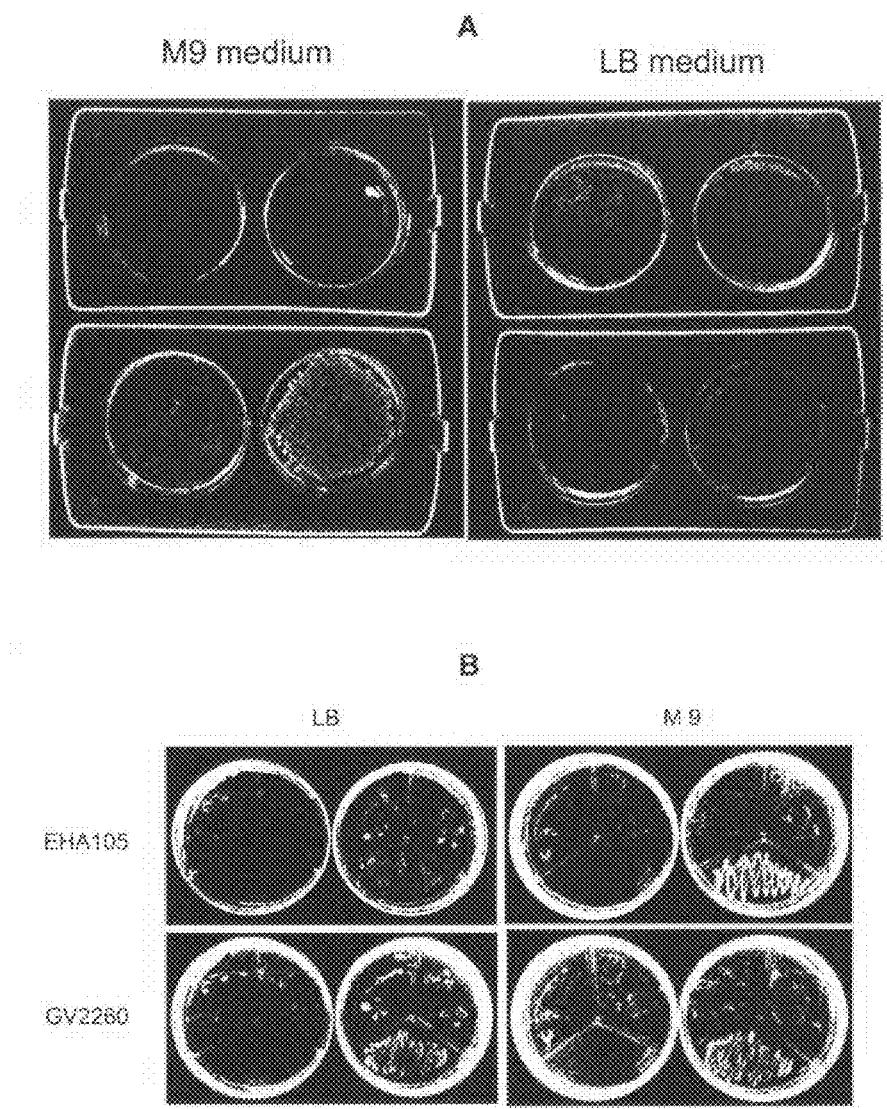
Figure 5:
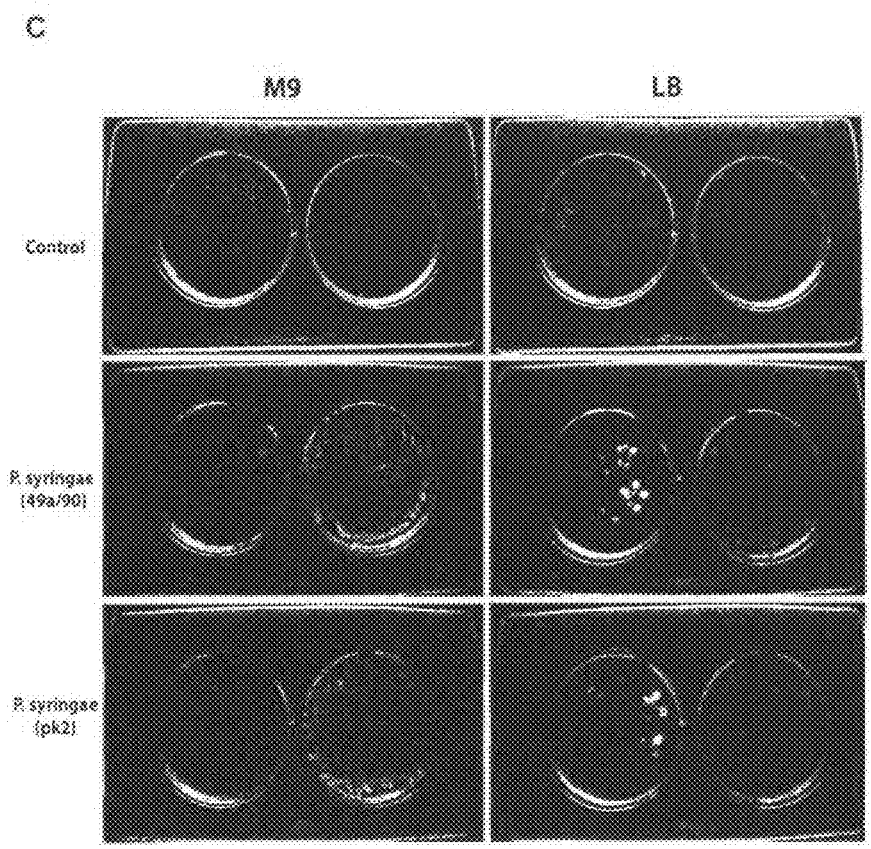

FIG. 5. Effect of the volatiles produced by *Salmonella enterica* LT2 (panel A), the strains of *Agrobacterium tumefaciens* indicated next to the photographs (EHA105 or GV2260) (panel B), or the strains of *Pseudomonas syringae* 49a/90 and PK2 (panel C) on the growth of *Arabidopsis*, according to the culture medium of the bacteria: minimal medium (M9) or LB medium supplemented with 50 mM glucose.

It is observed that the *Arabidopsis* plants grown in the presence of bacteria grown on LB medium have yellow zones (lighter points on the leaves) and a smaller size and/or an aspect of being sick.

Figure 6:
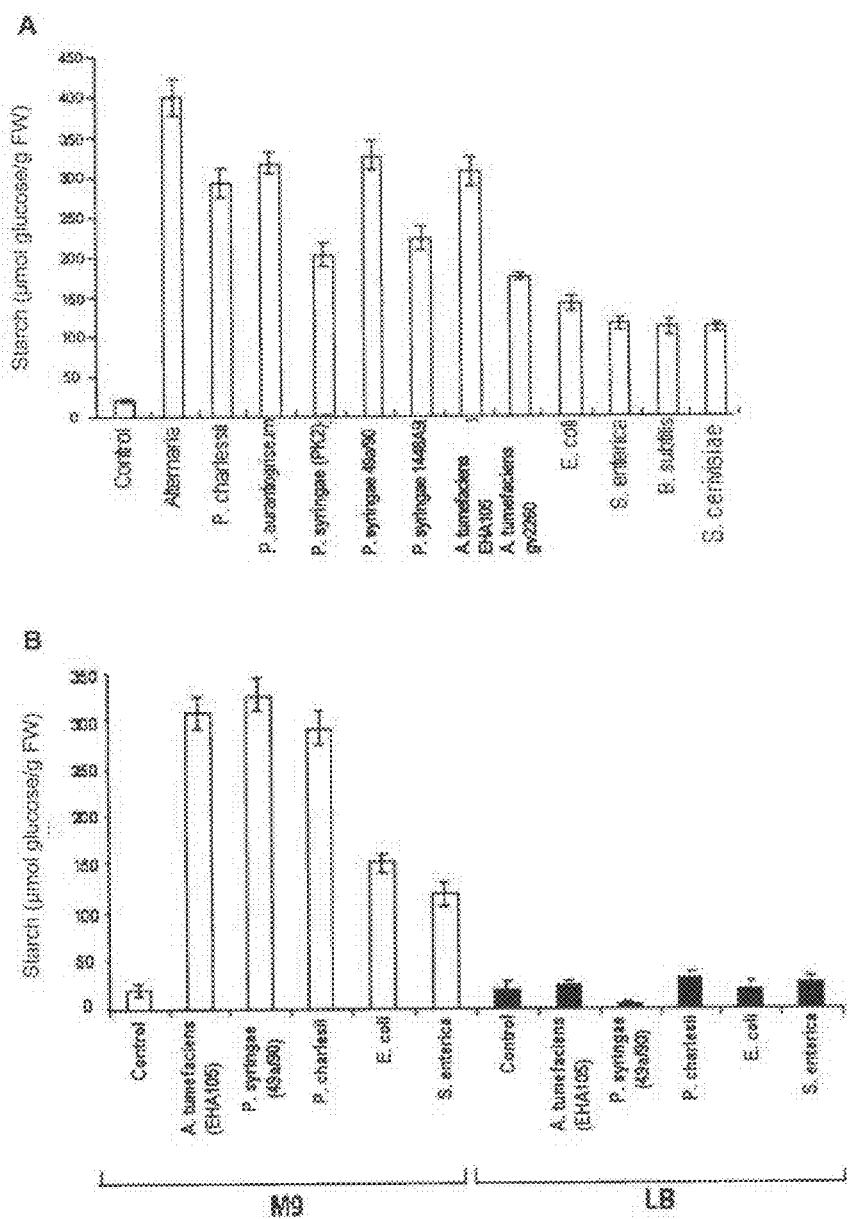
Figure 6:
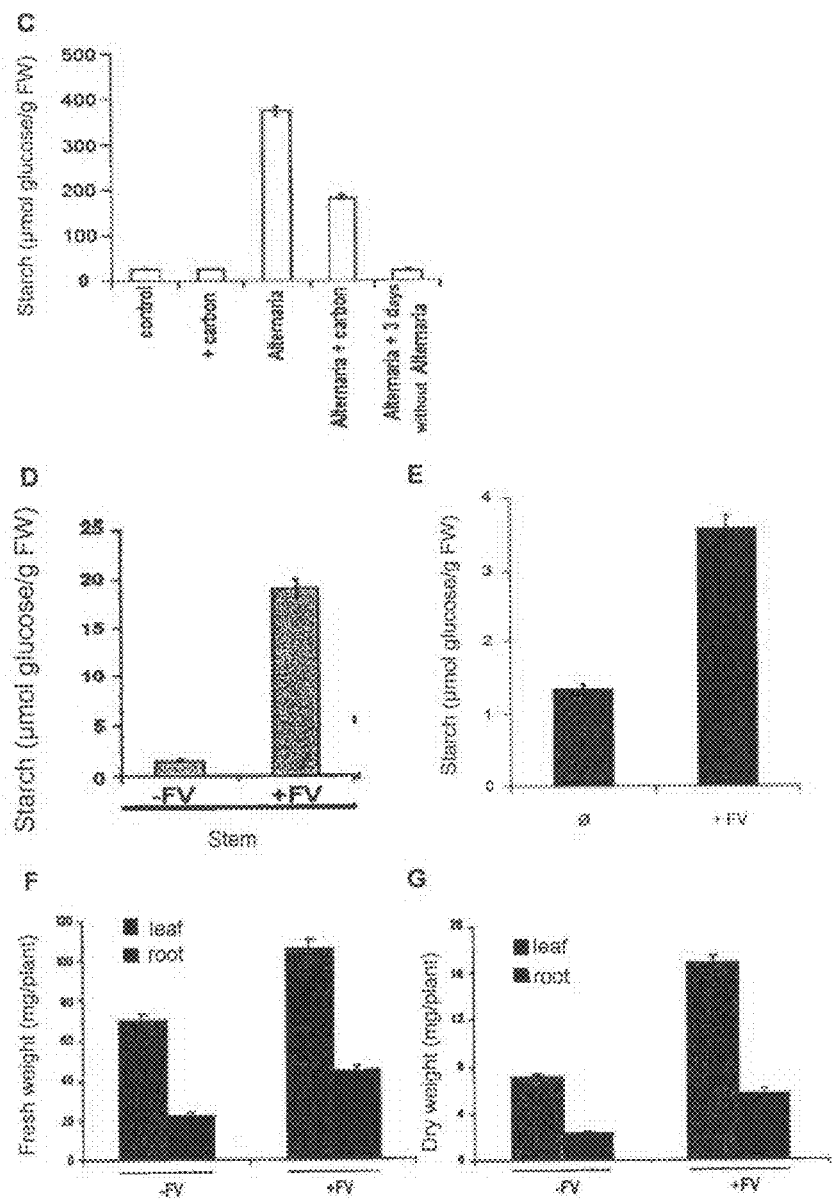

FIG. 6: Effect of microbial species volatiles on starch accumulation in leaves of *Arabidopsis*.

Panel A: starch content in leaves of *Arabidopsis* plants cultured 2 days in solid MS medium supplemented with 90 mM sucrose in the presence or absence of: *Alternaria alternata, Penicillium charlessi, Penicillium aurantiogriseum, Pseudomonas syringae* PK2, *Pseudomonas syringae* 49a/90, *Pseudomonas syringae* 1448A9, *A. tumefaciens* GV2260, *A. tumefaciens* EHA105, *E. coli* (BW25113), *Salmonella enterica* (LT2), *B. subtilis* 168, *Saccharomyces cerevisiae* NA33. All the microorganisms except *S. cerevisiae, Penicillium aurantiogriseum*, and *Penicillium* charlessi were grown in solid M9 medium supplemented with 50 mM glucose. *P. aurantiogriseum, P. charlessi* and *A. alternata* were grown in solid MS medium supplemented with 90 mM sucrose.

Panel B: quantification of the starch content in leaves of *Arabidopsis* plants cultured in the presence of different bacteria and fungi as indicated under the corresponding bars, which bars are grouped according to the culture medium of the microorganism: solid minimal medium (M9) supplemented with 90 mM glucose (non-shaded bars) or solid LB medium supplemented with 90 mM glucose (darkness shaded bars). It is observed that the positive effect on the increase in starch only takes place when the microorganisms grow in minimal medium.

Panel C: starch content in leaves of *Arabidopsis* plants cultured in the same culture conditions as in Panel A, in the presence of carbon, a culture of *A. alternata, A. alternata* in the presence of carbon, or an initial *Alternaria* culture withdrawn for the following 3 days, as indicated under the bars. The reduction of the inducing effect in the presence of carbon and the disappearance of the effect after 3 days out of contact with the fungal volatiles are observed. *A. alternata* was cultured in solid MS medium supplemented with 90 mM sucrose.

Panel D: quantification of the starch content in stems of *Arabidopsis* grown in the absence (−FV) or in the presence (+FV) of fungal volatiles produced by *A. alternata*. A very large increase in the starch in the stems in +FV conditions is observed. *A. alternata* was cultured in solid MS medium supplemented with 90 mM sucrose.

Panel E: starch content in roots of *Arabidopsis* grown in the absence (Ø) or in the presence (+FV) of fungal volatiles produced by *A. alternata*. A large increase in the starch in the roots in +FV conditions is also observed. *A. alternata* was cultured in solid MS medium supplemented with 90 mM sucrose.

Panels F and G: comparison of the biomass observed in leaves (first bar of each pair, dotted shading) and in roots (second bar of each pair, darker solid shading) of *Arabidopsis*, in the absence (−FV) or in the presence (+FV) of fungal volatiles produced by *A. alternata*. The effect is observed if both the fresh weight (panel F) and the dry weight (panel G) are determined. *A. alternata* was cultured in solid MS medium supplemented with 90 mM sucrose.

Figure 7:
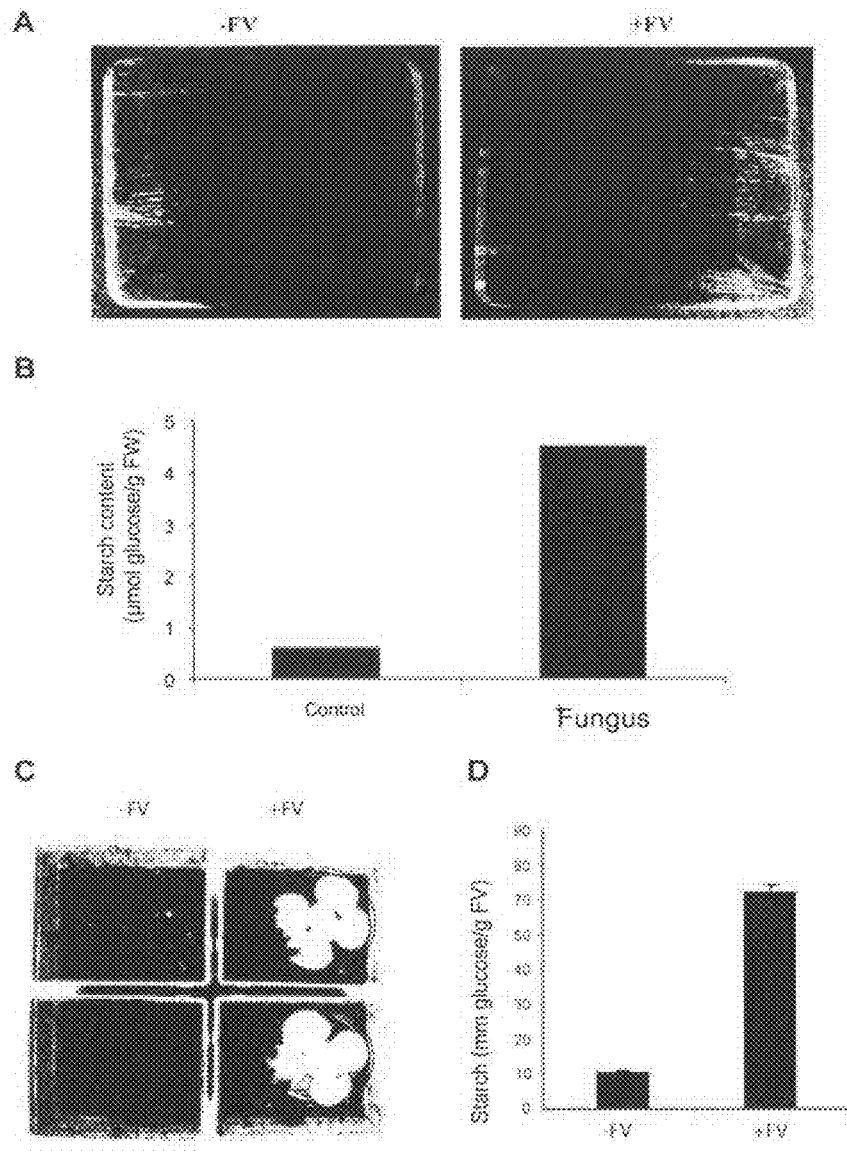

FIG. 7: Effect of the fungal volatiles on maize plants and *Arabidopsis* cultured on soil.

Panel A: Photographs of maize plants grown on soil in the absence (−FV) or presence for 6 days (+FV) of fungal volatiles produced by *Alternaria alternata* fungi cultured in solid MS medium supplemented with 90 mM sucrose. It is observed that the plants grown in the presence of volatiles are more robust. As demonstrated in Panel B, they accumulate more starch.

Panel B: Starch content, expressed in micromoles of glucose per gram of wet weight (FW), of the leaves of maize plants of panel A. Control: plants grown in the absence of fungal volatiles; +Fungus: plants grown in the presence for 6 days of a culture of *A. alternata* emitting fungal volatiles.

Panel C: Photographs of *Arabidopsis* plants grown on soil in the absence (−FV) or presence (+FV) of fungal volatiles produced by *Alternaria alternata* fungi cultured in solid MS medium supplemented with 90 mM sucrose. As demonstrated in Panel D, they accumulate more starch.

Panel D: Starch content, expressed in micromoles of glucose per gram of wet weight (FW), of the leaves of *Arabidopsis* plants of panel C. −FV: plants grown in the absence of fungal volatiles; +FV: plants grown for 6 days in the presence of a culture of *A. alternata* emitting fungal volatiles.

Figure 8:
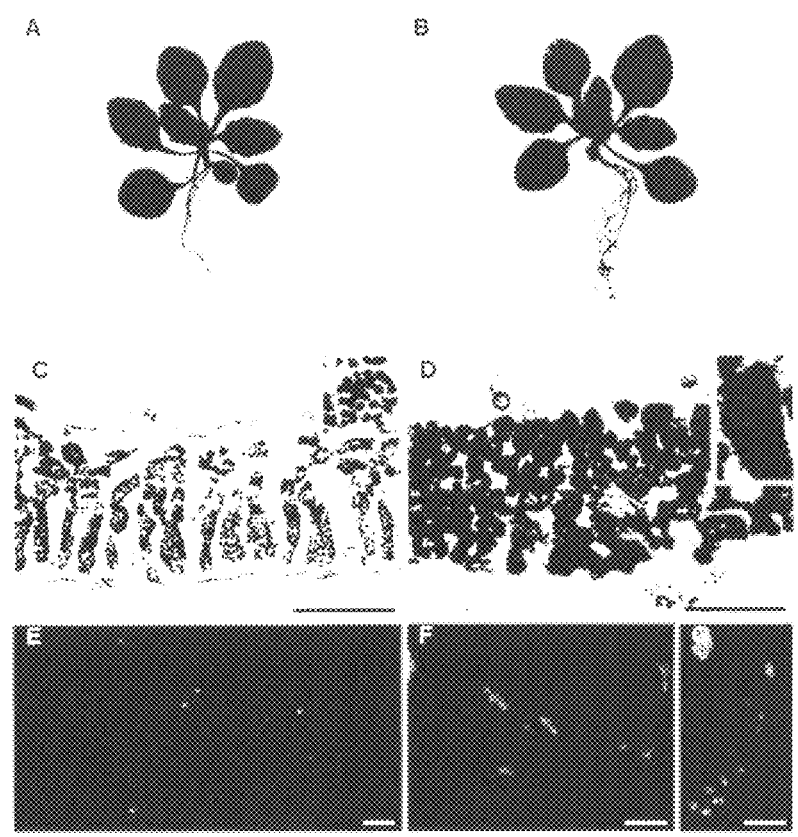

FIG. 8: Visual and microscopic examination of tissues of plants grown in the absence or presence of volatiles emitted by *Alternaria alternata* cultured in solid MS medium supplemented with 90 mM sucrose:

Panels A and B: iodine staining of whole *Arabidopsis* plants cultured in the absence or in the presence of FVs, respectively.

Panels C and D: analysis of iodine stainings by means of optical microscopy of cross sections of leaves of plants cultured in the absence or in the presence of FVs, respectively. Inserts: Pattern of staining intensity and distribution of material positive for iodine in individual mesophyll cells.

Panels E, F, G: confocal laser scanning microscopy of leaves of plants expressing GBSS-GFP, cultured in the absence (E) or presence (F and G) of FVs.

Bar=5 µm in E, F, G; Bar=100 µm in C and D.

Figure 9:
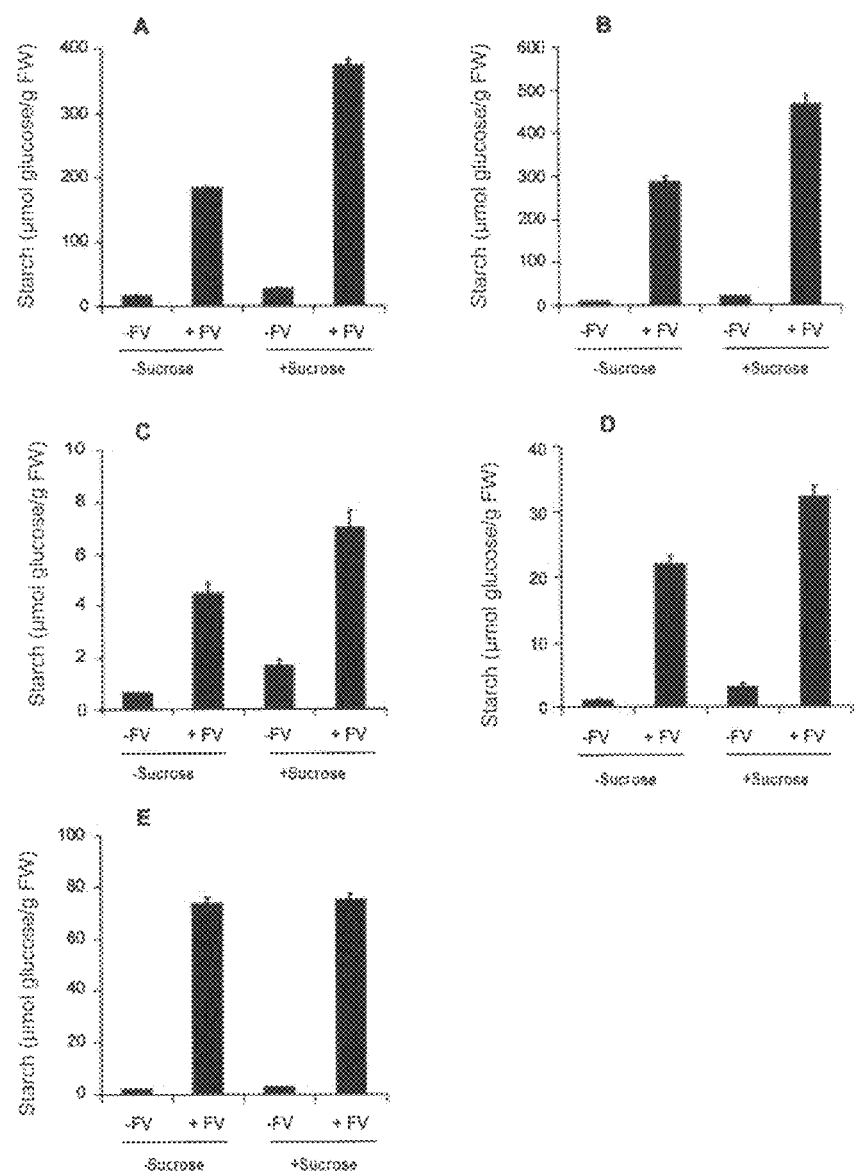

FIG. 9: Ubiquity of the effect of the microbial volatiles among the plants.

Graphs depicting the amount of starch (expressed as micromoles of glucose per gram of fresh weight of the corresponding leaf extract) detected in *Arabidopsis* (A), potato (B), maize (C), barley (D) and (E) tobacco plants cultured for 3 days in solid MS medium, with or without 90 mM sucrose, as indicated under the bars, in the presence (bars with the legend "+FV") or in the absence (bars with the legend "−FV") of volatiles emitted by a culture of *A. alternata* grown in solid MS medium supplemented with 90 mM sucrose.

Figure 10:
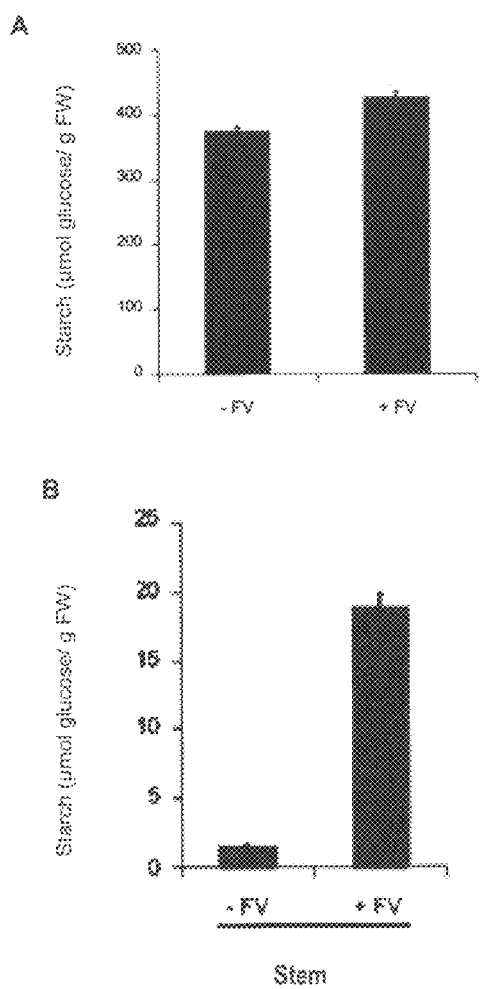

FIG. 10: Graphs depicting the amount of starch (expressed as micromoles of glucose per gram of fresh weight of the corresponding plant extract) accumulated in tubers (panel A) and stems (panel B) of potato plants cultured in solid MS medium without sucrose in the presence or in the absence of FVs emitted by *A. alternata* cultured in solid MS medium supplemented with 90 mM sucrose.

Figure 11:
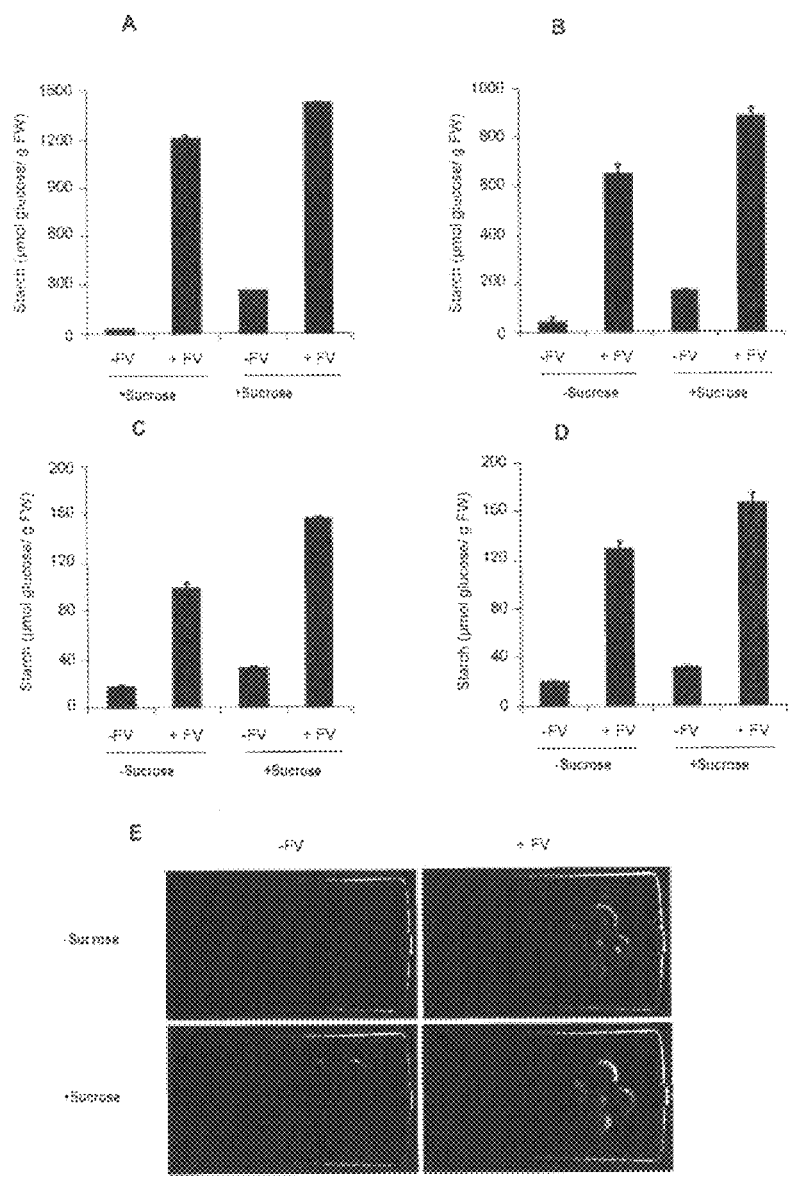

FIG. 11: Starch accumulation in detached leaves of the plant promoted by fungal volatiles emitted by a culture of *A. alternata* grown in solid MS medium supplemented with 90 mM sucrose.

Panels A, B, C, D: Graphs depicting the amount of starch (expressed as micromoles of glucose per gram of fresh weight of the corresponding leaf extract) detected in leaves of *Arabidopsis* (A), potato (B), maize (C), barley (D) maintained for 2 days in solid MS medium (with or without 90 mM sucrose, as indicated under the bars), in the presence (bars with the legend "+FV") or in the absence (bars with the legend "−FV") of volatiles emitted by a culture of *A. alternata* grown in solid MS medium supplemented with 90 mM sucrose.

Panel E: Photographs illustrating the conditions in which the leaves of potato plants were maintained in the absence (column with the label "−FV") or in the presence (column with the label "+FV") of microbial volatiles.

Figure 12:
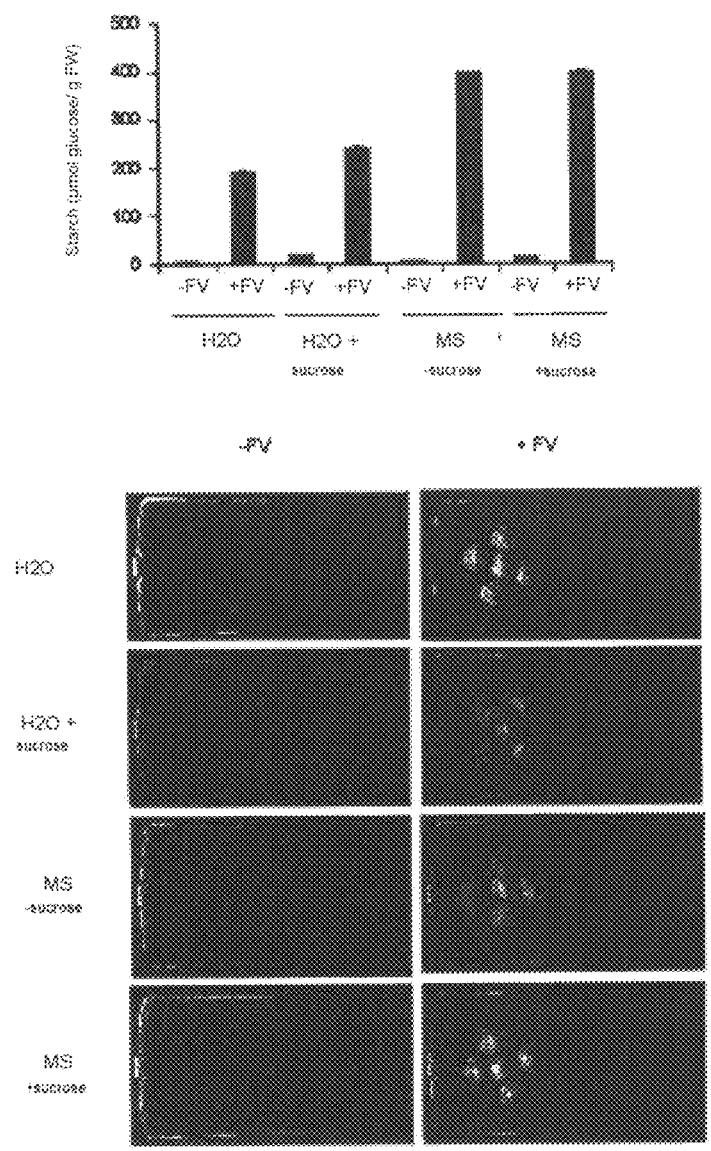

FIG. 12: Starch accumulation in detached leaves of the plant cultured on the surface of wet paper in liquid MS or in water promoted by fungal volatiles emitted by a culture of *A. alternata* grown in solid MS medium supplemented with 90 mM sucrose.

Panel A: Graph depicting the amount of starch (expressed as micromoles of glucose per gram of fresh weight of the corresponding leaf extract) detected in leaves of tobacco maintained for 2 days on wet paper in water or in liquid MS (with or without 90 mM sucrose, as indicated under the bars), in the presence (bars with the legend "+FV") or in the absence (bars with the legend "−FV") of volatiles emitted by a culture of *A. alternata*.

Panel B: Photographs illustrating the conditions in which the leaves of tobacco plants cultured on the surface of wet paper in liquid MS or in water were maintained in the absence (column with the label "−FV") or in the presence (column with the label "+FV") of microbial volatiles emitted by *A. alternata*.

Figure 13:
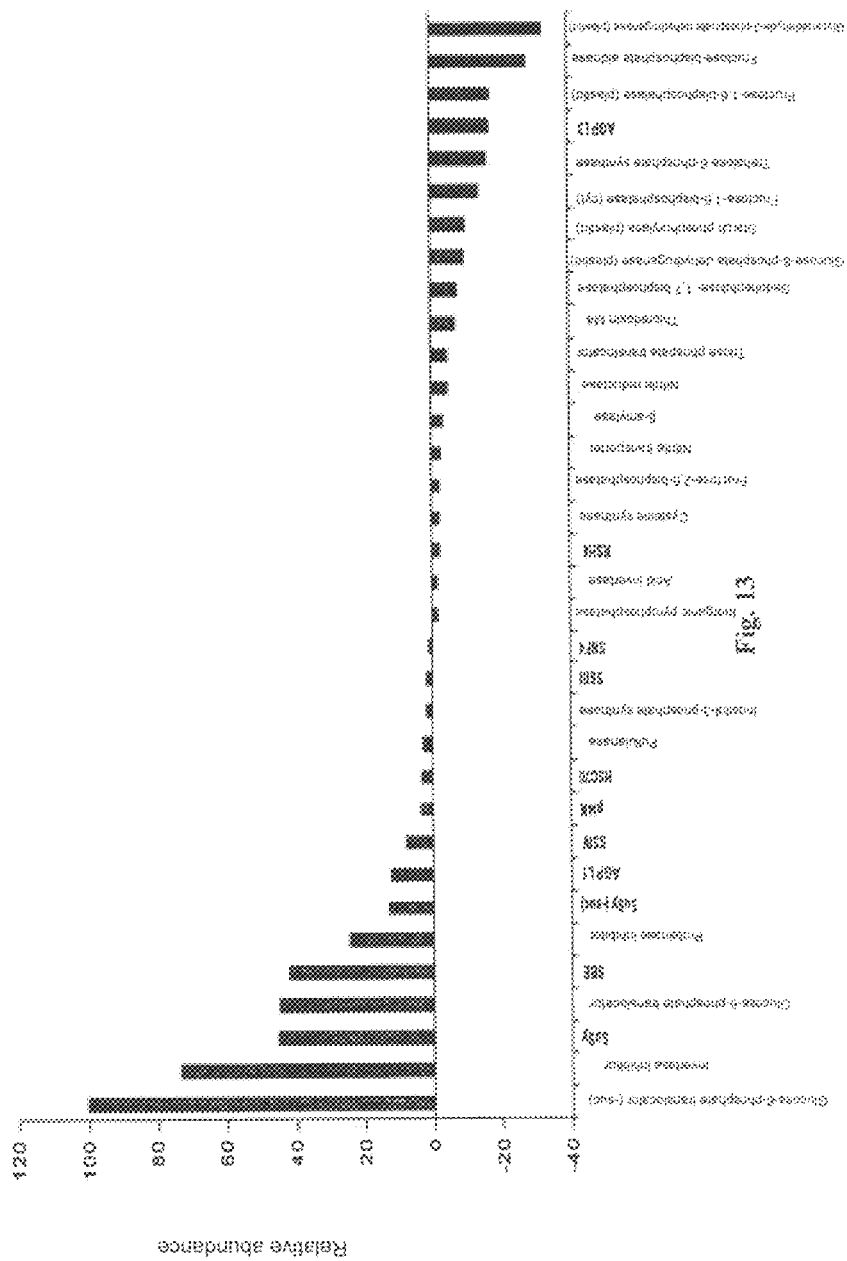

FIG. 13: Relative abundance, expressed as a variation factor, of the levels of transcripts of the genes indicated on the x-axis, measured by means of quantitative real time (RT)-PCR, in leaves of potato plants cultured in the presence of fungal volatiles emitted by *A. alternata* grown in solid MS medium supplemented with 90 mM sucrose. The variation factors depicted are relative to the control leaves of plants cultured in the absence of FVs. The plants were cultured for 3 days in the presence of FVs in solid MS medium supplemented with 90 mM sucrose, and were harvested at the end of the light period. The levels of transcripts of SuSy (sucrose synthase) and of the glucose-6-P translocator were measured both in the presence (+sac) and in the absence (−sac) of sucrose.

Figure 14:
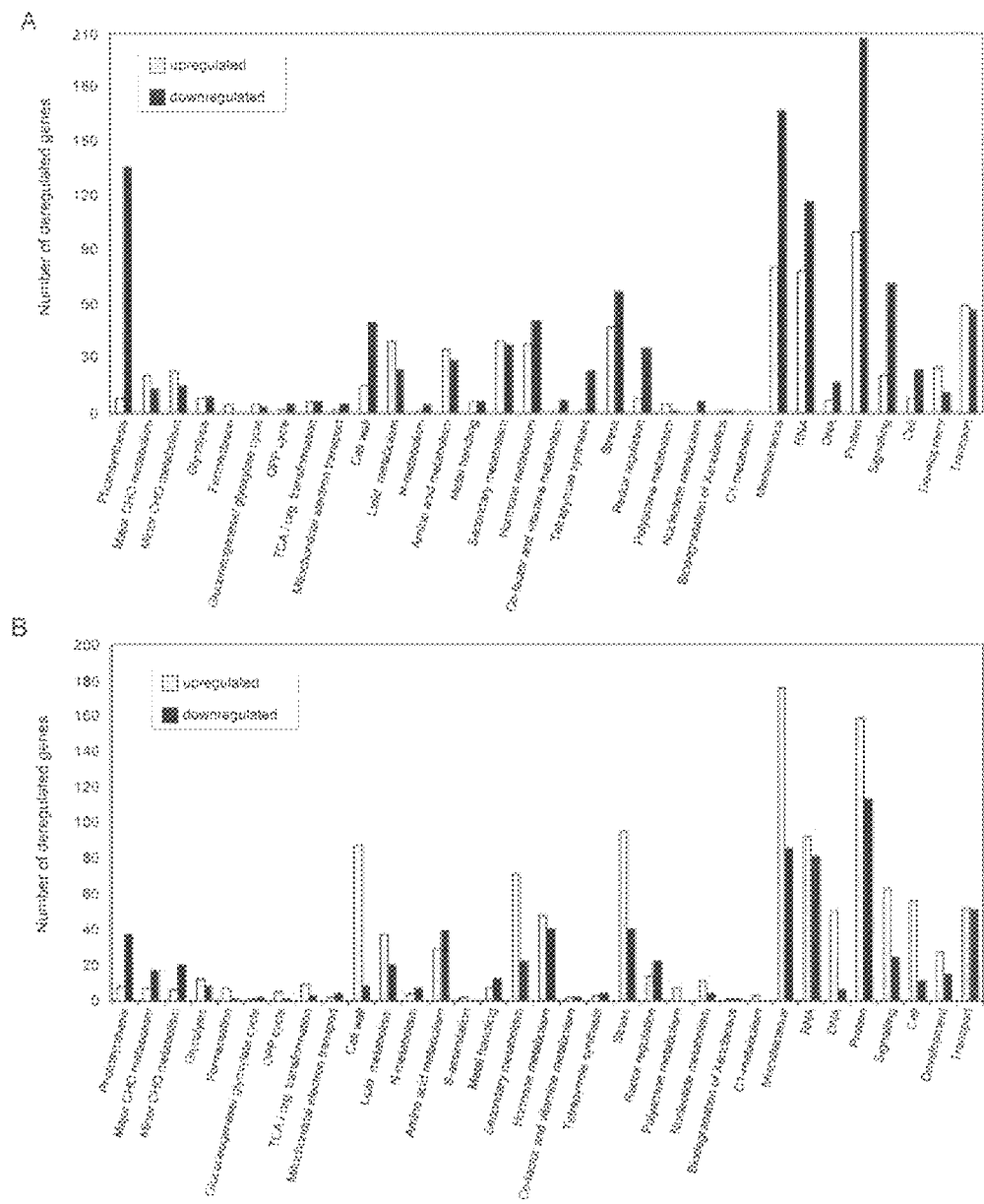

FIG. 14: Functional categorization of the transcripts differentially expressed in potato leaves cultured in MS supplemented (panel A) or not (panel B) with 90 mM sucrose in the presence of fungal volatiles emitted by *A. alternata* grown in solid MS medium supplemented with 90 mM sucrose. The transcripts were identified using the POCI 44K 60-mer oligo array (http://pgrc.ipk-gatersleben.de/poci). The significantly up-regulated and down-regulated transcripts (difference of 2.5-fold in plants cultured with sucrose and difference of 1.9-fold in plants cultured without sucrose) compared with the controls were classified according to their theoretical functional category according to MapMan software. Said category is indicated under the x-axis. The number of deregulated genes in each categorical group is indicated on the y-axis. The up-regulated genes are shown in lighter shaded bars and the down-regulated genes are shown in darker shaded bars. The genes of the category "no effect found" were not included in the graph FIG. 15: Analysis of AGP in Western blotting of leaves of potato plants, in non-reducing conditions (without 10 mM dithiothreitol: −DTT) and reducing conditions (with 10 mM dithiothreitol: +DTT). The whole plants were cultured for 3 days in solid MS medium supplemented with 90 mM sucrose in the presence ("+FV") or in the absence ("−FV") of volatiles emitted by *A. alternata* grown in solid MS medium supplemented with 90 mM sucrose FIG. 16: Graphs showing that the changes in AGP activity play a minor role in the volatile-induced starch accumulation in potato leaves: (A) AGP activity, (B) starch content, and (C) AGP content in leaves of wild-type plants (WT) and AGP62 plants (antisense plants of the ADPG pyrophosphorylase small subunit) cultured in the presence ("+FV") and in the absence ("−FV") of volatiles emitted by *A. alternata* grown in solid MS medium supplemented with 90 mM sucrose. The whole plants were cultured for 3 days in solid MS medium supplemented with 90 mM sucrose.

Figure 17:
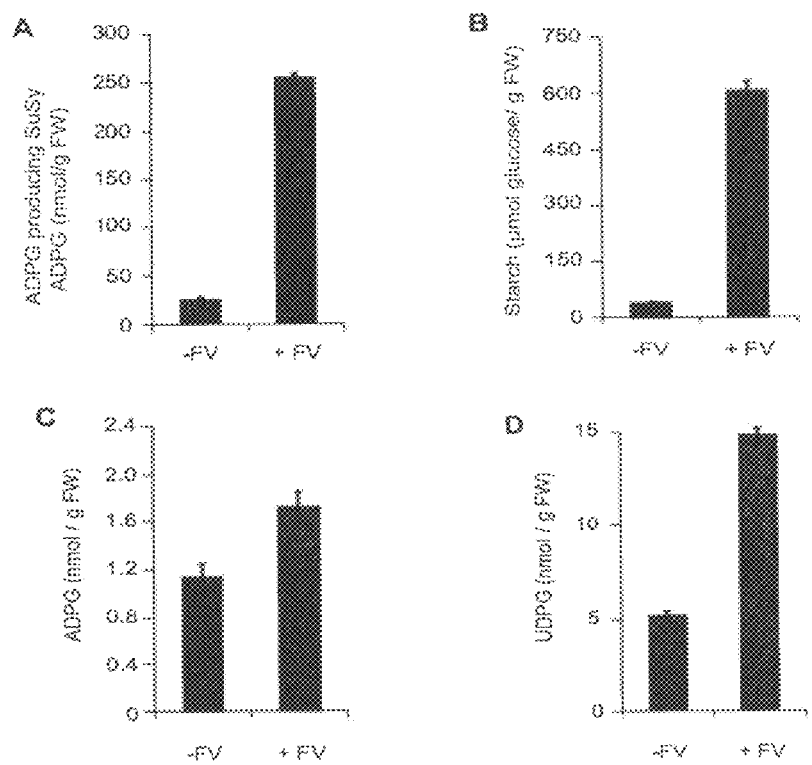

FIG. 17: Graphs depicting, in potato leaves cultured in the presence (+FV) or in the absence (−FV) of fungal volatiles emitted by *Alternaria alternata* grown in solid MS medium supplemented with 90 mM sucrose: the ADPG-producing SuSy activity (panel A), and the intracellular starch (panel B), ADPG (panel C) and UDPG (panel D) contents, all expressed with reference to grams of fresh weight. Correlation between SuSy (sucrose synthase) activity and the contents of the other compounds is observed.

Figure 18:
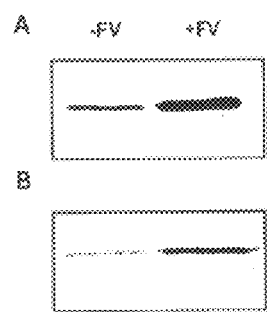

FIG. 18: Analysis of SuSy in Western type blotting in leaves of potato plants cultured in the presence (A) and absence (B) of FV-treated and non-treated sucrose emitted by *A. alternata* grown in solid MS medium supplemented with 90 mM sucrose.

Figure 19:
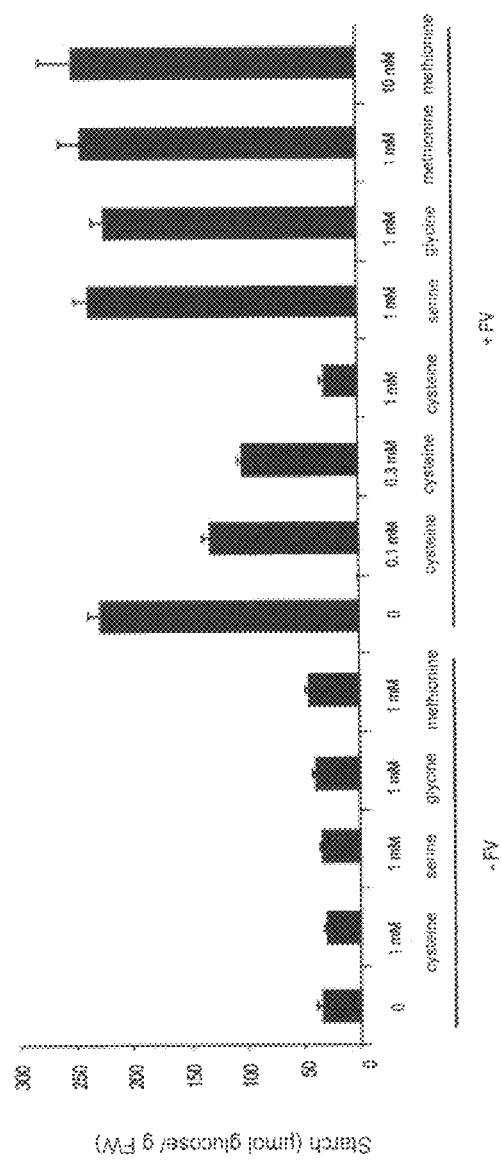

FIG. 19: Graph depicting the starch content (expressed as μmoles of glucose per gram of fresh weight) measured in potato plants cultured for 2 days in MS supplemented with 90 mM sucrose and the indicated concentrations of cysteine, glycine, serine and methionine in the absence (−FV) or in the presence (+FV) of volatiles emitted by A. alternata grown in solid MS medium supplemented with 90 mM sucrose.

Figure 20:
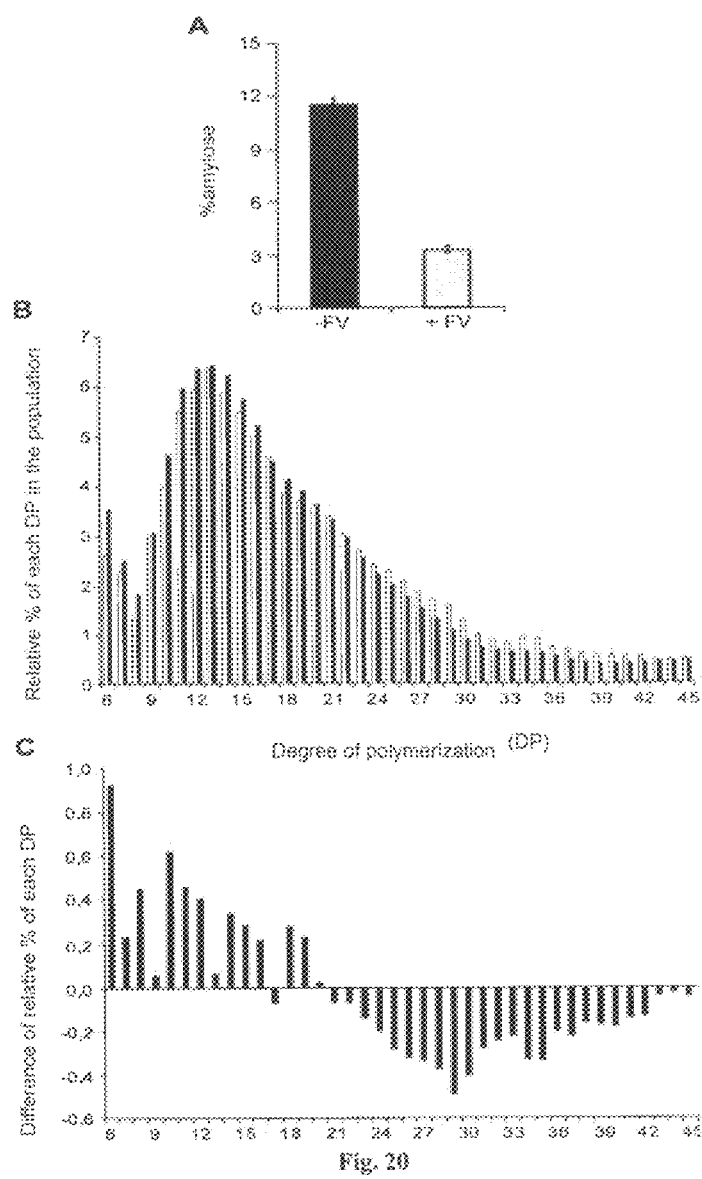

FIG. 20: The fungal volatiles promote both the reduction of the amylose content and changes in the amylopectin composition.

Panel (A): Percentage of amylose with respect to the amylopectin in leaves of potato plants cultured in the presence (+FV) and absence (−FV) of fungal volatiles emitted by A. alternata grown in solid MS medium supplemented with 90 mM sucrose.

Panel (B): Chain length distribution profiles (degree of polymerization: GP) in purified debranched amylopectin from leaves of potato plants cultured in the presence and absence of FVs (black and white bars, respectively).

Panel (C): Difference between the chain length distributions of purified debranched amylopectin of leaves cultured in the presence and in the absence of fungal volatiles emitted by A. alternata grown in solid MS medium supplemented with 90 mM sucrose, calculated as the difference between the profiles in the presence of FVs minus the profile in the absence of FVs.

Figure 21:
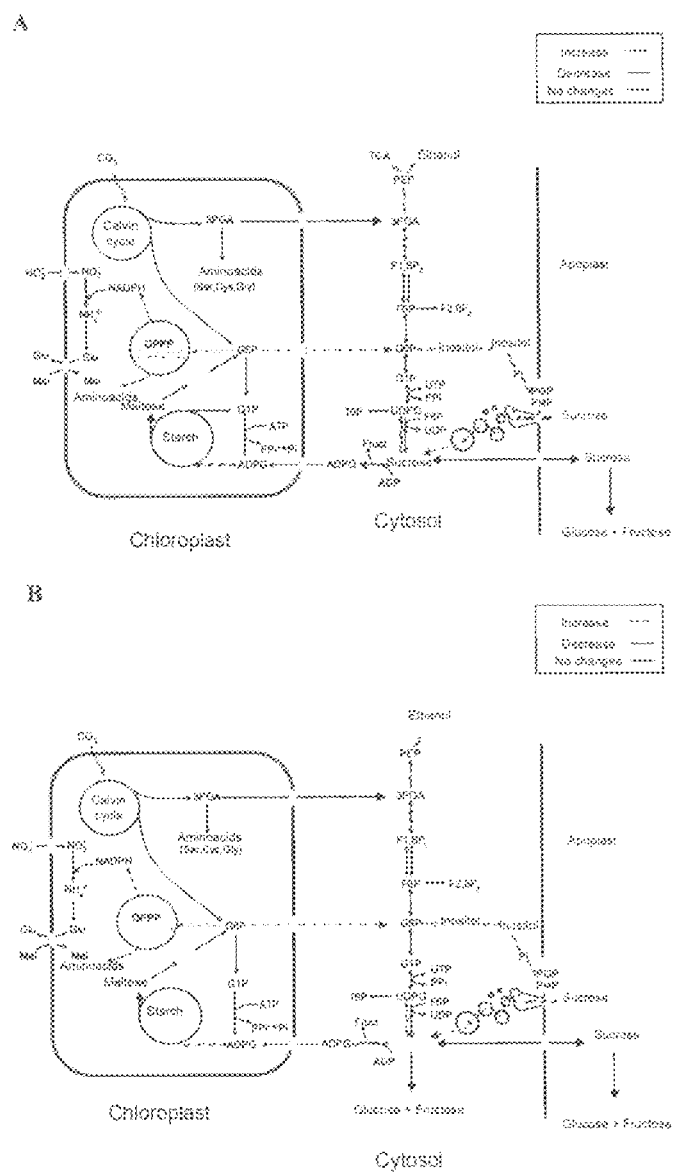

FIG. 21: Schematic depiction of the main carbohydrate metabolism pathways which occur during MIVOISAP according to the alternative view of starch biosynthesis. Panel A depicts the situations which most likely occur when the plants are cultured in heterotrophic conditions, whereas Panel B depicts situations which most likely occur when the plants are cultured in autotrophic conditions. The changes in the expression of genes encoding major carbohydrate metabolism enzymes are indicated by means of variations in the grayscale and in line continuity (discontinuous gray lines, increase; continuous gray lines, reduction; black lines, no significant differences).

Figure 22:
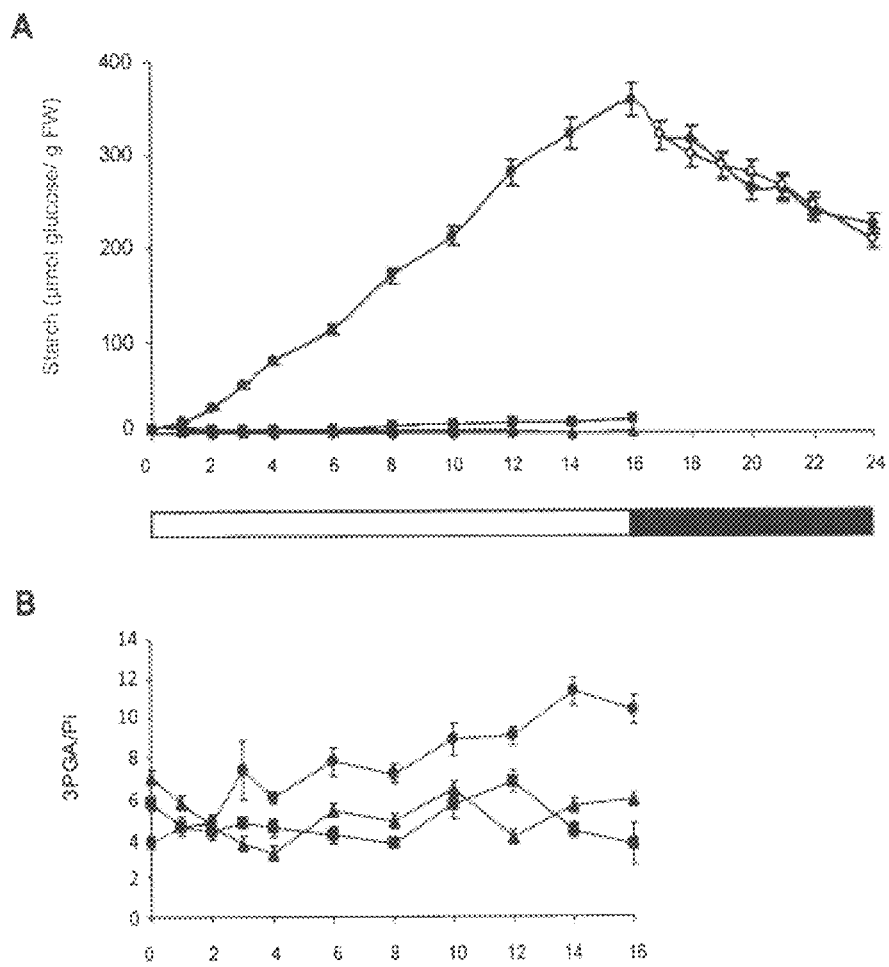

FIG. 22: Kinetics of the starch accumulation and of the balance between the concentration of 3-phosphoglyceric acid (3PGA) and orthophosphate (Pi) in Arabidopsis thaliana plants.

Panel A: quantification of the starch content in leaves of Arabidopsis thaliana plants according to the time elapsed, expressed in hours on the x-axis, of exposure to light or to darkness and the absence or presence of fungal volatiles. The white bar under the graph indicates the light period (first 16 hours), whereas the darkness shaded bar indicates the darkness period (following 6 hours). The starch is expressed as micromoles (μmol) of glucose per gram of fresh weight (FW)

Panel B: ratio between the concentration of 3-phosphoglyceric acid (3PGA) and phosphoric acid (Pi) according to the hours of culture elapsed.

In both panels, the symbols located on each of the curves indicate the culture conditions as follows: Black circles: culture in the presence of fungal volatiles during the entire day (the 16 hours of light and the 8 hours of darkness); non-shaded circles: culture in the presence of fungal volatiles for the 16 hours of light; absence of fungal volatiles for the 8 hours of darkness; darkness shaded squares: culture without volatiles, even during light period; darkness shaded triangles: culture with volatiles, in the absence of light during the 24 hours of culture.

Figure 23:
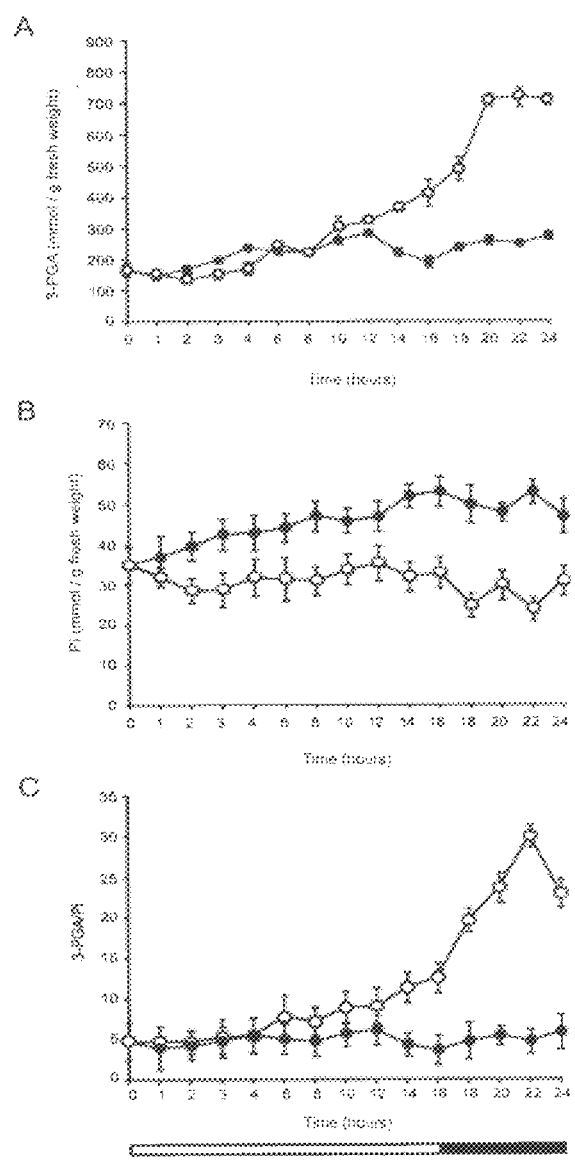

FIG. 23: Kinetics of the levels of 3-phosphoglycerate (3-PGA) (Panel A), orthophosphate (Pi) (Panel B) and of the 3-PGA/Pi ratio in leaves of wild-type Arabidopsis thaliana plants subjected to 16 hours of illumination under white light and 8 hours of darkness for plants grown in an atmosphere with the presence (curves with non-shaded circumferences) or in the absence (curves with shaded circumferences) of fungal volatiles emitted by A. alternata grown in solid MS medium supplemented with 90 mM sucrose.

Figure 24:
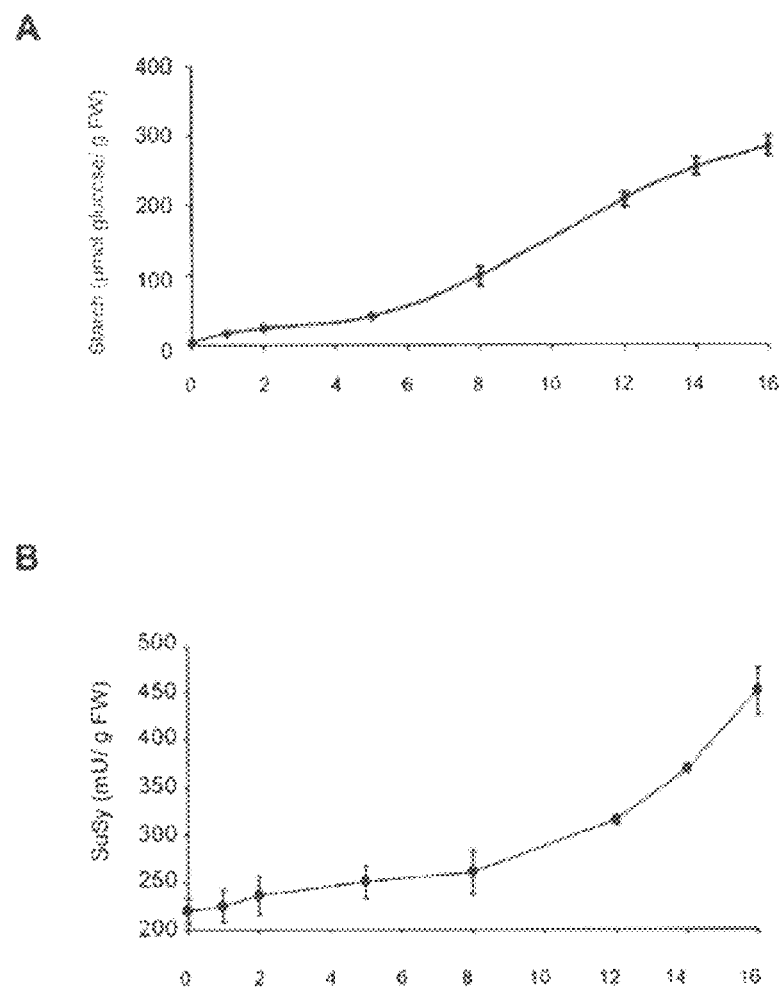

FIG. 24: Kinetics of the starch accumulation and of the sucrose synthase (SuSy) enzyme activity in potato plants.

Panel A: quantification of the starch content in leaves of Arabidopsis thaliana plants according to the time elapsed, expressed in hours on the x-axis, of exposure to the light and to fungal volatiles produced by a culture of Alternaria alternata. The starch is expressed as micromoles (mop of glucose per gram of fresh weight (FW).

Panel B: quantification of the sucrose synthase (SuSy) enzyme activity, expressed in milliunits (mU) per gram of fresh weight (FW), detected in leaves of Arabidopsis thaliana plants according to the time elapsed, expressed in hours on the x-axis, of exposure to the light and to fungal volatiles produced by a culture of Alternaria alternata.

Figure 25:
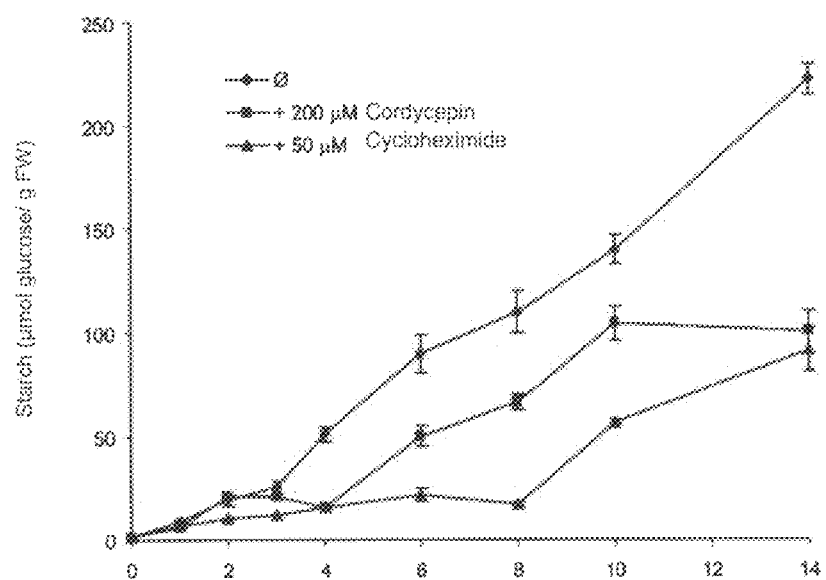

FIG. 25: Kinetics of the starch accumulation in cut leaves of Arabidopsis incubated in Petri dishes with solid MS medium with 90 mM sucrose and in the presence or absence of 50 μM of cycloheximide (Sigma) or 200 μM of cordycepin (Sigma). The dishes were deposited in a 500 cubic centimeter box in which a culture of A. alternata had previously been introduced.

Figure 26:
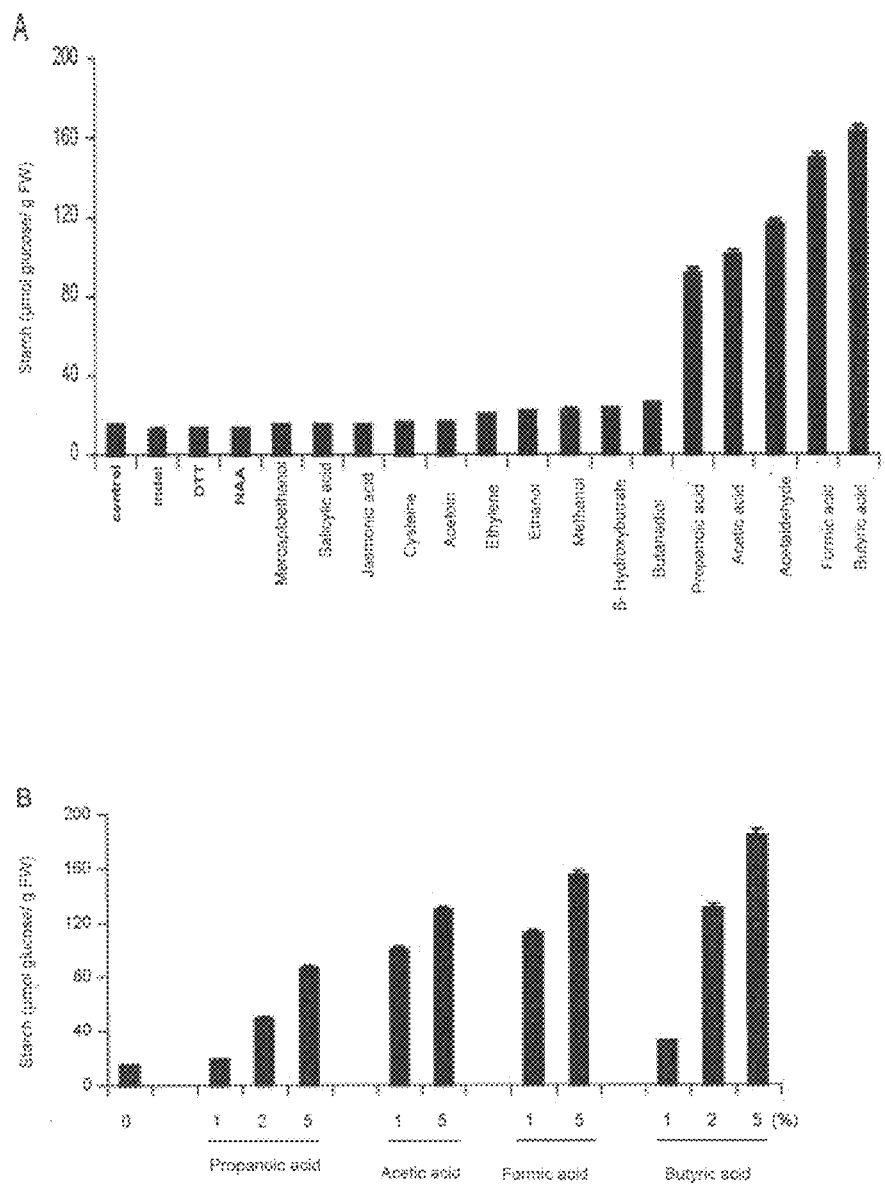

FIG. 26: Quantification of the starch obtained from Arabidopsis thaliana plants incubated in the presence of different volatile compounds:

Panel A: quantification of the starch content in leaves of Arabidopsis plants, cultured in an atmosphere in which the volatile compounds indicated under each of the bars (indol, DTT (dithiothreitol), NAA (1-naphthaleneacetic acid), β-mercaptoethanol, salicylic acid, jasmonic acid, cysteine, acetoin, ethylene, ethanol, methanol, β-hydroxybutyrate, butanediol, propanoic acid, acetic acid, acetaldehyde, formic acid or butyric acid) are present through evaporation of a solution containing them.

Panel B: quantification of the starch content in leaves of Arabidopsis plants, cultured in an atmosphere in which the volatile compounds indicated under each group of bars (propanoic acid, acetic acid, formic acid, butyric acid) are present due to the evaporation of a solution containing them in the percentage, expressed in volume/volume, indicated by means of a number under each of the bars.

In both cases, the starch is expressed as micromoles (μmol) of glucose per gram of fresh weight (FW)

Figure 27:

FIG. 27: Photograph of control Arabidopsis plants and plants cultured for 4 days in solid MS medium inside a 500 cubic centimeter plastic box together with 2 cubic centimeters of a 0.2% formic acid solution. The presence of formic acid clearly promotes the growth of the plant and flowering.

Figure 28:
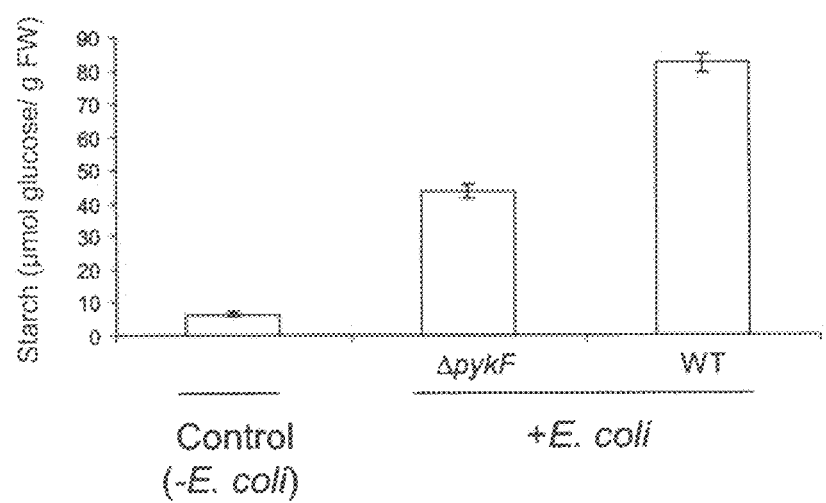

FIG. 28: quantification of the starch content in leaves of Arabidopsis plants, cultured in an atmosphere in which the volatile compounds produced by a culture of Escherichia coli existing in the same sealed box are present or absent (control), without there being any physical contact with the plant, depending on if the culture of Escherichia coli is a wild-type culture (bars with the legend WT) or a mutant with a deletion in the pyruvate kinase F gene (bars with the legend ΔpykF). The starch is expressed as micromoles (μmol) of glucose per gram of fresh weight (FW)

Figure 29:
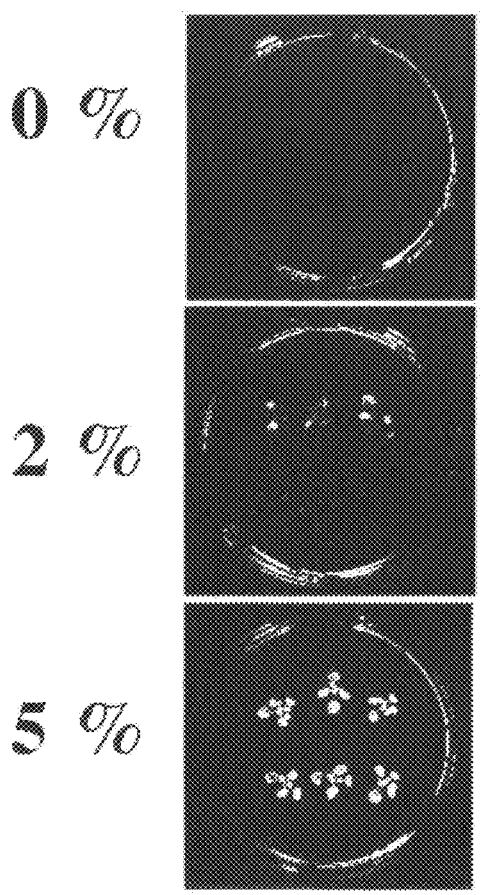

FIG. 29: Photographs of Arabidopsis plants cultured for 4 days in solid MS medium inside a 500 cubic centimeter plastic box together with 2 cubic centimeters of water (top photograph, marked as 0%) or 2 cubic centimeters of a 2% aqueous solution of ammonia (middle photograph) or a 5% aqueous solution of ammonia (bottom photograph), v/v. The presence of ammonia clearly entails leaf depigmentation and inhibits the growth of the plants.

Figure 30:
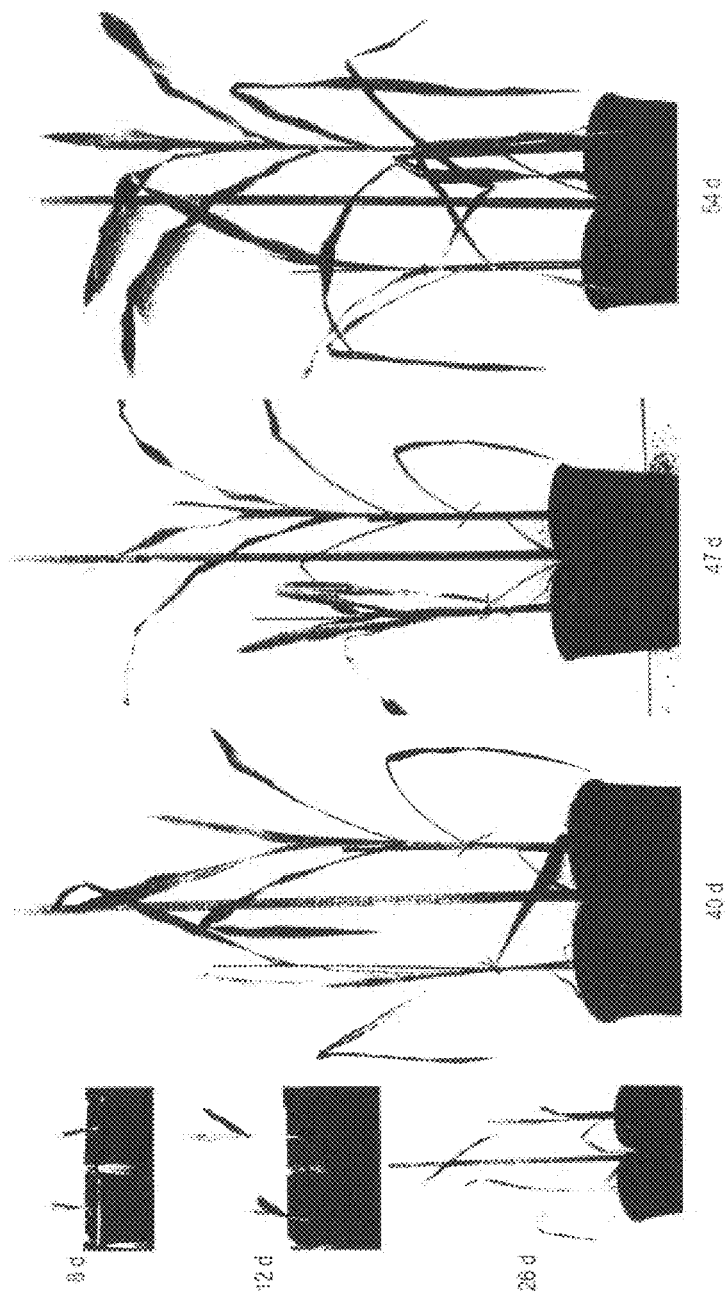

FIG. 30: photographs of maize plants grown together with a culture of *Alternaria alternata*, without there being any contact between the plant and the fungus (plant on the right in all the photographs) and maize plants grown in control conditions in the absence of fungal volatiles. The numbers next to each photograph indicate the days elapsed from the start of the culture.

Figure 31:
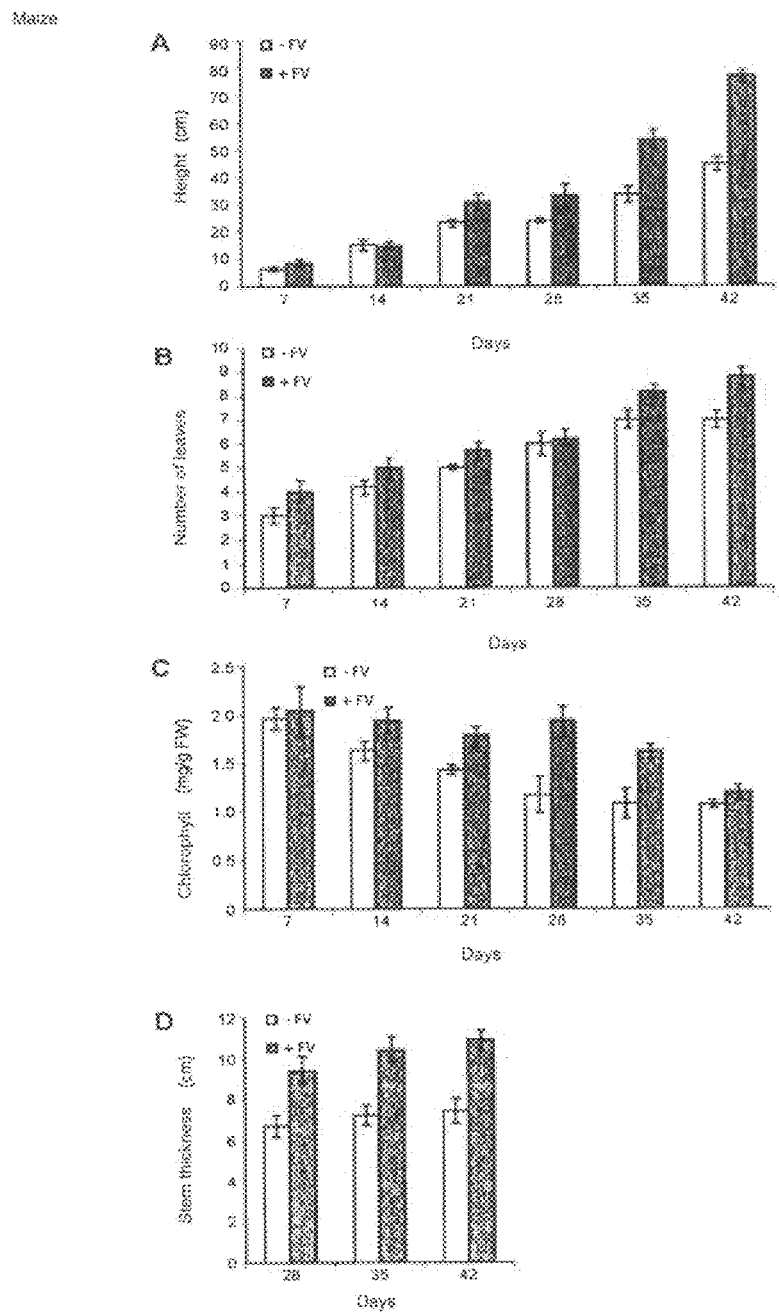

FIG. 31: effect of the presence (+FV) or absence (−FV) of the fungal volatiles on the height (panel A), the number of leaves (panel B), the amount of chlorophyll accumulated with respect to the fresh weight (milligrams per gram of fresh weight) (panel C) and the stem thickness (panel D) in maize plants cultured once the culture time indicated in days on the x-axis has elapsed when the plants are cultured in the presence of a culture of the *Alternaria alternata* fungus (gray shaded bars) or in the absence thereof (white bars, without shading).

Figure 32:
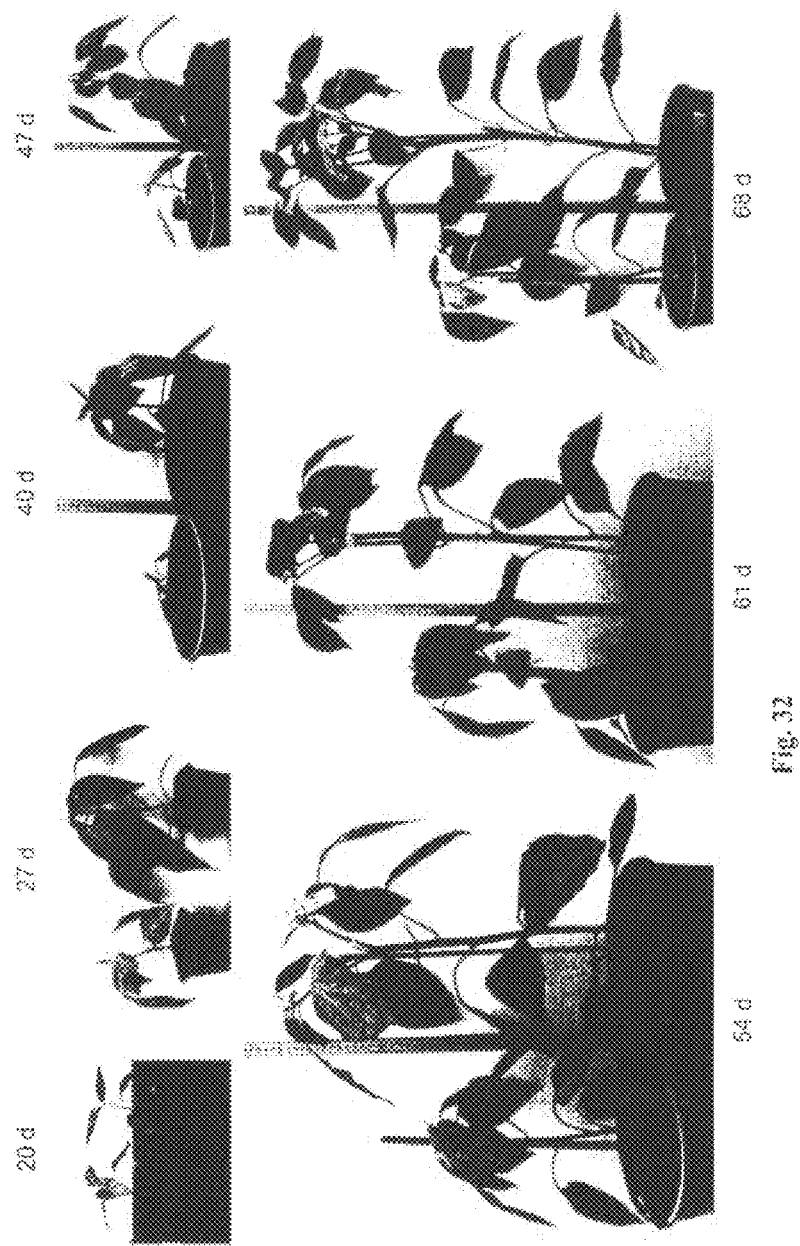

FIG. 32: photographs of pepper plants grown together with a culture of *Alternaria alternata*, without there being any physical contact with said culture (plant on the right in all the photographs) and pepper plants grown in control conditions in the absence of fungal volatiles. The numbers next to each photograph indicate the days elapsed from the start of the culture.

Figure 33:
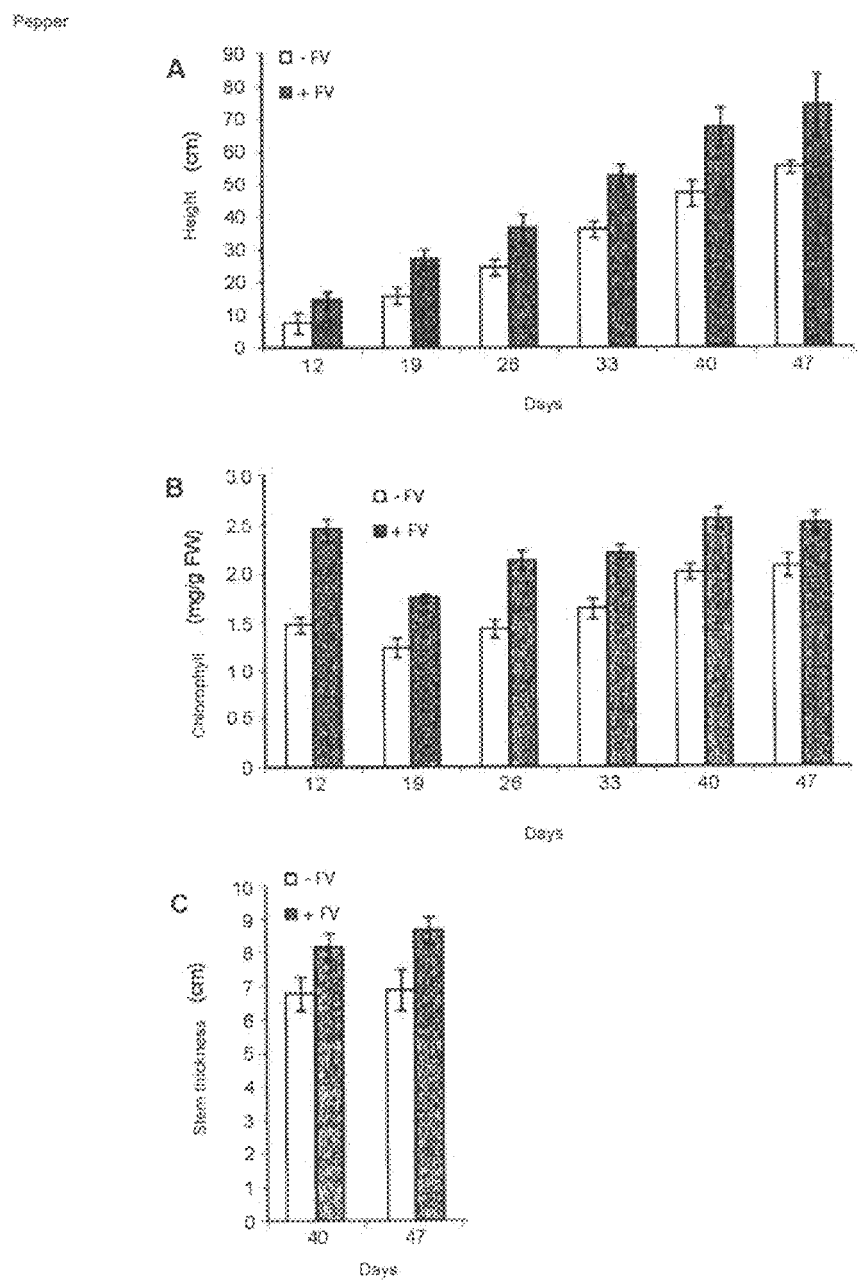
Figure 33:
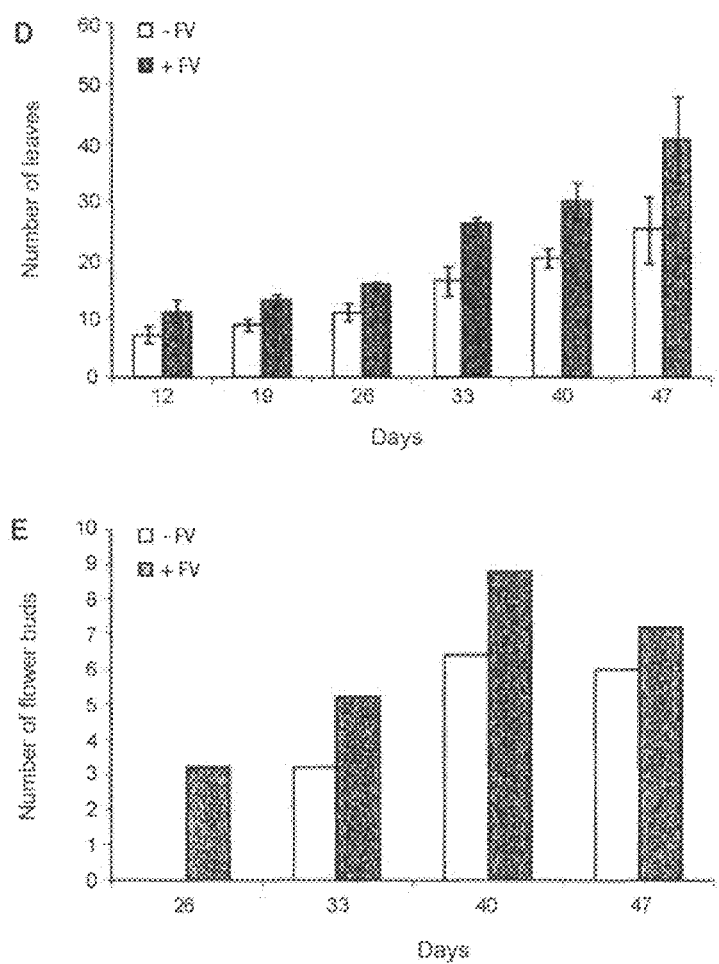

FIG. 33: effect of the presence (+FV) or absence (−FV) of the fungal volatiles on the height (panel A), the amount of chlorophyll accumulated with respect to the fresh weight (milligrams per gram of fresh weight) (panel B), the stem thickness (panel C), the number of leaves (panel D) and the number of flower buds (panel E) present in cultured pepper plants once the culture time indicated in days on the x-axis has elapsed when the plants are cultured in the presence of a culture of the *Alternaria alternata* fungus (gray shaded bars) or in the absence of the same (white bars, without shading).

Figure 34:
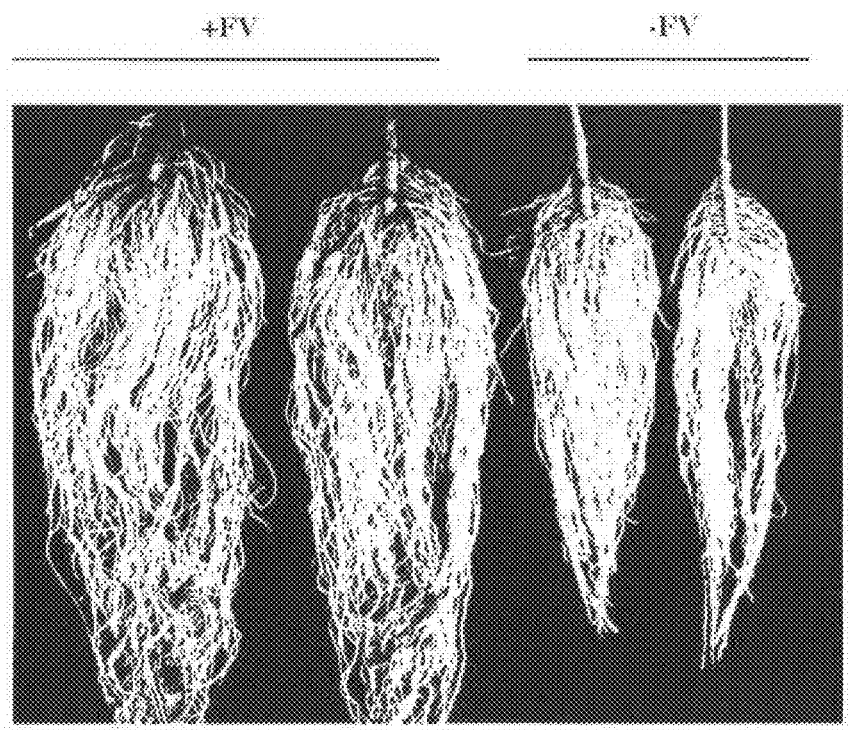

FIG. 34: photographs of roots of pepper plants grown together with a culture of *Alternaria alternata*, without there being any physical contact with said culture (pair of roots located more to the left, marked as "+FV") and of pepper plants grown in control conditions in the absence of fungal volatiles emitted by *Alternaria alternata* (pair of roots located more to the right, marked as "−FV") after 40 days of culture.

Figure 35:
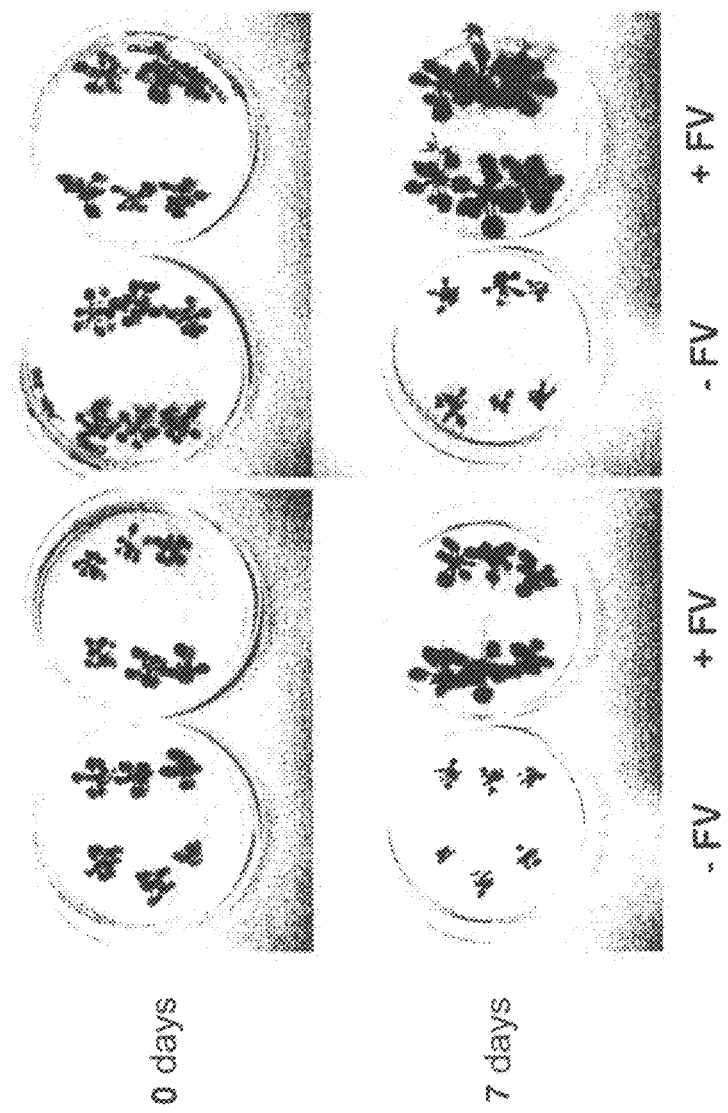

FIG. 35: photographs showing the increase in resistance to water stress of the plants growing in an atmosphere in which microbial volatiles are present, with respect to those that grow in the absence of said volatiles. On day 0 of culture, the plants growing in the absence of fungal volatiles produced by the *Alternaria alternata* fungus (−FV) show a size similar to that of the plants growing in the presence of fungal volatiles; on day 7 (at which time the water of the culture medium has been reduced quite considerably), the plants treated with fungal volatiles (+FV) show a larger size than the plants growing in the absence of said volatiles (−FV), which indicates higher resistance to water stress.

Figure 36:
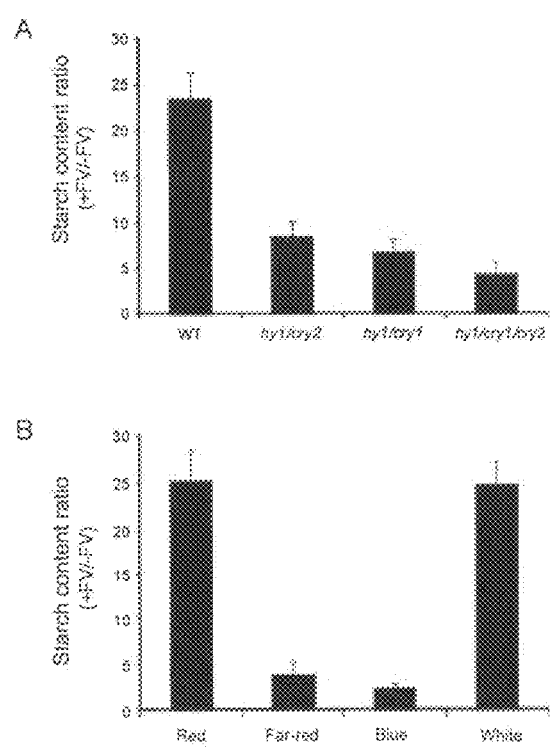

FIG. 36: graphs showing the control of photoreceptors in starch accumulation in *Arabidopsis thaliana* plants. Panel A shows the ratio between the starch content found in plants cultured in the presence of fungal volatiles produced by *Alternaria alternata* (+FV) or in the absence of said volatiles (−FV), for wild-type plants (WT) or hy1/cry2, hy1/cry1 and hy1/cry1/cry2 mutants, cultured in solid MS medium for 16 hours under white light. Panel B also shows the ratio between the starch content found in wild plants cultured in the presence of fungal volatiles produced by *Alternaria alternata* (+FV) or in the absence of said volatiles (−FV), depending on the type of light under which the plants grew (red, far-red, blue or white).

Figure 37:
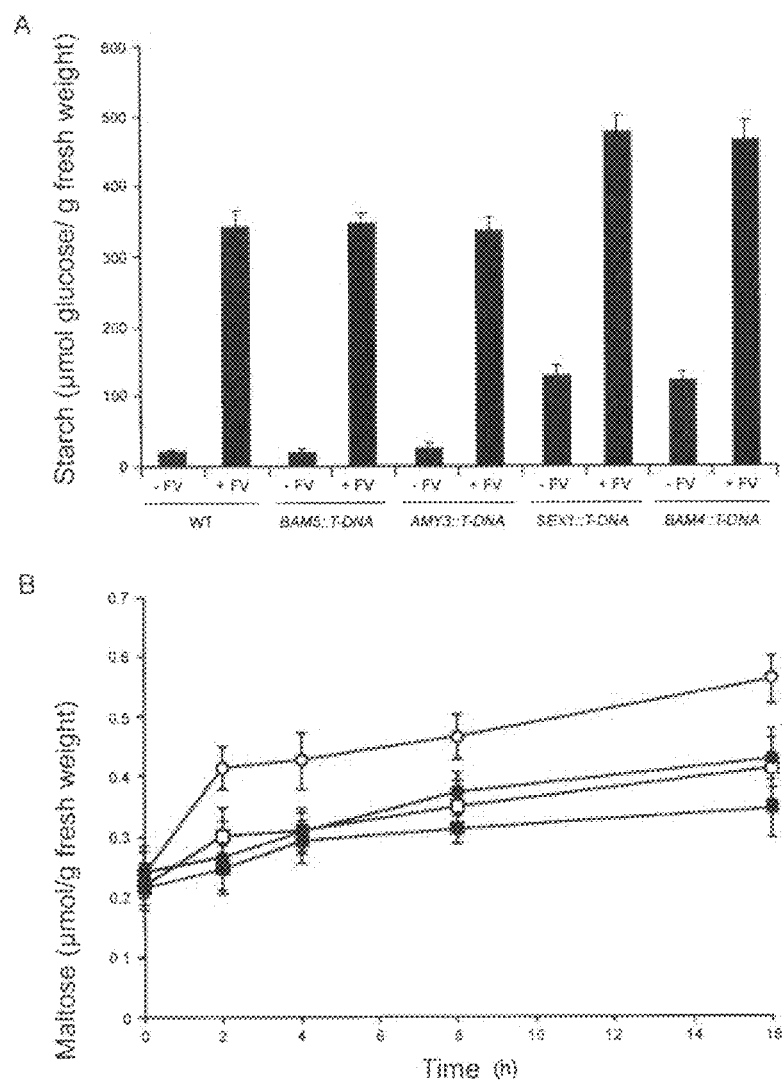

FIG. 37: impact of starch degradation enzymes on starch accumulation promoted by microbial volatiles in *Arabidopsis thaliana* plants. Panel A shows the starch content (expressed as micromoles of glucose per gram of fresh weight) of leaves grown in the absence (−FV) or in the presence (+FV) of fungal volatiles produced by *Alternaria alternata*, of wild-type plants (WT) or T-DNA insertion mutants in the genes of enzymes involved in starch degradation: BAM5, AMY3, SEX1, BAM4, after 16 hours of illumination with white light. Panel B shows the maltose content (expressed as micromoles thereof per gram of fresh weight) observed in wild-type plants cultured in the presence (non-shaded circumferences) or in the absence (shaded circumferences) of fungal volatiles produced by *Alternaria alternata*, as well as in the BAM4 T-DNA insertion mutant (non-shaded and shaded squares in plants grown in the presence or absence of fungal volatiles, respectively), for 16 hours of illumination; the results depicted are the mean±standard deviation of three independent experiments.

Figure 38:
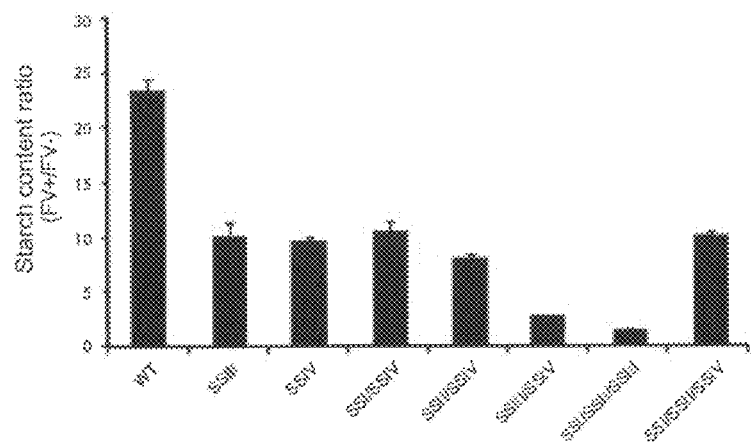

FIG. 38: ratio between the starch content detected in plants cultured for 16 hours in solid MS medium under white light in the presence (+FV) of fungal volatiles produced by *Alternaria alternata* with respect to that obtained in the absence of said volatiles. The increases in the starch content detected in wild-type plants (WT) and T-DNA insertion mutants SSII, SSIV, SSI/SSIV, SSII/SSIV, SSIII/SSIV, SSI/SSII/SSIV and SSI/SSII/SSIII are shown, expressed as the mean±standard deviation of three independent experiments.

Figure 39:
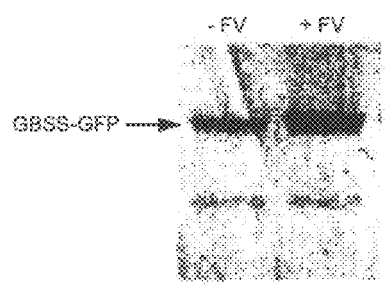

FIG. 39: photograph corresponding to the analysis of the presence of GFP (green fluorescent protein) in Western type blotting in leaves of *Arabidopsis thaliana* plants which expressed a GBSS-GFP fusion protein cultured for 16 hours in the presence (FV+) or absence (FV−) of fungal volatiles emitted by *A. alternata* grown in solid MS medium supplemented with 90 mM sucrose. Protein extracted from the starch existing in the same amount of plant extract (30 micrograms of total protein) was loaded in both lanes.

Figure 40:
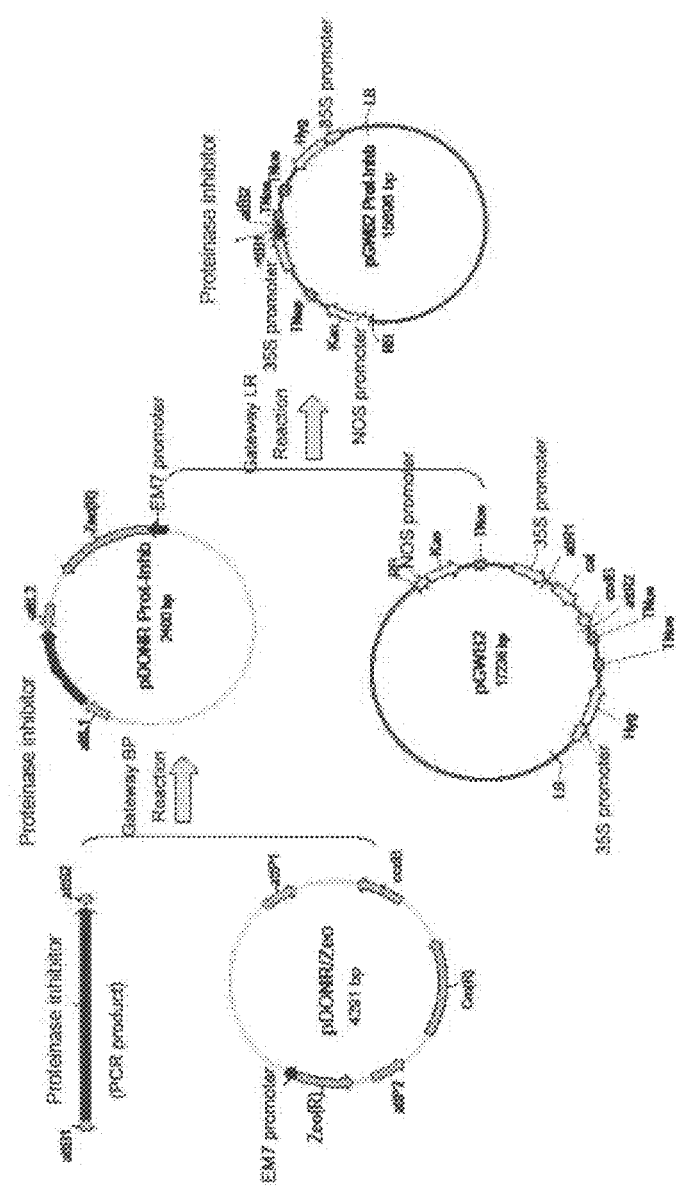

FIG. 40: process for producing plasmids useful for the transformation of plants by means of Gateway technology, containing the coding sequences which are indicated in the top left part of the schemes, from PCR products incorporating the attB1 and attB2 recombinase recognition sequences. Panel A: protease inhibitor; Panel B: antisense nitrite reductase; Panel C: antisense cysteine synthase.

Figure 41:
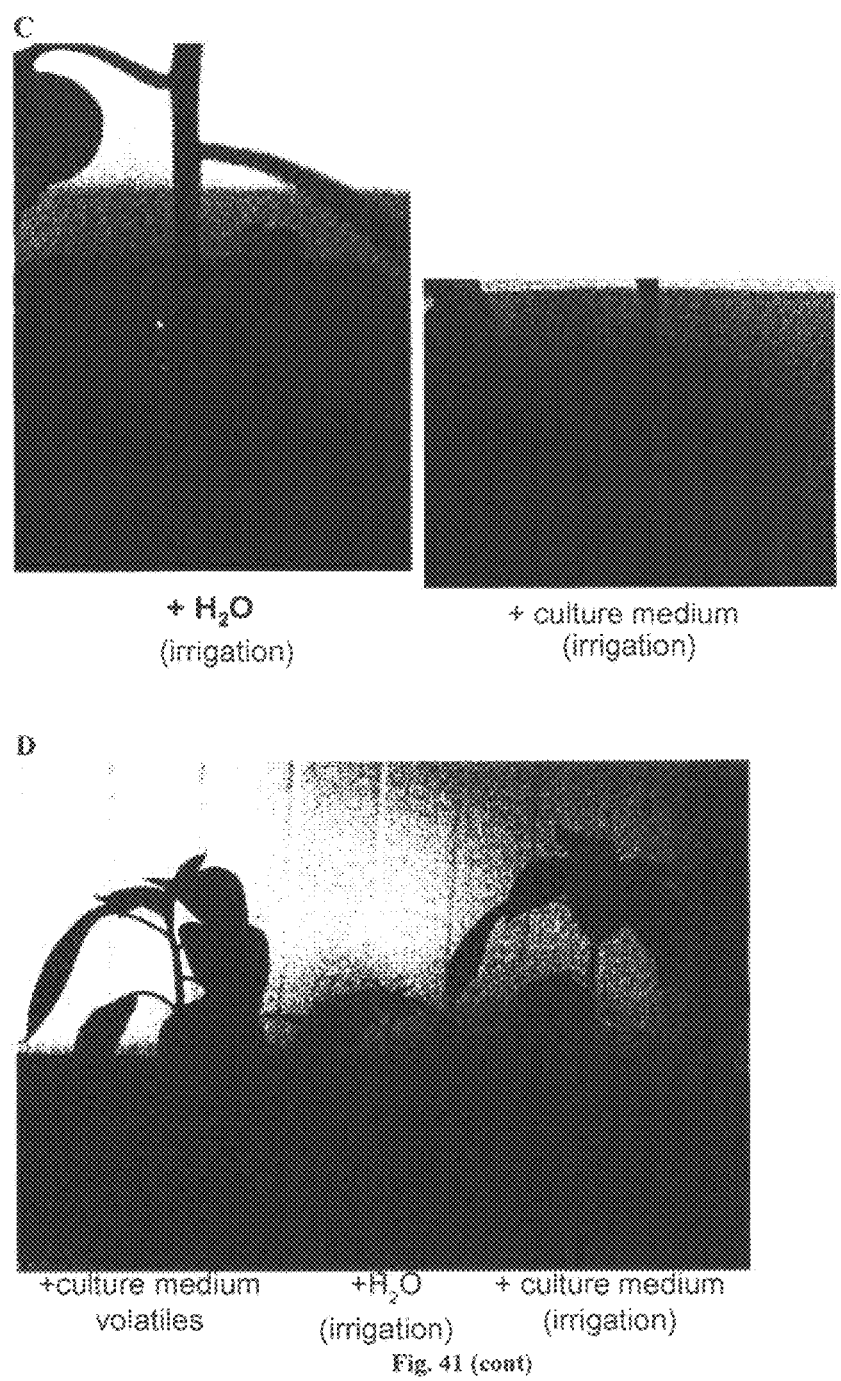

FIG. 41: Effect of the microbial volatiles supplied in the irrigation water. Panels A and B correspond to 3-week old pepper plants irrigated with the medium obtained after leaving a mycelium of *Alternaria alternata* for 2 days in liquid MS (photographs with the legend "culture medium") or with water (marked with the label "+H$_2$O"). The plants of Panels C and D are 45 days old. A plant irrigated with water but cultured for 2 weeks next to a recipient containing filtered "culture medium" of *A. alternata* (plant with the legend "+volatiles of the culture medium") can be seen in the last photograph (panel D).

Figure 42:
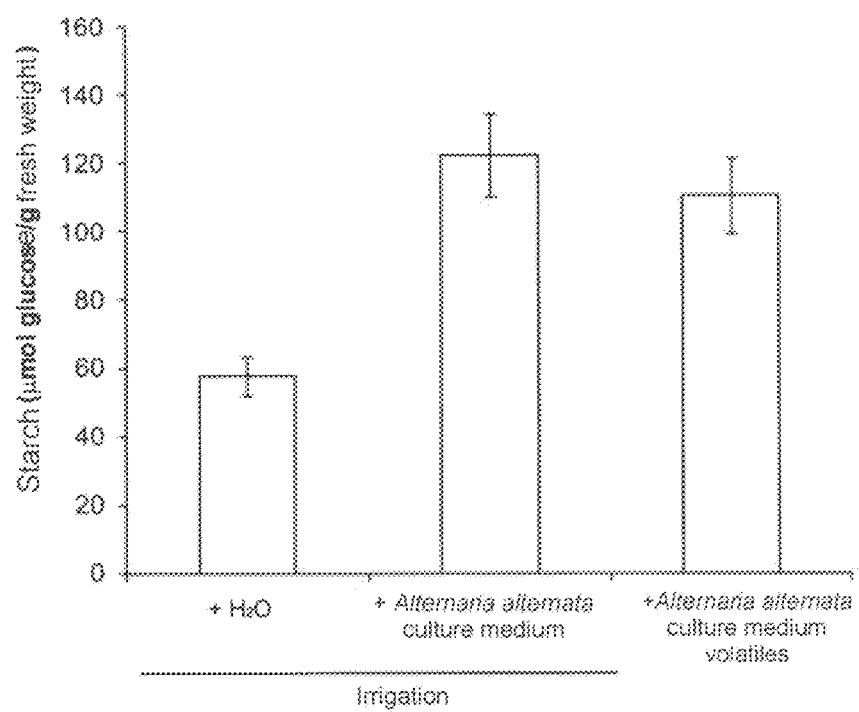

FIG. 42: Graph showing starch accumulation in pepper plants irrigated with water (bar "+H$_2$O"), with the medium obtained after leaving a mycelium of *Alternaria alternata* (bar with the legend "+culture medium of *Alternaria alternata*") for 2 days in liquid MS or irrigated with water but cultured for 2 weeks next to a recipient containing filtered "culture medium" of *A. alternata* (bar with the legend "+volatile of the culture medium of *Alternaria alternata*").

EXAMPLES

The examples of the present application include assays conducted with the following materials and methodological techniques:

Plants, Microbial Cultures, Growth Conditions and Sampling

This work was performed using *Arabidopsis thaliana* (cv. Columbia), potato (*Solanum tuberosum* L. cv Desiree), tobacco (*Nicotiana tabacum*), maize (*Zea mays*, cv. HiII), barley (*Hordeum vulgare* cv. Golden promise) and pepper (*Capsicum annuum*, cv. Dulce italiano) plants.

The *Arabidopsis thaliana* mutants shown in the following table were used, in which table the NASC abbreviations refer to the European *Arabidopsis* Stock Center (http://arabidopsis.info/) as the source of origin of the mutants, and the complete references mentioned in the second to last column are the following: Fulton et al., (2008): Plant Cell 20, 1040-1058; Laby et al. (2001): Plant Phyisiol. 127, 1798-1807; Yu et al. (2001): J. Biol. Chem. 280, 9773-9779; Yano et al. (2005): Plant Physiology 138:837-846; Michalska et al. (2009): Proc. Natl. Acad. Sci. USA 106(24): 9908-9913.

TABLE 1

*Arabidopsis thaliana* mutants used

| Mutant | Locus | Description | Reference | Source |
|---|---|---|---|---|
| hy1/cry2 | At26670/ At1g04400 | Deficient in photoactive PHY and in CRY | | NASC (N9856) |
| hy1/cry1 | At26670/ At4g08920 | Deficient in photoactive PHY and in CRY | | NASC (N9855) |
| hy1/cry1/cry2 | At26670/ At4g08920/ At1g04400 | Deficient in photoactive PHY and in CRY | | NASC (N3732) |
| bam4 | At5g55700 | Lacks plastidial β-amylase isoform 4 | Fulton et al.(2008) | NASC (N660386) |
| bam5 | At4g15210 | Lacks extraplastidial β-amylase isoform 5 | Laby et al. (2001) | NASC (N532057) |
| amy3 | At1g69830 | Lacks plastidial β-amylase | Yu et al. (2005) | NASC (N65602) |
| sex1 | At1g10760 | Lacks α-glucan and water dikinase | Yano et al. (2005) | NASC (N3093) |
| ntrc | At2g41680 | Deficient in plastidial NADP-thioredoxin reductase C | Michalska et al.(2009) | Dr. Cejudo |

In order to culture them, the plants were initially cultured in Petri dishes containing solid MS medium with or without 90 mM sucrose and the indicated supplement with amino acids. The plants were grown in growth chambers with a photoperiod of 16 h of light (300 µmol of photons $s^{-1}$ $m^{-2}$) and at a constant temperature of 24° C.

In the specific case of plants in which the response to continuous monochromatic red light (600-700 nm), far-red light (680-740 nm) or blue light (400-520 nm) was checked, the plants were grown for 16 hours in a growth chamber equipped with a 400 W Son-T Agro halogen lamp (Royal Philips Electronics) filtered through a layer of one of the following polycarbonate filters: Supergel 19 for red light, Supergel 27 for far-red light and Supergel 69 for blue light (Rosco Ibérica SA, Madrid, Spain). The halogen lamp provided a photosynthetically active radiation of 560 $\mu E \cdot m^{-2} \cdot ^{-1}$. The photosynthetically active radiation under the different monochromatic lights was 283, 80 and 76 $\mu E \cdot m^{-2} \cdot s^{-1}$ for the filters which gave rise to red light, far-red light and blue light, respectively.

*E. coli* BW25113, *A. tumefaciens* EHA105 and GV2260, *Salmonella enterica* LT2, *Bacillus subtilis* 168 (*Bacillus* Genetic Stock Center, Ohio State University, Columbus) and *Pseudomonas syringae* 1448A9, 49a/90 and PK2 were cultured in Petri dishes containing solid M9 minimal medium (95 mM $Na_2HPO_4$/44 mM $KH_2PO_4$/17 mM NaCl/37 mM $NH_4Cl$/0.1 mM $CaCl_2$/2 mM $MgSO_4$, 1.5% bacteriological agar) supplemented with 50 mM glucose. *S. cerevisiae* NA33 were cultured in plates containing solid LB medium (1% tryptone, 1% NaCl, 0.5% yeast extract and 1.5% bacteriological agar) supplemented with 50 mM glucose. The *Penicillium charlessi* and *Penicillium* aurantiogriseum colonies or the *Alternaria alternata* colonies were cultured in Petri dishes containing solid MS medium supplemented with 90 mM sucrose.

The microbial cultures were placed in sterile plastic boxes and were sealed. After two days, the Petri dishes containing completely developed plants were placed in 500 cubic centimeter grow boxes. In the cases in which the effect of the fungal volatiles was to be checked, Petri dishes without lids containing microbial cultures were placed in the same grow boxes, as illustrated in FIG. 2. The boxes were sealed and the leaves were harvested after the indicated incubation times to perform the biochemical and transcriptome analyses. As a negative control, Petri dishes containing completely developed plants were cultured in sealed plastic boxes together with Petri dishes which had sterile medium for the culture of microorganisms.

Western Type Blot Analysis

To produce polyclonal antisera against Sus4, a full-length Sus4 encoding cDNA was cloned into the expression vector pET-28b(+) (Novagen) to create pET-SuSy. The BL21(DE3) cells transformed with pET-SuSy were grown in 100 ml of liquid LB medium up to an absorbance at 600 nm of 0.5 and then 1 mM isopropyl-β-D-thiogalactopyranoside was added. After 5 h, the cells were centrifuged at 6,000×g for 10 min. The settled bacteria were resuspended in 6 ml of His-bind binding buffer (Novagen), treated with ultrasound and centrifuged at 10,000×g for 10 min. The supernatant thus obtained was subjected to chromatography in His-bind (Novagen). The eluted His-tagged Sus4 was then rapidly desalted by ultracentrifugation in Centricon YM-10 (Aicon, Bedford, Mass.). The purified protein was electrophoretically separated by preparative 12% SDS-PAGE and stained with Coomassie Blue. An approximately 90 kDa protein band was eluted and used to produce polyclonal antisera by immunizing rabbits.

For immunoblot analyses, protein samples were separated by 10% SDS-PAGE, transferred to nitrocellulose filters, and immunodecorated by using antisera obtained against either maize AGP or potato SuSy as the primary antibody, and a goat anti-rabbit IgG-alkaline phosphatase conjugate (Sigma) as the secondary antibody. In the case of Western type blots of AGP, samples were extracted and separated in SDS-PAGE under reducing/non-reducing conditions essentially as described by Kolbe et al. (Kolbe et al., 2005: Proc. Natl. Acad. Sci. USA 102: 11118-11123).

For the analysis of the GBSS-GFP fusion protein, the sediments obtained from a plant homogenate (10 mg of fresh weight) were obtained as extracts after a centrifugation step at 10000×g. Such extracts contain starch to which the GBSS, and with it the GBSS fusion protein, binds. The extracts were separated by 10% SDS-PAGE and transferred to nitrocellulose filters. The detection of the GBSS protein associated with GFP was carried out using a specific anti-GFP commercial antibody obtained in rabbits (ab290, AbCam), following the Western Blot methodology described by Towbin et al. (Towbin et al., 1979). The antigen-antibody complex was detected by means of incubation with a secondary goat anti-rabbit IgG-alkaline phosphatase conjugate antibody (Sigma) as the secondary antibody.

Enzyme Assays

All the enzymatic reactions were carried out at 37° C. 1 g of frozen leaf powder was resuspended at 4° C. in 5 ml of 100 mM HEPES (pH 7.5) and 2 mM EDTA. When indicated, 5 mM DTT was added to the extraction buffer. The suspension was desalted and assayed for enzymatic activities. AGP, SuSy, acid invertase, PPase and total SS activities were assayed as described by Baroja-Fernández et al. (Baroja Fernández et al., 2009: Plant Cell Physiol. 50: 1651-1662). β-amylase was assayed as described by Liu et al. (Liu et al., 2005: Chemosphere 61: 293-301). SBE activity was measured as a decrease in absorbance of the amylose-iodine complex as described by Vos-Scheperkeuter et al. (Vos Scheperkeuter et al., 1989: Plant Phylio. 90: 75-84). Nitrite reductase was measured following the method described by Rao et al. (Rao et al., 1981: Plant Cell Physiol, 22: 577-582). pG6PDH was measured according to Hauschild et al. (Hauschild et al., 2003: Plant Physiol. 133: 47-62). Cytosolic fructose-1,6-bisphosphatase was assayed as described by Lee and Hahn (Lee and Hahn, 2003: Plant Cell Rep. 21:611-618). One unit (U) is defined as the amount of enzyme that catalyzes the production of 1 μmol of product per min.

Determination of ADPG, UDPG and 3-phosphoglycerate

A 0.5 g aliquot of the plant tissue powder frozen in liquid nitrogen was resuspended in 4 ml of 1.0 M $HClO_4$, left at 4° C. for 2 h and centrifuged at 10,000 g for 5 min. The supernatant was neutralized with 5 M $K_2CO_3$, centrifuged at 10,000 g and subjected to nucleotide-sugar measurement analyses as described by Muñoz et al. (Muñoz et al., 2005: Plant Cell Physiol. 46: 1366-1376) by HPLC in a system obtained from P. E. Waters and Associates fitted with a Partisil-10-SAX column. 3-phosphoglycerate was measured as described by Muñoz et al. (2005).

Analytical Methods

Starch was measured using an amyloglucosidase-based test kit (acquired from Boehringer Mannheim, Germany, except in the case of assays conducted with *Arabidopsis thaliana* mutants, in which case it was acquired from Sigma-Aldrich Chemical Co, St. Louis, Mo., USA). The amylose content of the starch was measured iodometrically according to Hovenkamp-Hermelink et al. (Hovenkamp-Hermelink et al., 1988: Potato Res. 31: 241-246). Analysis of the side chain distribution of isolated starch was carried out by means of HPAEC-PAD essentially as described by Abel et al. (Abel et al., 1996: Plant J. 10: 981-991) using a DX-500 system (Dionex) fitted with a CarboPac P A 10 column. Maltose was measured as described by Ezquer et al. (Ezquer et al. 2010: Plant Cell Physiol. 51:1674-1693). Chlorophyll was measured as described in Wintermans and De Mots (Wintermans, J. F. G. M. and de Mots. A. (1965). Biochim. Biophys. Acta 109: 448-453). The levels of 3-PGA and Pi were determined as described by Lytovchenko et al. (Lytovchenko, et al., 2002. Planta 215: 802-811).

In all cases, the results shown correspond to the mean±standard deviation of 3 independent experiments.

Microarrays

Total RNA was extracted from frozen potato leaves using the Trizol method according to the manufacturer's procedure (Invitrogen), followed by purification with an RNeasy kit (Qiagen). RNA amplification, labeling and statistical data analysis were performed basically as described by Adie et al. (Adie et al., 2007: Plant Cell 19: 1665-1681). Agilent POCI 4×44K microarray slides (015425) (G2519, Agilent Technologies) containing 246,000 expressed sequence tags corresponding to 46,345 unigenes (http://pgrc.ipk-gatersleben.de/poci) were used for hybridization (Kloosterman et al. 2008: Funct Integr. Genomcs 8: 329-340). Labeling and hybridization conditions were those described in "the two color microarray based gene expression analysis" manual of Agilent Technologies. Three independent biological replicates were hybridized for the leaves of plants treated with microorganisms and of the control plants. Images of the Cy3 and Hyper5 channels were equilibrated for intensity differences and captured with a GenePix 4000B scanner (Axon). Spots were quantified using GenPix software (Axon) and normalized using the Lowess method. The means of the three replicate log-ratio intensities and their standard deviations were calculated, and the expression data were statistically analyzed using the LIMMA Package (Smyth and Speed, 2003: Methods 31: 265-273). Functional characterization of the differentially expressed genes was done using the Mapman tool (http://gabi.rzpd.de/proiects/MapMan/).

Real-Time Quantitative PCR

Total RNA was extracted from potato leaves as was done for microarray experiments. The RNA was treated with RNase-free DNase (Takara). A 1.5 μg aliquot of RNA was reverse transcribed using polyT primers and the Expand Reverse Transcriptase kit (Roche) according to the manufacturer's instructions. RT-PCR reaction was performed using a 7900HT sequence detector system (Applied Biosystems) with the SYBR Green PCR Master Mix (Applied Biosystems) according to the manufacturer's protocol. Each reaction was performed in triplicate with 0.4 μl of the first-strand cDNA in a total volume of 200 μl. The specificity of the PCR amplification was checked with a heat dissociation curve (from 60 to 95° C.). Comparative threshold values were normalized to an 18S RNA internal control and compared to obtain relative expression levels. The specificity of the obtained RT-PCR products was controlled in 1.8% agarose gels. Primers used for the RT-PCRs are listed below in Table 1:

TABLE 2

Real-time quantitative PCR primers

| Encoded protein | Primers used | SEQ. ID NO. |
|---|---|---|
| SNF4 | Forward: CCCCGTAGATCTCAGAAGCA | 1 |
|  | Reverse: CAGCGTGGCTGTATATGGAA | 2 |
| 1-phosphatidylinositol-4-phosphate 5-kinase | Forward: ACACAAGAAGTGGGGAATGG | 3 |
|  | Reverse: TTTTCTGCTGCCTTCCTAGC | 4 |

TABLE 2 -continued

Real-time quantitative PCR primers

| Encoded protein | Primers used | SEQ. ID NO. |
|---|---|---|
| Pullulanase | Forward: GCGTAAACAATACCGCCAGT | 5 |
| | Reverse: CAGGTCAAACCGAAATCCAT | 6 |
| Triose-phosphate/3-phosphoglycerate translocator | Forward: CAAGATTTCCCCCATTGCTA | 7 |
| | Reverse: TTCCAACCGCATGTGTAAGA | 8 |
| Nitrite transporter | Forward: CAAATACCTCCAGCCAGCAT | 9 |
| | Reverse: TGTGAATCGACGAGCAAAAG | 10 |
| Trehalose-6-phosphate synthase | Forward: CGATTTTCAGTGGATGCAGA | 11 |
| | Reverse: GATGATGCCAAACAAGAGCA | 12 |
| Starch phosphorylase (plastidial isoform) | Forward: AACCAAGTGGACAGGATCTGA | 13 |
| | Reverse: CTTTTGCCTTCCTCCACTCA | 14 |
| β-amylase BMYI | Forward: GAGGTAACACGAGGCTTCCA | 15 |
| | Reverse: CACAACTGCAACCTCTGCAT | 16 |
| Thioredoxin M4 | Forward: AAGTTACCCGTCCTGGTTGA | 17 |
| | Reverse: ACTTGCCAGCGTATTCCTGT | 18 |
| Nitrite reductase | Forward: TGCAGACATTGGATTCATGG | 19 |
| | Reverse: CTCCCAAATGTGAATCACTCC | 20 |
| Cysteine synthase | Forward: TGCCTGCATCAATGAGTCTT | 21 |
| | Reverse: CAGCCTTTGAAACAGCTCCT | 22 |
| Inorganic pyrophosphatase | Forward: ACAGCCCGAAACCCTAGATT | 23 |
| | Reverse: TGAAAACACCATCACCCAAA | 24 |
| Acid invertase | Forward: AATGGAGCAGCACGACTCTT | 25 |
| | Reverse: AGTCTTGCAAGGGGAAGGAT | 26 |
| Glucose-6-phosphate dehydrogenase (plastidial isoform) | Forward: CGAGGAGGGTACTTTGACCA | 27 |
| | Reverse: CAAGCTGACAGGTGTTTCCA | 28 |
| Starch synthase III | Forward: CGAAAGGGTGCGTATATGGT | 29 |
| | Reverse: TCCGGACTAAATCCACCTTG | 30 |
| Inositol-3-phosphate synthase | Forward: CAAGAGGGCAATGGATGAGT | 31 |
| | Reverse: ATTGGAGCAGCCAAAAGAGA | 32 |
| Fructose-2,6-bisphosphatase | Forward: TGGGACAGATGGCACTATCA | 33 |
| | Reverse: ATCCGGGACAATTACTTCCA | 34 |
| 18S RNA | Forward: GGGCATTCGTATTTCATAGTCAGAG | 35 |
| | Reverse: CGGTTCTTGATTAATGAAAACATCCT | 36 |
| Glucose-6-phosphate translocator | Forward: TGACTGGAGATGGATGTGGA | 37 |
| | Reverse: GATGGGAATTGCAGCTAGGA | 38 |
| Protease inhibitor I | Forward: TGAAACTCTCATGGCACGAA | 39 |
| | Reverse: TGGCCAGCTTAGTTTTCCAT | 40 |
| α-glucan branching enzyme | Forward: AATTTGGTGGCCATGGAAG | 41 |
| | Reverse: AGGAATTTGGACGACCATTG | 42 |
| ADP-glucose pyrophosphorylase L3 | Forward: CAGGTGAGGCTAAGTTGAAGG | 43 |
| | Reverse: GAGGGGGAAAAGACGAGTTC | 44 |
| ADP-glucose pyrophosphorylase L1 | Forward: GGTGAAAGATCGCGCTTAGA | 45 |
| | Reverse: CTGCTAACAGGGAGGCAATC | 46 |
| Kunitz-type tuber invertase inhibitor | Forward: AAACCTTCAATGCCCAAATG | 47 |
| | Reverse: ATTCCGACTCCGACTTACGA | 48 |
| Sucrose synthase 4 | Forward: TGGGAATACATCCGTGTGAA | 49 |
| | Reverse: GCTCCGTCGACAAGTTCTTC | 50 |
| Dnak-type chaperone Hsc70 | Forward: TGCAAGCTGCAATCTTGAGT | 51 |
| | Reverse: ACACCTCCAGCAGTCTCCAG | 52 |
| Yeast synthase IV | Direct: CATCGTCTCTTGCGCCTAAT | 53 |
| | Reverse: ATGGCCTTACTGCTGACGTT | 54 |
| Real-SpoT-like RSH4 protein | Direct: ACAAGGGCGGTGTTACTGAT | 55 |
| | Reverse: TCGCCGAAGGAAAATCTCTA | 56 |
| Sedoheptulose-1,7-bisphosphatase | Direct: GAACCATCTTTGGCGTATGG | 57 |
| | Reverse: CATATGTAGTTCGCGGTCCA | 58 |
| Fructose-bisphosphate adolase | Direct: GGAAAGGTATTTTGGCAGCA | 59 |
| | Reverse: GTTGACGAAGTGCTTGACGA | 60 |
| Chloroplast fructose-1,6-bisphosphatase | Direct: TTCGATGGCTTGTAAGCAGA | 61 |
| | Reverse: TTTTGGTCCTCTCCATGAGC | 62 |

TABLE 2 -continued

Real-time quantitative PCR primers

| Encoded protein | Primers used | SEQ. ID NO. |
|---|---|---|
| Cytosolic fructose-1,6-bisphosphatase | Direct: TATCCCGCTGATGGTTCTTC | 63 |
| | Reverse: CTCCGGGGTACAAGAAGATG | 64 |
| Glyceraldehyde-3-phophate dehydrogenase (plastidial isoform) | Direct: CACACCGTGACTTGAGGAGA | 65 |
| | Reverse: CCCTTGAGCTGAGGTAGCAC | 66 |

Iodine Staining and Microscopic Localization of Starch Granules

Leaves harvested at the end of the light period were fixed by immersion in 3.7% formaldehyde in phosphate buffer. Leaf pigments with were then removed with 96% ethanol. Rehydrated samples were stained with iodine solution (KI 2% (w/v) I2 1% (w/v)) for 30 min, were rapidly immersed in deionized water and photographed. Leaves for microscopic starch observation were mounted on microscopic slides and examined by confocal microscopy using an Ar 488 excitation laser. Samples for sectioning were immersed in cryoprotective medium OCT (Tissue-Tec, USA) and frozen at −50° C. 10 µm thick cryosections were obtained in an AS620 cryometer (Shandon, England). After thawing, the sections were stained with iodine solution for 2 min at room temperature, mounted on microscope slides and observed using an Olympus MVX10 stereomicroscope (Japan). Microphotographs were taken with a DP72 video camera (Olympus, Japan) and Cell D software (Olympus, Japan).

Confocal Microscopy

Subcellular localization of GBSS-GFP was performed using a D-Eclipse Cl confocal microscope (NIKON, Japan) equipped with a standard AR 488 excitation laser, a BA515/30 filter for green emission, a BA650LP filter for red emission and a transmitted light detector for bright field images.

Example 1

Volatiles Emitted by Different Microbial Species Promote Changes in Plant Development, Increase in Growth and Starch Accumulation in Leaves from Different Plant Species 1.1. Effect on the Growth To check the possible effects that volatile chemical compounds released by microorganisms could have on plant metabolism, first of all assays were performed with *Arabidopsis* plants cultured in MS medium in the presence or absence of cultures of *Escherichia coli* BW25113, *Agrobacterium tumefaciens* EHA105 and GV2260, *Saccharomyces cerevisiae* NA33, *Bacillus subtilis* 168, *Penicillium charlesii* or *Penicillium aurantiogriseum, Salmonella enterica* LT2, *Alternaria alternata, Pseudomonas syringae* 1448A9, 49a/90 or PK2 and in the absence of physical contact between the plant and culture medium. The arrangement, in all cases, was analogous to that of the photographs of Panels B and D of FIG. 2, including controls with plates with culture medium in which microorganisms had not been seeded analogously to that shown in Panels A and C of FIG. 2.

The preliminary visual analyses showed that volatiles emitted by these microorganisms promote plant growth, as can be observed comparing the first four panels of FIG. 2. This effect was confirmed by checking the fresh and dry weight of *Arabidopsis* plants grown in the absence or in the presence of volatiles emitted by *Alternaria alternata* fungi, as well as other parameters related to plant development such as the number of flowers, branches or pods or shoot height. As can be observed in FIG. 3, all these parameters were increased by the effect of the volatiles, which effect was also observed on the starch content.

This effect is not exclusive to *Arabidopsis* plants, but is observed in other species, as in tobacco plants, as can be observed in FIG. 4, where plants subjected to the effect of volatiles emitted by *Alternaria alternata* fungi show a larger size and greater number of leaves. Roots of tobacco plants also grew more in the presence of *Alternaria alternata* volatiles.

In the specific case of some microorganisms, such as *E. coli*, the fact that this bacterium promotes plant growth appears to contradict the observations made by Ryu et al. (Ryu et al. 2003: Proc. Natl. Acad. Sci. USA 100, 4927-4932), who showed that *E. coli* DH5α does not promote *Arabidopsis* plant growth. Furthermore, these authors showed that the volatiles emitted by *Pseudomonas syringae* exert a negative effect on *Arabidopsis* growth and development. Therefore, it was thought that the variations in growth conditions and assay systems could justify the different results. Specifically, it was considered if the results obtained in *Arabidopsis* by other authors could be due to use of media containing yeast extracts, rich in amino acids, such as LB or Kornberg media, while that the growth of microorganisms in minimal medium could result in no volatile metabolite harmful for the plant being produced.

The assay was repeated using *Salmonella enterica* as the microorganism to check this hypothesis, culturing it either in M9 minimal medium or in LB medium. The results, shown in FIG. 5A, show that the volatiles produced by *Salmonella enterica* grown in LB cause plants to turn yellow and become ill, while if *Arabidopsis* plants grown in M9 minimal medium are compared with control plants maintained in identical conditions, but without any microorganisms having been seeded in the corresponding Petri dish, it is observed that plants grown in the presence of the microorganism are larger and have a greater number of leaves.

Similar results were obtained with other plant pathogens, such as *Agrobacterium tumefaciens*, both with the EHA105 and GV2260 strain (see FIG. 5B) or *Pseudomonas syringae* (see FIG. 5C): the positive effect on growth takes place provided that the pathogen grows in a minimal medium, such as M9 or MOPS, that have inorganic salts as sources of Na, K, Ca, Mg, P, N and S in their composition and that, except sugar used as a carbon source supplement (sucrose or glucose in the examples of the present application) and the bacteriological agar itself, lack other organic compounds, particularly compounds containing organic nitrogen. Volatiles emitted by microorganisms grown in media such as LB, Kornberg or any other medium containing a hidrolisate of yeasts, proteins, or which is rich in amino acids, exert a negative effect (or not as positive as that observed when grown in minimal media) on starch growth and production in the plant, such that plants exposed to such volatiles develop white leaves and ultimately die. All this is probably due to the toxic effect of the ammonium produced by the deamination of the amino acids existing in the medium.

1.2. Effect on Starch Accumulation

Next, starch content of leaves of *Arabidopsis* plants that had been cultured in MS medium in the presence or absence of cultures of *S. cerevisiae* NA33, *B. subtilis* 168, *Salmonella enterica* (LT2), *E. coli* (BW251 13), *A. tumefaciens* EHA105, *A. tumefaciens* GV2260, *Pseudomonas syringae* 1448A9, *Pseudomonas syringae* 49a/90, *Pseudomonas syringae* PK2, *Penicillium aurantiogriseum, Penicillium charlessi* and *Alternaria alternata* was measured. All the microorganisms, except *S. cerivisiae*, were grown in solid M9 medium supplemented with glucose. All, in turn, grew in the absence of physical contact between the plant and culture medium.

The results obtained show that all the microbial species assayed emitted volatile compounds that favorably affected starch accumulation, as was confirmed by means of quantitative measurement analysis of starch using an amyloglucosidase/hexokinase/glucose-6P dehydrogenase test kit (FIG. 6A). This effect is due to the volatiles since (a) the inducing effect is lower in the presence of activated carbon and (b) the effect disappears after 3 days out of contact with the volatile, as can be seen in FIG. 6C.

The difference in starch accumulation was also compared when the *Agrobacterium tumefaciens, Pseudomonas syringae, Penicillium charlesii, E. coli* and *Salmonella enterica* microorganisms were cultured either in M9 minimal medium, or LB medium. As can be seen in FIG. 6B, the "positive" effect of microorganisms on starch accumulation only takes place when they are grown in a minimal medium (M9, MOPS or even MS), while the effect is lower or null when the microorganisms grow in a medium rich with amino acids.

It was additionally checked that starch accumulation was also produced in other organs of *Arabidopsis* plants, such as the stem or the roots, when they were grown in the presence of volatile fungi emitted by *Alternaria alternata* fungi. The samples of the accumulation in these tissues can be observed in Panels D and E of FIG. 6. Panels F and G show the increase in the biomass accumulation produced by the volatile fungi both in leaves and in roots.

The effect of starch accumulation is not exclusive to *Arabidopsis* plants. Furthermore, the positive effect is confirmed if the plants are grown in soil instead of in culture dishes in vitro: the assays performed with maize and *Arabidopsis* plants grown in soil show an increase in leaf size and vigor when grown in the presence of volatile fungi emitted by *Alternaria alternata* fungi (FIGS. 7A and 7C), a positive effect that is also reflected in an increase in starch accumulation (FIGS. 7B and 7D).

The authors of the invention characterized leaves that had previously been stained with iodine solutions to confirm that what was being measured was really starch. Furthermore, confocal fluorescence microscopy analysis was performed on plants that expressed granule-bound starch synthase (GBSS) of *Arabidopsis* fused with green fluorescent protein (GFP) (Szydlowski et al., 2009: Plant Cell 21, 2443-2457) cultured in the presence and absence of FVs (volatile fungi) emitted by *Alternaria alternata*. As shown in FIGS. 8A and 8B, these analyses showed that iodine staining of leaves of plants cultured in the presence of FVs was much darker than that of control plants. Optical microscopy analyses (FIGS. 8C and 8D) of leaf sections showed that iodine staining was located within cell chloroplasts of the mesophyll. Furthermore, confocal laser scanning microscopy analyses of transgenic leaves that expressed the marker of GBSS-GFP starch granules showed that starch granules were much larger when plants were cultured in the presence of FVs than under control conditions (FIGS. 8E, 8F and 8G). These analyses show that the increase in starch content is not due to an increase in the number of granules per plastid, but to the spectacular increase in size of starch granules.

It was confirmed if the existence of the microbial volatile induced starch accumulation process (MIVOISAP) extended in plants by measuring starch content in leaves of *Arabidopsis*, potato (*Solanum tuberosum* L.), maize (*Zea mays*), tobacco (*Nicotiana tabacum*) and barley (*Hordeum vulgare*) plants cultured in the presence or absence of FVs emitted by *Alternaria alternata*. These experiments were carried out using plants cultured in solid MS medium with or without with 90 mM sucrose supplementation. As shown in FIG. 9, these analyses showed that, regardless of the presence of sucrose in the culture medium, starch content in leaves of the five species was greater in excess when plants were grown in the presence of FVs with respect to the absence of FVs. It is worth highlighting that levels of starch in potato plants cultured in the presence of FVs (approximately 500-600 mol glucose/g of fresh weight) were comparable to those that are known for potato tubers (Baroja-Fernández et al., 2009: Plant Cell Physiol. 50, 1651-1662). Furthermore, as shown in FIG. 10, the presence of FVs stimulates starch accumulation in potato tubers and stems. Therefore, the overall data showed that MIVOISAP occurs ubiquitously between plants and in different organs.

Example 2

FVs Promote Starch Accumulation in Detached Leaves

To investigate if microbial volatiles promoting leaf starch accumulation are perceived in leaves or in other parts of the plant, starch content in detached leaves of, potato, maize, tobacco, *Arabidopsis* and barley plants cultured in solid MS medium (with or without sucrose) in the presence or absence of FVs emitted by the fungal species *A. alternata* was measured.

Regardless of the presence of sucrose in the culture medium, FV-treated leaves accumulated much higher levels of starch than the control plants (FIG. 11), the overall data therefore showing that the FVs promoting starch accumulation are perceived in the leaves. This effect was observed not only when the leaves were cultured in solid MS medium, but also when they were maintained in liquid MS medium or in water (FIG. 12). It should be highlighted that the detached leaves of the five species analyzed accumulated more starch than the leaves attached to the whole plant, which indicates that (a) abiotic stress may, to some extent, promote starch accumulation in leaves, and (b) exerts a positive effect on MIVOISAP.

Example 3

Transcriptome Profile of Potato Leaves Cultured in the Presence of FVs

To better understand the phenomenon of starch accumulation in leaves promoted by microbial volatiles, high-throughput transcriptome analysis of leaves from potato plants cultured in MS medium (with or without sucrose) in the presence and in the absence of FVs emitted by *Alternaria alternata* was performed using the POCI 44K 60-mer oligo array (http://pgrc.ipk-gatersleben.de/poci) (Kloosterman et al. 2008: Funct. Integr. Genomcs 8, 329-340).

When plants were cultured in MS medium supplemented with sucrose, 3,019 genes were found to be deregulated in the presence of FVs (more than 2.5-fold difference relative to control; P value<0.05), 1,203 of them being classified as "no function assigned". Among this population, 1,192 genes were up-regulated and 1,827 genes were down-regulated.

When plants were cultured in MS medium without sucrose, 2,856 genes were found to be deregulated in the presence of FVs, 1,109 of them being classified as "no function assigned". Among this population, 1,671 genes were up-regulated and 1,185 genes were down-regulated. Quantitative real-time transcription-PCR (RT-PCR) analyses of some of the identified genes (FIG. 13) validated the results of the array analyses.

To determine the biological processes affected by microbial volatiles, a gene analysis was carried out using the MapMan tool (Thimm et al. 2004: Plant J. 37, 914-939) (http://gabi.rzpd.de/projects/MapMan/). As shown in the graphs of FIG. 14, this study showed that FVs promoted drastic changes in the expression of genes involved in multiple processes such as metabolism of carbohydrates, amino acids, sulfur and lipids, the redox status of the cell, development, cell wall biosynthesis, photosynthesis, secondary metabolism, protein translation and stability, vesicle trafficking, signaling, energy production and stress responses. FIG. 14 gives a general view of the metabolic processes involved in the changes, both in the presence (Panel A) and in the absence (Panel B) of sucrose.

It should be highlighted that no changes were observed in the expression of a number of protein-encoding genes that are thought to be involved in starch and sucrose metabolism such as β-glucan/water dikinases, plastidial adenylate kinase, plastidial hexokinase, plastidial phosphoglucose isomerase, plastidial phosphoglucomutase, the small catalytic subunit of AGP, ADPG pyrophosphatase, starch synthase (SS) classes I and II, sucrose transporters, UDPglucose (UDPG) pyrophosphorylase, cytosolic phosphoglucose isomerase, cytosolic phosphoglucomutase, sucrose-phosphate synthase and alkaline invertase.

Example 4

Detailed Analysis of Functions Linked to Starch Metabolism

Studies of transcriptome analysis were complemented with studies of variation analysis in the enzymatic activity of different enzymes, performed as described above in the "Enzyme assays" section. The enzymes studied and results obtained (expressed in milliunits per grams of fresh weight) are summarized below in Table 3:

TABLE 3

Enzymatic activity of starch metabolism enzymes

| Enzymatic activity (mU/g FW) | −FV | +FV |
|---|---|---|
| AGP (with DTT) | 126.0 ± 13.2 | 161.3 ± 20.5 |
| SuSy | 27.2 ± 2.9 | 255.0 ± 5.9 |
| Total SS | 2.40 ± 0.52 | 8.11 ± 0.04 |
| β-amylase | 2.00 ± 0.24 | 1.31 ± 0.27 |
| PPase | 2.22 ± 0.12 | 1.67 ± 0.10 |
| Acid invertase | 423.1 ± 17.6 | 160.8 ± 14.7 |
| pG6PDH | 65.5 ± 1.3 | 41.2 ± 2.4 |
| SBE | 0.41 ± 0.14 | 2.61 ± 0.49 |
| Nitrite reductase | 141.4 ± 0.2 | 63.13 ± 13.4 |
| Cytosolic fructose-1,6-bisphosphatase | 10.8 ± 0.2 | 3.3 ± 0.2 |

These data were considered in combination with the data obtained from the transcriptome analysis to study in detail some functions that were affected by FV treatment, which are directly or indirectly linked to starch metabolism. The analysis performed for each of said functions is described in the following sections.

4.1. Changes in AGP Activity are not Determining Factors in MIVOISAP in Potato Plants It is widely assumed that AGP is the major limiting step in starch biosynthesis, and the sole enzyme that catalyzes ADPG production linked to starch production (Neuhaus et al. 2005: Trends Plant Sci. 10, 154-156; Streb et al. 2009: Plant Physiol. 151, 1769-1772). This heterotetrameric enzyme is allosterically activated in leaves by means of 3-phosphoglycerate and is inhibited by means of Pi. It comprises two types of homologous but different subunits, the small subunit (APS) and the large subunit (APL), which is encoded by three different genes (APL1, APL2 and APL3) (Crevillén et al. 2005: J. Biol. Chem. 280, 8143-8140).

The possible influence of AGP (ADP-glucose pyrophosphorylase) activity and of changes in its two subunits on MIVOISAP was therefore studied. Studies on potato plants cultured in the presence of cultures of *Alternaria alternata* were performed similarly to that described in preceding examples.

Transcriptome analyses showed that of the two AGP subunits, the levels of transcripts of the smaller subunit (APS) remained unchanged after FV treatment. In contrast, the expression of one of the genes encoding the larger subunit (APL1) was up-regulated (14.98-fold increase), whereas another one of the genes which also encodes the large subunit, APL3, was down-regulated (8.8-fold reduction) as further confirmed by quantitative RT-PCR analysis (FIG. 13).

Figure 15:
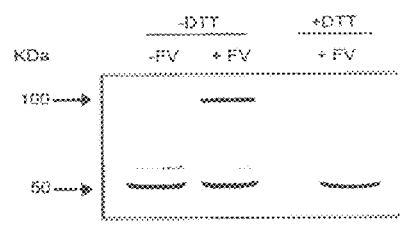
Figure 16:
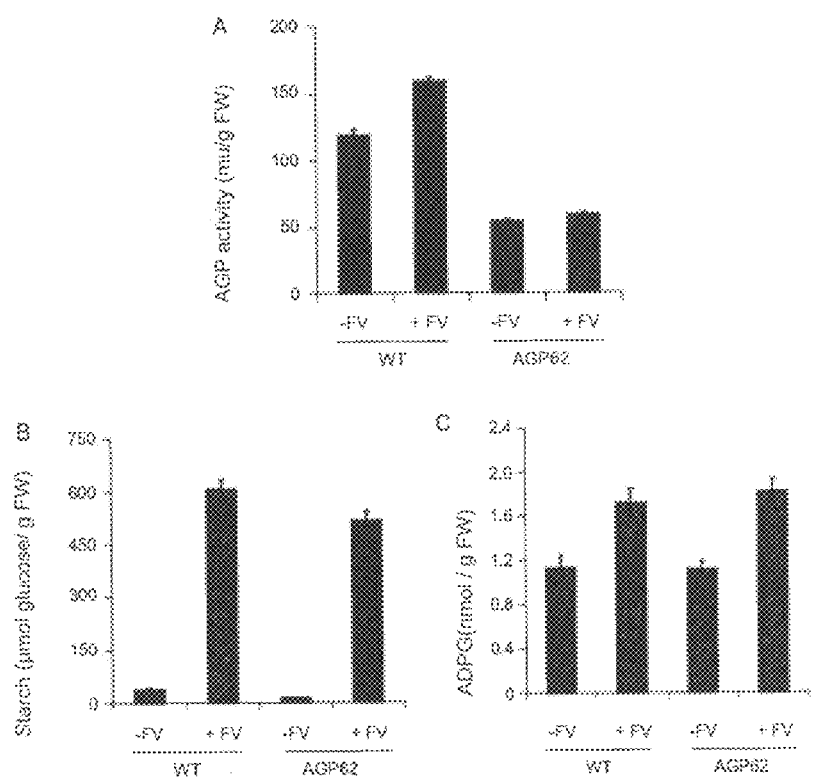

As shown in Table 3 above, total AGP activity was slightly altered by FV treatment (1.5-fold increase and 1.5-fold reduction when AGP activity was measured in the presence or in the absence of 5 mM dithiothreitol (DTT), respectively). Furthermore, Western-type blot analysis did not show any apparent difference in the amount of AGP between FV-treated and non-treated leaves (FIG. 15).

Treatment with FVs resulted in an increase by approximately 35% in the levels of intracellular 3-phosphoglycerate (494.0±36.0 μmol/g FW in the absence of FVs versus 674,1±127.5 μmol/g FW in the presence of FVs), which would indicate that AGP is slightly activated during MIVOISAP.

Because AGP catalyzes the reversible conversion of ATP and glucose-1-P into ADPG and pyrophosphate (PPi), alkaline pyrophosphatase (PPase) is considered to play a pivotal role in starch biosynthesis since it displaces the AGP reaction from equilibrium through rapid removal of PPi. However, quantitative RT-PCR analysis (FIG. 13) and transcriptome analysis showed that treatment with fungal volatiles resulted in down-regulation of PPase (3.72-fold reduction), which was accompanied by a reduction in PPase activity (see Table 3). It is thus conceivable that with FV treatment PPi will accumulate in the chloroplast, thus preventing AGP-mediated ADPG production.

Starch synthesis is regulated by thioredoxin-mediated post-translational redox activation of AGP (Ballicora et al. 2000: J. Biol. Chem. 275, 1315-1320), which is promoted by trehalose-6-phosphate formed in the cytosol (Kolbe et al. 2005: Proc. Natl. Acad. Sci. USA 102, 11118-11123). It should be highlighted that quantitative RT-PCR analyses (FIG. 13) and transcriptome analyses showed that trehalose-6-phosphate synthase and the plastidial thioredoxins were strongly down-regulated when plants were cultured in the presence of FVs (7.57- and 8.31-fold reduction for thioredoxin m and f, respectively, and 4.57-fold reduction of trehalose-6-phosphate synthase in the presence of sucrose; 3.71- and 2.74-fold reduction for thioredoxin m and f, respectively, and 4.89-fold reduction of trehalose-6-phosphate synthase in the absence of sucrose). To examine whether this situation affects AGP redox status, extracts from control and FV-treated potato leaves were separated by reductive and non-reductive SDS-PAGE and subsequently subjected to Western-type blot analysis of AGP. It is important to point out that when leaf extracts were separated on non-reductive gels with SDS, AGP is present as a mixture of 50 kD active monomers and 100 kD inactive dimers formed by intermolecular linkages involving cysteine bridges. These dimers can be reactivated in vitro by incubating extracts with DTT (Hendriks et al. 2003: Plant Physiol. 133, 838-849; Kolbe et al. 2005: Proc. Natl. Acad. Sci. USA 102, 11118-11123). As shown in FIG. 15, FV-treated potato leaves accumulate far greater amounts of 100 kD inactive dimers than control leaves under non-reducing conditions. These 100 kD dimers could be converted into 50 kD monomers when extracts were obtained and separated under non-reducing conditions (including DTT) (FIG. 15), the overall data thus indicating that AGP is largely oxidized (inactive) in FV-treated potato leaves.

To further evaluate the relevance of AGP in MIVOISAP, AGP activity, and ADPG and starch content was measured in leaves of AGP62 potato plants (in which the APS subunit is inactivated by antisense elements (Müller-Röber et al. 1992: EMBO J. 11, 1229-1238)) cultured in the presence and absence of FVs. As illustrated in FIG. 16A, AGP activity in AGP62 leaves was 30% of that of wild-type (WT) leaves. Unlike WT leaves, AGP activity in AGP62 plants did not increase upon FV treatment. It should be pointed out that FV treatment resulted in a dramatic enhancement of starch accumulation (FIG. 16B), and in an approximately 70% increase in ADPG content (FIG. 16C) in AGP62 leaves. Starch and ADPG contents in FV-treated AGP62 leaves were comparable with those observed in FV-treated WT leaves.

The overall data would thus indicate that changes in AGP activity play a minor role, if any, in MIVOISAP in potato leaves.

4.2. Fungal Volatiles Strongly Up-Regulate SuSy and Down-Regulate Expression of Acid Invertase As discussed in the "Background of the Invention" section, it has generally been considered that starch biosynthesis in leaves takes place exclusively in the chloroplast, and is segregated from the sucrose biosynthetic process taking place in the cytosol, whereas recent evidence indicates the existence of an additional pathway or additional pathways in which ADPG linked to starch biosynthesis is produced de novo in the cytosol by means of SuSy.

In connection with these theories, it should be highlighted that the transcriptome analyses of leaves of plants cultured in the presence or in the absence of FVs showed that FV treatment resulted in a drastic enhancement of expression of Sus4 (29.4- and 31.62-fold increase when plants were cultured in the presence or in the absence of sucrose, respectively), a SuSy isoform that controls ADPG, UDPG and starch accumulation in both potato source leaves and tubers (Muñoz et al. 2005: Plant Cell Physiol. 46, 1366-1376; Baroja-Fernandez et al. 2009: Plant Cell Physiol. 50, 1651-1662). In fact, analyses of the intracellular levels of starch and nucleotide-sugars in leaves of potato plants cultured in the presence and absence of FVs showed a positive correlation between the patterns of SuSy activity and starch, UDPG and ADPG contents (FIG. 17). This drastic enhancement of the expression of SuSy by FV treatment was additionally confirmed by Western-type blot analysis (FIG. 18), quantitative RT-PCR analysis (FIG. 13), and by measurement analysis of enzymatic activity (10-fold increase: see Table 3).

Acid invertase is a sucrolytic enzyme the activity of which is post-translationally regulated by a proteinaceous inhibitor (Bracho and Whitaker 1990: Plant Physiol. 92, 386-394) in tubers. These two sucrolytic enzymes compete for the same sucrose supply, acting as one of the main determining factors of starch accumulation the balance between SuSy and acid invertase (Baroja-Fernández et al. 2009: Plant Cell Physiol. 50, 1651-1662). It should be highlighted that RNA profile analyses showed that FV treatment resulted in a down-regulation of expression of acid invertase (2.61- and 2.04-fold reduction in the presence and absence of sucrose, respectively), and a dramatic enhancement of transcripts encoding the inhibitor of this sucrolytic enzyme (17.78- and 18.1-fold increase in the presence and absence of sucrose, respectively), which was additionally confirmed by quantitative RT-PCR (FIG. 13) and enzymatic activity analysis (see Table 3).

The overall data indicate that (a) SuSy and acid invertase-mediated sucrolytic pathways are coordinately regulated in response to identical signals, and (b) the balance between these pathways is a major determining factor of starch accumulation in potato leaves exposed to microbial volatiles. Because of the positive correlation existing between the patterns of SuSy activity and of starch, ADPG and UDPG contents in leaves of FV-treated and non-treated plants (FIG. 17), the overall data also indicated that high ADPG, UDPG and starch levels occurring in FV-treated potato leaves are ascribed, at least in part, to enhanced SuSy activity during MIVOISAP in potato.

4.3. Fungal Volatiles Down-Regulate the Main Pathways of Internal Amino Acid Provision As mentioned above in the "Background of the Invention" section, recent studies have demonstrated that plants have a ppGpp-mediated regulating system similar to that in bacteria, which has been demonstrated to play a crucial role in aspects such as plant fertilization. ppGpp accumulates in the chloroplast of stressed leaves through regulation of the expression of RelA/SpoT homologs (RSH).

It should be highlighted that the quantitative RT-PCR analyses (FIG. 13) and transcriptome analyses described above in the examples of the present application showed that, regardless of the presence of sucrose, FV treatment resulted in a down-regulation of RSH (2.6- and 2.42-fold reduction in the presence and absence of sucrose, respectively).

It is possible that plants develop responses similar to those existing in bacteria regulating glycogen biosynthesis as a consequence of amino acid deprivation and/or provision. Consistent with this assumption, the quantitative RT-PCR analyses (FIG. 13) and transcriptome analyses showed that FV treatment results in a drastic reduction of the expression of GAPDH and pPGK (32.68- and 5.32-fold reduction, respectively). These analysis further showed that FV treatment resulted in a marked down-regulation of plastidial G6P dehydrogenase (pG6PDH) (6.17-fold reduction) (also see FIG. 13 and Table 3), an enzyme of the oxidative pentose phosphate pathway (OPPP) which is involved in the production of reducing power required for amino acid biosynthesis in heterotrophic organs or in leaves during the night-time period.

FV treatment further resulted in a marked reduction of the expression of genes encoding a set of plastidial proteins involved in nitrogen assimilation such as those encoding the nitrite transporter, nitrite reductase, glutamate synthase and glutamate/malate translocator (3.88-, 9.85-, 3.86- and 3.22-fold reduction, respectively) (also see FIG. 13 and Table 3).

The first step in the conversion of sulfate into the sulfur amino acids cysteine and methionine is catalyzed by ATP sulfurylase. This plastidial enzyme catalyzes the reversible conversion of ATP and sulfate into adenosine-5'-phosphosulfate and PPi, which is displaced from equilibrium by PPase through rapid removal of PPi. As discussed above, FV treatment results in PPase down-regulation. It is thus conceivable that with FV treatment PPi will accumulate in the chloroplast, thus preventing sulfur amino acid biosynthesis by inhibiting ATP sulfurylase. It is noteworthy that FV treatment resulted in down-regulation of plastidial serine acetyltransferase, cysteine synthase and cystathionine-gamma-synthase (3.43-, 2.85- and 2.53-fold reduction, respectively), all enzymes necessary for cysteine and methionine synthesis in the chloroplast.

Therefore, it was investigated whether plastidial cysteine provision impairments are directly involved in MIVOISAP by measuring the starch content in detached potato leaves cultured in the presence and in the absence of FVs emitted by *Alternaria alternata*, and in the presence of different concentrations of cysteine. Most importantly, these analyses showed that unlike other amino acids, MIVOISAP was strongly suppressed by exogenously added cysteine (FIG. 19). Other amino acids, in contrast, did not inhibit MIVOISAP.

Therefore, the overall data strongly indicated that MIVOISAP is the consequence of a response triggered by inadequate internal cysteine provision. Since sulfur amino acids are the main metabolic entrance of reduced sulfur in cell metabolism, the authors of the invention considered the hypothesis that the high starch content of FV-treated leaves is the result, at least in part, of a response triggered by the deprivation of both nitrogen and sulfur.

Proteases play a major role in protein quality control, being responsible for the degradation of damaged and aberrant polypeptides as well as for the recycling of amino acids for de novo protein biosynthesis. Proteolysis also provides the amino acids necessary for maintaining cellular homeostasis, this being a process that involves a major portion of the cell's maintenance energy requirement. In that line, it should be highlighted that the analyses of transcripts of the present invention showed that FV treatment drastically enhanced the expression of many protease inhibitors. It is therefore highly conceivable that (a) the resulting lack of proteolytic activity would result in impairment of the internal amino acid supply, which triggers a response that leads to starch overaccumulation, and (b) decreased demand for ATP for protein breakdown would result in the availability of excess energy for starch biosynthesis.

4.4. Fungal Volatiles Up-Regulate Starch Synthases Class III and IV

Five different classes of starch synthases (SS) in plants are known: GBSS, which is responsible for amylose synthesis, and SS class I, II, III, and IV (SSI, SSII, SSIII, and SSIV, respectively). Abel et al. (Abel et al., 1996: Plant J. 10, 981-991) have demonstrated that the reduction of SSIII leads to the synthesis of structurally modified starch in transgenic potato plants. In addition, Roldan et al. (Roldan et al. 2007: Plant J. 49, 492-504) have demonstrated that elimination of SSIV determines that the chloroplasts will accumulate only one large starch granule in *Arabidopsis*. Furthermore, using different combinations of SS mutations in the SSIV background, Szydlowski et al. (Szydlowski et al 2009: Plant Cell 21, 2443-2457) have recently demonstrated that double *Arabidopsis* mutants lacking SSIII and SSIV functions show a phenotype lacking starch.

The overall data (a) indicated that both the SSIII and SSIV play a key role in starch accumulation, although SSIV is mandatory to produce the regular number of starch granules found in wild-type plants, and (b) suggested that SSIV plays an important role in the starch granule initiation process.

Consistent with the idea that SSIII and SSIV are major determining factors of starch accumulation in potato leaves, transcriptome analyses showed that, regardless of the presence of sucrose in the culture medium, FV treatment resulted in a large increase in expression of SSIV (7.00 and 4.68-fold increase in the presence and in the absence of sucrose, respectively) and a moderate increase in expression of SSIII (2.53-fold increase in the presence of sucrose), which results were confirmed by quantitative RT-PCR analysis (FIG. 13). No changes were observed in the expression levels of SS class I and II. Enzymatic activity analyses showed that FV treatment resulted in a 3-fold increase in the total SS activity (see Table 3). The overall data therefore indicate that MIVOISAP can be ascribed, at least in part, to the enhancement of SSIII and SSIV activity.

4.5. Fungal Volatiles Promote Both Amylose Content Reduction and Structural Changes in Amylopectin Increasing the Balance Between Starch Branching and Debranching Activities The starch granule is composed of two structurally different homopolymers: amylose, which is essentially linear, and amylopectin, which is a moderately branched macromolecule. The starch in potato leaves contains 10-15% amylose. Whereas amylose is produced by GBSS, amylopectin is synthesized by the combined actions of soluble SS and starch branching enzyme (SBE), the latter catalyzing the formation of the α-1,6 linkages within the starch molecule. According to the "trimming model" of starch granule formation, amylopectin biosynthesis is also the result of "trimming" by debranching enzymes (isoamylases and pullulanases that hydrolyze α-1,6 linkages within the starch molecule) of highly branched glucans that are synthesized by soluble SS and SBE.

In this line, it should be highlighted that quantitative RT-PCR analyses (FIG. 13) and transcriptome analyses showed that FV treatment resulted in a drastic increase in expression of SBE (32.66- and 2.5-fold increase in the presence and in the absence of sucrose, respectively) and a moderate increase in expression of both pullulanase and GBSS when plants were cultured in heterotrophic conditions (3.4- and 2.98-fold increase, respectively). Consistently, SBE activity in FV-treated leaves was markedly higher than in non-treated leaves (Table 3). It should be highlighted that changes in the expression of these genes were accompanied by an important reduction in relative amylose content (FIG. 20A).

To investigate whether the FV-promoted changes in SS and SBE activities resulted in structural changes in amylopectin, purified amylopectin from FV-treated and non-treated leaves was subjected to enzymatic debranching, and the chain length distribution was determined by high-performance anion exchange chromatography with pulsed amperometric detection (HPAEC-PAD). These analyses showed that FV treatment exerts an important effect on the structure of amylopectin, since amylopectin of FV-treated leaves contained more chains with a degree of polymerization (DP) less than 20 monomers than amylopectin of non-treated leaves (FIG. 20B, FIG. 20C). The overall data therefore indicated that structural changes occurring in the starch molecules of FV-treated plants can be ascribed, at least in part, to enhancement of SS and SBE activities.

4.6. Fungal Volatiles Strongly Down-Regulate Starch Degradation Enzymes

Using the antisense technique, Scheidig et al. (Scheidig et al., 2002: Plant J. 30, 581-591) demonstrated that a chloroplast-targeted β-amylase BMY1 that controls starch degradation in potato leaves. Consistent with this, the transcriptome analyses described in the present application showed that FV treatment resulted in a drastic down-regulation of PCT-BMY1 (5.89- and 3.66-fold reduction in the presence and in the absence of sucrose, respectively, which was further confirmed by quantitative RT-PCR (FIG. 13) and by enzymatic activity analysis (Table 3).

Higher plants contain both cytosolic and plastidial starch phosphorylases. Unlike in plastidial β-amylases involved in starch degradation, the precise in vivo function of the plastidial isoform is not yet known, although it has generally been accepted that it may be involved in starch degradation. Zeeman et al. (Zeeman et al. 2004: Plant Physiol. 135, 849-858) argued that this enzyme is involved in the abiotic stress tolerance in *Arabidopsis*, providing substrates from starch into the OPPP to alleviate the stress. It should be highlighted that RT-PCR analyses (FIG. 13) and transcriptome analyses showed that FV treatment resulted in a marked down-regulation of the expression of plastidial starch phosphorylase when plants were cultured in heterotrophic conditions (5.14-fold reduction).

The overall data therefore indicated that MIVOISAP can be ascribed, at least in part, to the down-regulation of plastidial β-amylase isoforms and starch phosphorylase.

4.7. Fungal Volatiles Up-Regulate Genes Involved in Endocytosis and the Vesicle Trafficking Synthesized from phosphatidylinositol (PI) by PI-3-phosphate (PI3P) kinase (PI3K) and by PI-4-phosphate (PI4P) kinase (PI4K), PI3P and PI4P have been involved in various physiological functions, including plasma membrane endocytosis, vesicle trafficking, and vacuoles biogenesis and organization. Endocytosis is a process involved in the internalization of molecules from the plasma membrane and extracellular environment, and plasma membrane recycling. The increase in phosphoinositide metabolism results in an increase in the use of sugars from the medium (Im et al. 2007), which is a strong indication that phosphoinositide-mediated signaling plays an important role in the enhancement of extracellular sugar absorption, internalization and storage in vacuoles. It should be highlighted that recent studies have provided strong evidence that an important part of the sucrose incorporated into heterotrophic cells is absorbed by means of processes of PI3K and/or PI4K-mediated endocytosis and vesicle trafficking before being converted into starch (Baroja-Fernandez et al. 2006: Plant Cell Physiol. 47, 447-456). Consistent with these observations, RT-PCR analyses (FIG. 13) and transcriptome analyses showed that the genes encoding PI4K and PI3K are up-regulated by FV treatment (3.55- and 3.12-fold increase, respectively). PI is synthesized in the cytosol from G6P in a 3-step process involving inositol-phosphate synthase, inositol monophosphatase and PI synthase. It should be highlighted that the RT-PCR analyses (FIG. 13) and transcriptome analyses showed that the genes encoding inositol-phosphate synthase and inositol monophosphatase are up-regulated by FV treatment (3.78- and 4.62-fold increase, respectively).

Plant actin cytoskeleton is a dynamic support structure which plays a pivotal role in organule movement, vesicle trafficking, cytoplasmic flows, plant defenses against pathogens, etc., in response to internal and external signals. Evidence that the actin cytoskeleton is also involved in endocytic absorption and trafficking of sucrose linked to starch biosynthesis in sycamore cells in culture has recently been provided (Baroja-Fernandez et al. 2006: Plant Cell Physiol. 47, 447-456). It should be highlighted that it has been demonstrated that SuSy, a key enzyme in the starch biosynthesis process (see above), is associated with the actin cytoskeleton (Dunkan and Huber 2007: Plant Cell Physiol. 48, 1612-1623), which is further support to the view that the actin cytoskeleton determines, to a certain extent, starch metabolism. Actin depolymerizing factors are dynamic organization modulators of the actin cytoskeleton which modulate the exchange rate of filaments and the interconnection of cell signals with cytoskeleton-dependent processes. Consistent with the view that cytoskeleton-mediated endocytosis and/or vesicle trafficking can play an important role in MIVOISAP, the RT-PCR analyses (FIG. 13) and transcriptome analyses showed that the expression of actin depolymerizing factor is up-regulated by FV treatment (increase in 3.26-fold)

The overall data therefore show that, as schematically illustrated in FIG. 21, endocytic sucrose absorption and vesicle trafficking may be involved in MIVOISAP, particularly when plants are cultured in the presence of sucrose.

4.8. Fungal Volatiles Promote Down-Regulation of Photosynthesis Genes when Plants are Cultured in Heterotrophic Conditions One of the most striking alterations in the transcriptome of FV-treated plants cultured in the presence of sucrose involves the repression of genes encoding proteins that function in light reactions of photosynthesis. Furthermore, when plants are cultured in the presence of sucrose, genes encoding key enzymes of the Calvin cycle and photorespiration are also strongly suppressed by FV treatment. These include pPGK, pGAPDH, triose-P-isomerase, transketolase, pentose-P-epimerase, ribose-P-isomerase, fructose-bisphosphate aldolase, fructose-1,6-bisphosphatase, sedoheptulose-1,7-bisphosphatase, Rubisco, glycolate oxidase, catalase, serine hydroxymethyltransferase, and hydroxypyruvate reductase (5.32-, 32.68-, 3.69-, 3.65-, 4.79-, 6.43-, 14.97-, 17.99-, 11.09-, 46.62-, 9.24-, 4.01-, 6.6- and 7.79-fold reduction, respectively) (also see FIG. 13). Furthermore, FV treatment of plants cultured with sucrose resulted in the repression of the gene encoding photochlorophyllide oxide reductase (reduction of 7.73), which is necessary for chlorophyll biosynthesis. In these conditions, it is highly conceivable that, as schematically illustrated in FIG. 21, much of the starch accumulated by plants cultured in heterotrophic conditions will be produced from the metabolic degradation of sucrose taken up from the culture medium (see below).

4.9. FVs Strongly Promote Aerobic and Anaerobic Metabolism when Plants are Cultured in Heterotrophic Conditions Simultaneous to the repression of genes encoding proteins which function in light reactions of photosynthesis (see above), FV treatment resulted in the down-regulation of plastidial ATP synthase when plants were cultured in heterotrophic conditions (9.09-fold reduction). In these conditions, FVs promoted the transcription of genes encoding glycolytic enzymes such as enolase, pyruvate kinase, phosphoenol pyruvate (PEP) carboxykinase and PEP carboxylase (4.94-, 5.48-, 19.64- and 6.03-fold increase, respectively). This effect was much less pronounced when plants were cultured in autotrophic conditions. Because PEP carboxykinase and PEP carboxylase are involved in the conversion of PEP into oxalacetate, the overall data indicate that FVs promote glycolysis and the flow of carbon towards the tricarboxylic acid (TCA) cycle, as shown in FIG. 21, particularly when plants are cultured in heterotrophic conditions. In this respect, it should be highlighted that FV treatment resulted in an increase in the expression of genes encoding enzymes of the TCA cycle such as succinate dehydrogenase and isocitrate dehydrogenase (2.8- and 2.57-fold increase, respectively). Some genes involved in fermentation, including those which encode alcohol dehydrogenase (ADH), pyruvate decarboxylase and an aldehyde dehydrogenase, were strongly up-regulated by FV treatment, both in heterotrophic conditions (51.43- and 9.92-fold increase for ADH and aldehyde dehydrogenase, respectively), and autotrophic conditions (9.92- and 3.77-fold increase for ADH and pyruvate decarboxylase, respectively) (also see Table 3). The increase in activity of the fermentation pathway of ethanol from pyruvate allows reoxidation of NADH produced in glucolysis, therefore allowing the plant to generate ATP regardless of oxidative phosphorylation. Therefore, promotion by FVs of enhancement of the expression of genes encoding enzymes involved in glucolysis, the TCA cycle and fermentation is consistent with the notion that both the aerobic and anaerobic metabolisms are up-regulated during MIVOISAP to generate energy in reduced photosynthetic ATP production conditions.

Higher plants have ATP/ADP transporters in both heterotrophic and autotrophic plastids in order to take up cytosolic ATP, exchanging it with plastidial ADP. Because heterotrophic plastids lack ATP-producing machinery by photosynthesis, the ATP/ADP transporter is necessary to supply energy to anabolic processes located in the stroma such as those involved in amino acid, starch and fatty acid production. In chloroplasts, it has been demonstrated that ATP/ADP transporters are important for nocturnal importation of ATP and to prevent damage caused by photooxidation (Reinhold et al. 2007: Plant J. 50, 293-304). It should be highlighted that FVs up-regulate the expression of plastidial ATP/ADP transporter when plants are cultured in heterotrophic conditions (3.16-fold increase), which is consistent with the notion that extraplastidial ATP for the most part supports anabolic pathways occurring in the chloroplast of FV-treated plants cultured in heterotrophic growth conditions.

4.10. Fungal Volatiles Promote the Exchange of Glucose-6-Phosphate and Repress the Exchange of Triose-Phosphate Between the Chloroplast and Cytosol The major chloroplast envelope membrane protein, the triose-P/3-phosphoglycerate/P translocator (TPT), is fundamental for the communication between chloroplast and cytosol, since it exports the primary products of the Calvin cycle (i.e., triose phosphates and 3-phosphoglycerate) out of the chloroplast in a strict counter-exchange for Pi. Potato plants with TPT inhibited by antisense molecules accumulate in their leaves 2-3 times more starch and more 3-phosphoglycerate than wild-type leaves, and have reduced plant vigor. It should be highlighted that the RT-PCR analyses (FIG. 13) and transcriptome analyses showed that, regardless of the presence of sucrose in the culture medium, FV treatment resulted in reduced expression of TPT (3.17- and 2.25-fold reduction in the presence and in the absence of sucrose, respectively). Leaves of FV-treated plants accumulated moderately high levels of 3-phosphoglycerate (see above), which can probably be ascribed to reduction of TPT-mediated transport of 3-phosphoglycerate from chloroplast to cytosol.

Non-green plastids of heterotrophic tissues depend on the provision of G6P from the cytosol through the G6P/Pi antiporter system. The imported G6P can be used for starch and fatty acid synthesis. G6P can also be used to activate the OPPP which, as discussed above, is the main source of reducing power required for the reduction of nitrite and for fatty acid and amino acid biosynthesis. It should be highlighted that although the expression of G6P/Pi translocator is mainly restricted to heterotrophic tissues, FV treatment strongly enhanced the expression of G6P/Pi translocator in leaves when plants were cultured in the presence and in the absence of sucrose, as confirmed by both RT-PCR analyses (FIG. 13) and transcriptome analyses (30.23- and 22.08-fold increase when plants were cultured in the presence and in the absence of sucrose, respectively).

The involvement of the G6P/Pi translocator in the importation of cytosolic G6P to the chloroplast when plants were treated with FVs is questionable because, as shown above, the enzymes involved in plastidial G6P metabolism are drastically down-regulated. This and the reduction of the expression of proteins involved in G6P synthesis in the cytosol from products of the Calvin cycle such as TPT (see above), cytosolic fructose-1,6-bisphosphatase (see Table 3 and FIG. 13) (9.87- and 3.61-fold reduction in the presence and in the absence of sucrose, respectively), and fructose-6-phosphate 2 kinase/fructose-2,6-bisphosphatase (3.39- and 2.2-fold reduction in the presence and in the absence of sucrose, respectively) (also see FIG. 13) suggest that, as shown in FIG. 21, under FV treatment conditions the G6P/Pi transporter would play a major role in exporting G6P molecules from the chloroplast to the cytosol to later be channeled towards the TCA cycle and/or fermentation pathways, and/or be converted into compounds such as sucrose and PI which is necessary for endocytosis and vesicle trafficking processes.

4.11. Influence of FVs on Other Genes of Interest

All the microbial species analyzed in this work emitted volatiles that promoted plant growth, which would indicated that the machinery involved in the biosynthesis is up-regulated during MIVOISAP. Consistent with this assumption, the analysis of transcripts of leaves of potato plants showed that FV treatment resulted in the up-regulation of cellulose synthase and the callose synthase (9.78- and 2.1-fold increase, respectively).

MIVOISAP involves changes in the expression of a number of genes encoding enzymes fundamental in the carbohydrate metabolism and in energy production/consumption, which suggests that MIVOISAP is a highly coordinated and regulated process. It should be highlighted that the analyses of transcripts described in the present application showed that FV treatment strongly promoted the expression of SNF4 (6.64-fold increase) (also see FIG. 13), an activator of the protein kinase SnRK1, which is a global regulator of carbon metabolism in plants. It is therefore likely that (a) SNF4 exerts a positive effect on starch accumulation through of SnRK1 activation, and (b) SnRK1 plays a regulating role during MIVOISAP.

Example 5

Kinetics of Starch Accumulation

To investigate (a) how starch accumulation occurred over time from the time of exposure to microbial volatiles, (b) the possible involvement of regulation mechanisms at the transcriptional and post-transcriptional level of the process and (c) the influence that light may have on accumulation, se kinetic assays on starch accumulation were performed in two different plants: *Arabidopsis thaliana* (cv. Columbia) and potato (*Solanum tuberosum* L. cv Desiree).

Plants were cultured in Petri dishes containing solid MS medium with 90 mM sucrose. Plants were grown in growth chambers with a photoperiod of 16 h of light (300 mol photons $s^{-1}$ $m^{-2}$), 8 hours of darkness and at a constant temperature of 24° C. After approximately 2 weeks of growth after the time of germination, the plants were placed in 500 cubic centimeter plastic boxes in which cultures of *Alternaria alternata* in Petri dishes containing solid MS medium supplemented with 90 mM sucrose had previously been introduced. At the times indicated in FIGS. 22, 23 and 24, the leaves were harvested for subsequent analyses of starch, 3PGA, Pi and SuSy activity content.

5.1. Kinetics of *Arabidopsis thaliana*

*Arabidopsis thaliana* plants were incubated as discussed in the introduction, with 16 hours of light and 8 hours of darkness (except in one of the assays in which the passage of light was prevented by wrapping the plastic box with aluminum foil), using several conditions of the presence or absence of culture of *Alternaria alternata* and, therefore, of the presence or absence of microbial volatiles, resulting in the graphs shown in FIG. 22. The conditions were as follows:

Culture in the presence of fungal volatiles during the entire day (16 hours of light and 8 hours of darkness) (curve with black circles in the graph)

Culture in the presence of fungal volatiles for 16 hours of light; absence of fungal volatiles for 8 hours of darkness (curve with non-shaded circles in the graph)

Culture without volatiles, even during the light period (curve with shaded squares in the graph)

Culture with volatiles in the absence of light for the first 16 hours of culture. Although the culture took place during the 16 hour period of light, the plastic box was wrapped in aluminum foil, therefore preventing contact with light. The results obtained when evaluating accumulated starch (FIG. 22A) show that in the absence of light, even in the presence of volatiles and sucrose in the culture medium of the plant, there is no starch synthesis. In the presence of light without microbial volatiles, starch accumulation rate is approximately 8 nanomoles of glucose transferred to the starch per gram of fresh weight and minute. In the presence of light and microbial volatiles, for the 2 first hours of culture the starch accumulation rate is approximately 100 nanomoles of glucose transferred to the starch per gram of fresh weight and minute. After 2 hours of incubation of the leaves in the presence of microbial volatiles, the starch accumulation rate is approximately 500 nanomoles of glucose transferred to the starch per gram of fresh weight and minute. After the 16 hours of light, the absence of light reduces accumulated starch.

The results demonstrate the connection existing between metabolic processes involved in MIVOISAP and light.

Additionally, by using plants cultured in the same conditions, the 3PGA/Pi balance was compared as described in Muñoz et al., 2005: Plant Cell Physiol. 46: 1366-1376. 3-PGA (3-phosphoglyceric acid) is an allosteric activator of ADPglucose pyrophosphorylase (AGP), whereas orthophosphate (Pi) is a negative regulator of this enzyme, involved in plastidial ADPglucose production. AGP is involved in the production of ADPG linked to starch biosynthesis. It is considered that the allosteric modulation of AGP represents an important determining factor of the starch biosynthesis rate in photosynthetic tissues, although some studies have been unable to find a correlation between 3-PGA levels in the stroma and starch content.

The results are shown in FIG. 22B, where it can be seen that the 3PGA/Pi ratio increases in the case of plants cultured in the presence of light with fungal volatiles; the curve further seems to indicate a ratio between the increase in starch and the increase over time of the obtained value of this ratio. In contrast, in the absence of volatiles and presence of light, or in the presence of volatiles and absence of light, the values obtained over time are similar for the two types of culture conditions, with minor fluctuations over time. The results shown in FIG. 22B seem to indicate that MIVOISAP is due, at least in part, to mechanisms of post-transcriptional regulation such as the allosteric activation of ADPglucose pyrophosphorylase.

5.2. Kinetics of the Concentration of 3-PGA and Pi in MIVOISAP

To corroborate the data of the preceding section, an assay similar to that in section 5.1. was performed: *Arabidopsis thaliana* plants were incubated as described in the "Plants, microbial cultures, growth conditions and sampling" section, with 16 hours of light and 8 hours of darkness, in the presence or in the absence of a culture of *Alternaria alternata* and, therefore, presence or absence of microbial volatiles.

In this new assay, in which the levels of 3-PGA and Pi were determined as described by Lytovchenko et al. (2002), the previously obtained results were confirmed. As can be seen in FIG. 23, the analysis of the kinetics of 3-PGA and Pi accumulation in leaves of *Arabidopsis thaliana* treated and not treated with microbial volatiles confirmed the previous results, showing that the 3-PGA/Pi ratio increased after 6 hours of treatment with fungal volatiles produced by *Alternaria alternata* (see Panel C of FIG. 23; this increase is mainly due to 3-PGA accumulation (Panel A of FIG. 23), more than to the variations in Pi content (Panel B of FIG. 23).

These data confirm that MIVOISAP involves an allosteric activation of AGP due to the increase in 3-PGA.

5.3. Kinetics in Potato Plants

The experiment of section 5.1. was repeated, using in this case potato plants. In this case, starch accumulation during 16 hours of light was measured and, additionally, the activity of the enzyme sucrose synthase (Susy) was also checked.

The results are shown in FIG. 24, where only the data corresponding to plants incubated in the presence of light and of fungal volatiles are shown. Panel A corresponds to starch accumulation and Panel B to SuSy activity.

The data obtained demonstrate that there are transcriptional mechanisms (increase in the expression of SuSy) regulating MIVOISAP.

5.4. Kinetics of Starch Accumulation in the Presence or Absence of Transcriptional and Translational Inhibitors The experiment of section 5.1 was repeated, using in this case leaves cut from *Arabidopsis* incubated in Petri dishes with solid MS medium supplemented with 90 mM sucrose and, where appropriate, with 50 micromoles (μM) of translation inhibitor cycloheximide (Sigma) and 200 micromoles (μM) of transcription inhibitor cordycepin (Sigma) (Fritz, C. C. et al., 1991: Proc. Natl. Acad. Sci. USA 88: 4458-4462; Hayashi, T. and Takagi, S., 2003; Plant Cell Physiol. 44: 1027-1036; Dhonukshe et al., 2006: Developmental Cell 10: 137-150). The dishes were deposited in 500 cubic centimeter boxes in which cultures of *Alternaria alternata* had previously been deposited. The results shown in FIG. 25 according to which both substances strongly inhibit starch accumulation after 2 hours of incubation in the presence of fungal volatiles emitted by *Alternaria alternata*, further suggest that MIVOISAP is regulated, at least in part, transcriptionally.

Example 6

Identification of Volatile Compounds Involved in the Increase in the Starch Accumulation 6.1. Identification of the Substances with the Capacity to Increase Starch Accumulation In order to clarify if the mixtures of volatiles produced by microorganisms contained specific compounds responsible for the growth increase and compounds responsible for the increase in starch accumulation, or if there were compounds capable of producing both effects, assays were performed on cultures of *Arabidopsis thaliana* plants (cv. Columbia) similar to those described in the general section of "Plants, microbial cultures, growth conditions and sampling", although by substituting microbial cultures with solutions of the volatiles to be assayed. To that end, the plants were cultured in Petri dishes containing solid MS medium with 90 mM sucrose. The plants germinated and were grown for two weeks in growth chambers with a photoperiod of 16 h of light (300 µmol of photons $s^{-1}$ $m^{-2}$) and at a constant temperature of 24° C.

The Petri dishes containing completely developed plants were placed in 500 cubic centimeter grow boxes with the particularity that, instead of microbial cultures, Petri dishes containing 2 cubic centimeters of 5% aqueous solutions of one of the following compounds were introduced in said boxes in each case: indol, DTT (dithiothreitol), NAA (1-naphthaleneacetic acid), β-mercaptoethanol, salicylic acid, jasmonic acid, cysteine, acetoin, ethanol, methanol, β-hydroxybutyrate, butanediol, propanoic acid, acetic acid, acetaldehyde, formic acid or butyric acid, without there being any physical contact between the plant and the solution. The ethylene was provided in the form of ethephon powders. The boxes were sealed and leaves were harvested after two days of incubation to analyze starch content. Leaves were harvested at the end of the light period. As a negative control, the Petri dishes containing completely developed plants were cultured for two days in sealed plastic boxes together with a Petri dish containing 2 cubic centimeters of water in the absence of any of the volatile compounds assayed.

Starch was measured using an amyloglucosidase-based test kit (Boehringer Mannheim, Germany).

The results obtained are shown in FIG. 26A.

As illustrated in that figure, neither acetoin nor butanediol, compounds previously involved in growth increase in plants, are involved in MIVOISAP (microbial volatile induced starch accumulation process). As discussed above, both volatile substances are emitted by some isolates of the *Bacillus* genus and both are involved in the promotion of the plant growth exerted by these microorganisms. This demonstrates that MIVOISAP has nothing to do with the promotion of growth by neutral products, such as acetoin and butanediol, which are produced by some microorganisms from pyruvic acid as an alternative to the metabolic pathways of this compound, but is determined by acid substances also produced from metabolizing pyruvic acid following different metabolic pathways, such as acetate, formic acid, etc.

Of all the volatile substances analyzed, only propanoic acid, acetic acid, acetaldehyde, formic acid and butyric acid promote starch overaccumulation. Furthermore, 0.2% solutions of formic acid promote growth and flowering of the plant (FIG. 27), which strongly indicates that the effect of MIVOISAP disclosed in the main patent P201000499 (consisting of the increase in starch accumulation, growth increase and modifications in the growth pattern, including flower induction) is due to the release of small amounts of these acid substances by microorganisms.

6.2. Effect of the Concentration of the Volatile in the Starch Accumulation

To demonstrate if this effect was compound dose-dependent, the assay of the previous section was repeated, the plants growing in the presence of aqueous solutions of 2 cubic centimeters of propanoic acid, acetic acid, acetaldehyde or butyric acid, assaying three different concentrations for each of them, each in different boxes: at 1%, 2% or 5% (v/v).

The results obtained are shown in FIG. 26B. The assay corroborates the positive effect of these compounds on starch accumulation, and further demonstrates that the effect is dose-dependent with respect to the volatile compound present.

Example 7

Influence of the Impairments in Pyruvic Acid Synthesis on Starch Accumulation Produced by Mixtures of Volatiles Emitted by Microorganisms As explained above in the present application, the increase in starch accumulation is observed when plants are cultured in the presence of different microorganisms capable of producing volatiles: bacteria, yeasts and molds. Among them, the culture of *Arabidopsis thaliana* plants in the presence of a culture of the *Escherichia coli* BW25113 bacteria likewise showed the effect of the increase in starch accumulation when said bacterium was cultured in Petri dishes containing solid M9 minimal medium (95 mM $Na_2HPO_4$/44 mM $KH_2PO_4$/17 mM NaCl/37 mM $NH_4Cl$/0.1 mM $CaCl_2$/2 mM $MgSO_4$, 1.5% bacteriological agar) supplemented with 50 mM glucose.

To corroborate the results obtained in Example 6 of the present application, the assay for measuring starch accumulation by mixtures of volatiles produced by microorganisms was repeated using a mutant strain of *Escherichia coli*, *E. coli* ΔpykF (Baba, T., Ara, T., Hasegawa, M., Takai, Y., Okumura, Y., Baba, M, Datsenko, K. A., Tomita, M., Wanner, B. L. and Mori, H. (2006) Construction of *Escherichia coli* K-12 in frame, single-gene knockout mutants: the Keio collection. Mol. Syst. Biol. doi; 10.1038/msb4100050), which is mutant in the pykF gene encoding pyruvate kinase and which, as a result, produces lower amounts of pyruvate and, accordingly, also a lower amount of substances such as formic acid, acetic acid, propanoic acid, lactic acid and acetaldehyde than wild strains of *E. coli*.

Therefore, the test of Example 6 above was repeated, although in this case the plants were placed in sterile 500 cubic centimeter plastic boxes containing microbial cultures of *Escherichia coli* BW25113 (wild strain control) or of *Escherichia coli* ΔpykF.

The results obtained are shown in FIG. 28. It is demonstrated in this figure that this mutant, with impairments in the synthesis of pyruvic acid and compounds derived from its metabolism such as acetic acid, formic acid, propanoic acid or acetaldehyde, exerts a partial effect in MIVOISAP.

Example 8

Influence of Ammonia on Plant Growth and Color

In order to obtain more information about the possibility of microorganisms growing in compound-rich media having amino groups, particularly if they are amino acid-rich media, producing volatiles that negatively affect plant growth and development, volatiles which are not produced when microorganisms are grown in minimal media lacking amino acids, the assay of sections 6.1 and 6.2. of Example 6 were repeated, growing plants in the presence of aqueous solutions of 2 cubic centimeters of ammonia, assaying two different concentrations, each in different boxes: at 2% or 5% (v/v). A control in which the plants grew in the presence of water to which no other compound had been added was also included.

The results obtained are shown in FIG. 29. It is observed that the presence of ammonia in the growth atmosphere results in plant depigmentation and growth inhibition, effects which are more pronounced in the case of plants that were grown in the presence of a higher concentration of ammonia and which are not observed in the absence of this compound (photographs marked with the legend "0%"), as control plants had a green color and a larger size than those grown in the presence of ammonium.

As discussed above, this result constitutes important evidence that microorganisms cultured in amino acid-rich media produce volatiles, such as ammonia, that prohibit growth and negatively affect color; such compounds, however, are not produced when microorganisms are cultured in minimal media lacking amino acids.

Example 9

Growth Pattern of Maize and Pepper Plants Grown in the Presence of Microbial Volatiles To check the effect of microbial volatiles on the growth pattern of maize and pepper plants, maize (*Zea mays*, cv. Hill) and pepper (*Capsicum annuum*, cv. Dulce italiano) plants were cultured simultaneously with a culture of *Alternaria alternata*, starting the culture as described in the "Plants, microbial cultures, growth conditions and sampling" section. In this case, to check if the effects of microbial volatiles continued to be detectable over a prolonged culture time, plants were cultured for 54 days (in the case of maize) and 68 days (in the case of pepper).

During this time, data were collected each week on plants grown in the presence of fungal volatiles, as well as of control plants grown in the absence of the culture of *Alternaria alternata*, controlling the height thereof and stem thickness, as well as of the number of leaves, and, in the case of pepper, even flower buds were counted. Samples of plant leaves were also collected to check chlorophyll content thereof.

FIGS. 30 and 32 show, respectively, photographs obtained of the maize and pepper plants after a different number of days had passed from the start of the culture. It is observed that after the first days of culture, the plants grown together with a culture of *Alternaria alternata*, without there being any contact between them (plant on the right in all the photographs), are larger than the plants grown under control conditions, in the absence of fungal volatiles. The numbers next to each photograph indicate the days elapsed from the start of the culture. The number of leaves is also higher in the plants subjected to the effect of fungal volatiles.

FIGS. 31 and 33 show the graphs corresponding to parameters the evolution of which was recorded to compare plants subjected to the effect of fungal volatiles (+FV) and control plants (−FV): height (in centimeters), number of leaves, chlorophyll (in milligrams per g of fresh weight) and stem thickness (in centimeters) in the case of maize (FIG. 31) and height (in centimeters), chlorophyll (in milligrams per g of fresh weight), stem thickness (in centimeters), number of leaves and number of flower buds in the case of pepper (FIG. 33). The numbers seen on the x-axis correspond to the time elapsed, in days, from the start of the culture when the corresponding value was taken.

It is generally observed that the value of all the parameters controlled is greater in plants subjected to the effect of fungal volatiles with respect to that found in control plants: in the case of the height of maize plants, only the height of the control plants is slightly greater for the measurement taken after 14 days. Except in that case, the height of plants subjected to the effect of fungal volatiles is always clearly greater than the height of control plants, a difference that gradually increases with the increase in the days of culture, particularly in the case of maize plants.

The case of chlorophyll accumulation in maize plants is particularly striking: whereas in control plants the amount of chlorophyll relative to the fresh weight decreases with the days of culture, in plants subjected to the effect of fungal volatiles the decrease is much less pronounced, even an increase in the amount of chlorophyll being obtained after 28 days of culture with respect to the previous measurement, although its decrease pattern subsequently continued. In the case of pepper, the amount seems to drop until day 19, at which time it begins to increase again, reaching the 40-47 values close to those of plants after 12 days of treatment with fungal volatiles.

The case of flower buds in pepper plants should also be mentioned, demonstrating the influence of microbial volatiles on growth and flowering patterns. After 26 days of culture, flower buds can be detected in plants treated with fungal volatiles, which are still undetectable in the case of control plants. Subsequently, the number of flower buds is always greater in plants subjected to the effect of fungal volatiles, reaching mean values close to 9 after 40 days of culture.

The photographs shown in FIG. 34 are particularly striking, where it is shown that the roots of plants subjected to the effect of fungal volatiles present spectacular growth, much greater than that of the roots of control plants.

All this corroborates the fact that the effects of microbial volatiles on growth increase and the change of the growth pattern (increase in the number of leaves, number of flowers, earlier flowering . . . ) occur in different species.

Example 10

Treatment of Plants with Microbial Volatiles Increases Resistance Thereof to Water Stress To investigate if the presence of microbial volatiles in the growth atmosphere may further have an effect on any of the factors influencing plant growth, such as culturing under water stress conditions, the growth of wild-type *Arabidopsis thaliana* plants grown in the presence of fungal volatiles produced by a culture of the *Alternaria alternata* fungus was compared with that of plants grown in the absence of said volatiles, after a culture time in which water starts to be scarce in the medium.

To that end, culture assays with respect to *Arabidopsis thaliana* cv. Columbia plants were performed under conditions similar to those performed in the main patent application, as described above in the "Plants, microbial cultures, growth conditions and sampling" section. A portion of the plants (+FV) were grown in Petri dishes containing solid MS medium with 90 mM sucrose in sterile boxes in which a Petri dish without a lid had been placed with a culture of the *Alternaria alternata* fungus, without there being any physical contact between the plant and fungal culture, but the plants being exposed to an atmosphere in which fungal volatiles produced by said fungus were present. The other portion of the plants were grown under the same conditions, except in that the additional Petri dish contained only sterile culture medium (−FV).

FIG. 35 shows the results obtained upon photographing the plants upon starting the process (day 0) and after 7 days of culture (bottom row), at which time the water of the culture medium has been considerably reduced. It is observed that upon starting the assay (day 0), the size of the plants grown in the absence of fungal volatiles was similar to that of the plants grown in the presence of said volatiles; however, on day 7, the plants that have grown in the absence of microbial volatiles have a much smaller size than the plants grown in the presence of fungal volatiles, this size being even less than the size they had on day 0. The plants grown in the presence of fungal volatiles, in contrast, have a size greater than that size they had on day 0.

These data indicate that treatment with microbial volatiles emitted by organisms grown in minimal media promotes an increase in the resistance to stressful conditions such as water stress in plants.

Example 11

Starch Accumulation Promoted by Microbial Volatiles is Subjected to Photoreceptor-Mediated Control In addition to providing the primary energy source for the development of photosynthesis, light is one of the most important environmental signals that controls many physiological and developmental aspects of plants. Light acts through photoreceptors, regulating various responses such as seed germination, seedling establishment, adjustment of circadian rhythms, flowering time, light-induced starch reserve degradation, carbon partitioning flow, etc. The major families in photoreceptors occurring in plants are the phototropins and cryptochromes (CRY), which absorb blue light, and phytochromes (PHY), which absorb red light or far-red light. Both direct adaptive changes in the expression of genes in response to environmental light signals; for example, the expression of genes encoding enzymes relating to starch and nitrogen metabolism are subjected to phytochrome-mediated photocontrol. Photoreceptors also direct very fast cytoplasmic responses such as apoplastic acidification by means of proton-pumping-ATPase present in the plasma membrane, which is necessary for cellular expansion, and stomatal aperture, chloroplast movement, actin-dependent cytoplasmic flows, gravitropism and hypocotyl elongation, which are not the consequence of changes in gene expression. The perception of red light and far-red light by means of PHY requires the presence of phytochromobilin, which is covalently bound to the apoprotein portion of PHY. In *Arabidopsis*, this chromophore is synthesized by products of HY1 and HY2 genes. Upon receiving red or infrared light, the phytochrome experiences a conformational cis-trans change, resulting in the exchange between the so-called active form (form Pfr, which absorbs in the far-red) and inactive form (Pr, which absorbs in the red zone).

To investigate the possible involvement of light signaling in MIVOISAP, the increase in starch content promoted by fungal volatiles was compared between wild-type plants (WT) and mutants deficient in photoactive PHY and in CRY hy1/cry2, hy1/cry1 and hy1/cry1/cry2. To that end, *Arabidopsis thaliana* plants were used and culture assays were performed with them similar to those performed in the main patent application, as described above in the "Plants, microbial cultures, growth conditions and sampling" section. To that end, *Arabidopsis thaliana* cv. Columbia plants were used as wild-type plants, and plants deficient in photoactive PHY and in CRY hy1/cry2 and hy1/cry1 were used as mutants. They were all grown in the presence of fungal volatiles produced by a culture of *Alternaria alternata* with which they shared a grow box, without there being any physical contact between the plant and fungal culture.

As can be seen in FIG. 36A, the increase in starch content in hy1/cry1/cry2, hy1/cry2 and hy1/cry1 mutants after 16 hours of treatment with fungal volatiles (+FV) was considerably less than in wild-type plants (WT). This data set is a clear indication that MIVOISAP is subjected to photoreceptor-mediated control.

The experiment was repeated again with wild-type plants but cultured for 16 hours with continuous red, far-red or blue light. As can be seen in FIG. 36B, these analyses showed that fungal volatiles (FV) induced an increase in starch content in plants cultured under continuous red light which was comparable to that observed in plants cultured under white light (approximately 25 times more starch in the presence of FV than in the absence of FV), whereas illumination for 16 hours with blue light or far-red light only caused a 3-fold increase with respect to the normal starch content. These data seem to indicate that MIVOISAP is mainly promoted by the active Pfr form.

Example 12

Impact of Enzymes Involved in Starch Degradation in MIVOISAP of *Arabidopsis thaliana*

Of the nine proteins similar to β-amylases encoded in the *Arabidopsis thaliana* genome (BAM1-9), only BAM1-4 are plastidial and have direct access to starch. BAM1 is an enzyme regulated by thioredoxins which degrades starch during the day both in mesophilic and guard cells subjected to thermal shock and osmotic stress. BAM3 is the main determining factor of starch degradation of leaves during the night and also plays an important role in starch degradation during the day in the case of cold shock. BAM4 does not present catalytic activity but has an important BAM1-3 regulating function, modulating starch degradation. Unlike plastidial β-amylases, the precise role of extraplastidial β-amylases and of α-amylase AMY3 in starch metabolism is still unknown. Although some studies have shown that mutants with alterations in BAM5 (which catalyzes 80-90% of total β-amylase activity) accumulate normal starch levels, more recent studies have demonstrated that bam5 mutants lacking the enzyme can show an excess starch phenotype. Furthermore, although evidence has also been provided indicating that AMY3 is not required for transitory starch degradation, other authors have demonstrated that amy3 mutants lacking said enzyme accumulate more starch than wild-type plants.

Isoamylase 3 (ISA3) is a debranching enzyme participating in starch degradation releasing maltodextrins into the stroma, which are then subjected to the action of plastidial β-amylases and plastidial phosphorylase of starch (PHS1). Transcriptome analyses showed that fungal volatiles promote the expression of ISA3 (1.72-fold increase). These analysis also showed a marked increase in the expression of BAM5 after treatment with fungal volatiles (4.81-fold increase), accompanied by an 3.1-fold increase of total β-amylase activity (11.8±2.1 U/g of fresh weight and 37.0±3.2 U/g of fresh weight in the absence and presence of fungal volatiles for 16 hours, respectively). Therefore, the increase in fungal volatile-induced total β-amylase activity can be ascribed to the up-regulation of BAM5.

It was investigated if plastidial enzymes of starch degradation and/or BAM5 were determining factors in MIVOISAP, measuring starch content in leaves of T-DNA, BAM4, BAM5 and AMY3 insertion mutants, cultured for 16 hours under white light. Starch in the T-DNA SEX1 insertion mutant lacking an enzyme which catalyzes starch phosphorylation so that it can be hydrolyzed by β-amylase was also measured (Edner, C, et al. 2007: Plant Physiol. 145, 17-28). bam5 and amy3 leaves not treated with fungal volatiles accumulated starch levels similar to those of wild-type plants, whereas non-treated bam4 and sex1 leaves accumulated more starch than leaves of wild-type plants (FIG. 37A). Unlike amy3 and bam5 leaves, which accumulated starch levels similar to those of wild-type plants after 16 hours of treatment with fungal volatiles (approximately 25 times more starch in the presence than in the absence of fungal volatiles), bam4 and sex1 leaves accumulated 30-35 times more starch in the presence of FVs than leaves of wild-type plants did in the absence of treatment with fungal volatiles.

The overall data indicate that: a) starch biosynthesis and β-amylase-mediated starch degradation occur simultaneously during MIVOISAP, and b) β-amylase-dependent starch degradation pathways are activated with treatment with fungal volatiles. To confirm this hypothesis, the analyses of the measurement of maltose (β-amylase reaction product) in wild-type plants and BAM4 T-DNA insertion mutants showed that while leaves of wild-type plants treated with fungal volatiles accumulated clearly higher levels of maltose than the leaves of wild-type plants not treated with fungal volatiles, the leaves of BAM1 and BAM4 mutants obtained by T-DNA insertion, both treated with fungal volatiles and not treated with them, accumulated a similar maltose content (FIG. 37B).

Example 13

Impact of Redox Enzymes on MIVOISAP in *Arabidopsis*

Regulation of the function of the proteins by means of changes in the redox status plays an important role in many aspects of the plant life, such as growth, development and response to limitations in the environment. Illumination results in very fast PHY-mediated activation of proton-pumping-ATPases of the plasma membrane, which in turn results in changes in membrane potentials, ion flux and internal cellular redox status. In chloroplasts, the activity of a number of enzymes is linked to the redox status of the photosynthetic electron transport chain. Chloroplasts have two important redox systems which independently regulate plastidial metabolism providing reducing equivalents to target enzymes. One is based on thioredoxins (Trxs) and the other pathway is based on a peculiar type of NADPH Trx reductase referred to as NTRC. While the Trx-dependent pathway obtains reducing power from feredoxin (Fdx) reduced by the photosynthetic electron chain and mediated by Fdx-dependent Trx reductase (FTR), NTRC uses NADPH as a source of reducing power, which can be produced in the dark from G6P through the oxidative pentose phosphate pathway (OPPP), or can be obtained under conditions from reduced Fdx by means of Fdx-NADP reductase. Enzymes from the Calvin cycle, ATP synthesis and NADPH exportation from chloroplasts are activated by means of Trx-mediated reduction of cysteine residues, whereas G6P dehydrogenase of chloroplasts is inactivated. Trxs also regulate starch metabolism through the activation of post-translational redox of AGP and enzymes involved in starch degradation, such as SEX1 and BAM1. NTRC plays an important role in providing reducing power to detoxify hydrogen peroxide in the dark and in the regulation of AGP redox status.

One of the most striking alterations in the transcriptomes of *Arabidopsis* leaves treated with fungal volatiles emitted by *Alternaria alternata* involves the activation of proton ATPases of the type located in the plasma membrane, as well as the repression of plastidial FTR and Trxs. The first effect results in changes in membrane potentials, ion flux and internal cellular redox status, which in turn result in rapid acidification of the apoplast, hydrogen peroxide production and activation of genes involved in defense responses. The second effect results in a partial blocking of the main connection between the light absorbed by chlorophylls and metabolic activity in the plastid (Fdx/Trx system), which in turn favors the NTRC pathway as an alternative system for transferring reducing equivalents to target enzymes probably involved in MIVOISAP. To check this hypothesis, starch content in ntrc mutants cultured in the absence or presence of fungal volatiles for 16 hours was measured. It is striking that only a 6-fold increase in starch content was observed in the FV-treated ntrc mutants (FIG. 38), which indicates that NTRC is an important determining factor of MIVOISAP in *Arabidopsis thaliana*.

Example 14

Impact of Starch Synthases on MIVOISAP of *Arabidopsis*

Five different classes of starch synthases (SS) in plants are known: granule-bound starch synthase (GBSS), which is responsible for amylose synthesis, and soluble starch synthases of classes I, II, III and IV (SSI, SSII, SSIII and SSIV, respectively), which are responsible for amylopectin synthesis. It has been demonstrated that the elimination of SSIV results in the accumulation of a single large-sized starch granule in *Arabidopsis* chloroplasts. Furthermore, using different combinations of SS mutations in mutants environments in SSIII and SSIV, it has also been demonstrated that double SSIII/SIV or triple SSI/SSII/SSIII T-DNA insertion mutants of *Arabidopsis* grown autotrophically accumulate null or very reduced levels of starch. These data a) indicate that both SSIII and SSIV play a) key role in starch accumulation, although SSIV is mandatory to produce the regular number of starch granules found in wild-type plants, and b) suggests that SSIV plays a pivotal role in the starch granule initiation process.

Microarray analyses of leaves of *Arabidopsis thaliana* plants treated with fungal volatiles showed no changes in the expression of SSI, SSII, SSIII and SSIV.

It was investigated if SS are involved in MIVOSAP by measuring starch content in leaves of homozygous T-DNA insertion mutants in GBSS, SSI, SSII, SSIII, SSIV, SSI/SSIV, SSII/SSIV SSIII/SSIV SSI/SSII/SSIII and SSI/SSII/SSIV, cultured for 16 hours in the presence or in the absence of fungal volatiles emitted by *A. alternata*. These analyses showed that the fungal volatile-induced increase in starch content in leaves of T-DNA insertion mutants GBSS, SSI and SSII was normal when compared with that of wild-type leaves (20-25 times more starch in the presence than in the absence of fungal volatiles). In contrast, the increase in starch in leaves treated with fungal volatiles of T-DNA insertion mutants SSIII, SSIV, SSI/SSIV, SSII/SSIV, SSI/SSII/SSIII and SSI/SSII/SSIII was considerably less than in leaves of wild-type plants treated with fungal volatiles (FIG. 38).

The changes show that a) changes in the expression of genes encoding SS play a minor role (if any) in MIVOISAP and b) MIVOISAP is clearly determined by SSIII and SSIV. It can be inferred that certain still unidentified post-transcriptional mechanisms of the regulation of SSIII and SSIV must play a major role in MIVOISAP. In this respect, it is significant that SSIII contains a consensus motif of the phosphoserine/threonine 14-3-3 binding proteins participating in regulatory functions of the response to the environment regulated by phosphorylation and that SS activity depends on the redox status.

Example 15

Influence on Protein Accumulation in the Starch Granule

Microscopy analyses described in the main patent application P201000499, performed on *Arabidopsis thaliana* plants which expressed the granule-bound starch synthase (GBSS) of *Arabidopsis* fused with green fluorescent protein (GFP) (Szydlowski et al., 2009: Plant Cell 21, 2443-2457) cultured in the presence and in the absence of FVs (fungal volatiles) emitted by *Alternaria alternata*, demonstrate that the increase in starch content is not due to an increase in the number of granules per plastid but to a spectacular increase in size of the starch granules.

Spanish patent application P201001115 describes and claims a method for the production and purification of recombinant proteins in plants. This method is based on the production of genetically modified plants (or plant cells) expressing granule-bound starch proteins fused with proteins of interest through an amino acid sequence recognized specifically by a protease. Once the starch granules are isolated (which are readily isolable and purifiable), they are treated with the protease such that the protein of interest is released. Works have also been recently published which show that plants expressing starch granule-bound proteins fused with antigens are capable of inducing an immune response in mice that are fed with the starch from those plants.

With this background, the increase in the total amount of protein associated with starch can be an advantage itself, or it can further entail a potential manner of increasing yields and efficiency of methods for purifying recombinant proteins associated with starch granules. It also constitutes a manner of increasing the amount of antigen in plants which act as oral vaccines, such that the immune system response will be stronger when the individual takes starch-vaccine from plants treated with microbial volatiles than when taking starch-vaccine from plants not treated with microbial volatiles.

It was therefore checked if the increase in the size of the starch granules was accompanied by an increase in the total amount of protein associated with the starch, using to that end *Arabidopsis thaliana* plants transformed with granule-bound starch synthase (GBSS) of *Arabidopsis* fused with the green fluorescent protein (GFP) (Szydlowski et al., 2009: Plant Cell 21, 2443-2457) cultured in the presence and in the absence of FVs (fungal volatiles) emitted by *Alternaria alternata*. Plants were cultured for 16 hours under white light, total proteins were extracted from the plants and the presence of GFP associated with GBSS was checked by Western type blot immunoassays.

The results, which are shown in FIG. 39, confirm that there is an increase in the amount of proteins associated with starch granules when plants are cultured in the presence of microbial volatiles: the starch extract from plants treated with fungal volatiles accumulates more GBSS-GFP than the extract from the same amount of plants not treated with fungal volatiles. Thus, the plant culture in the presence of microbial volatiles can serve to increase the production of proteins forming fusion proteins with proteins associated with the starch granule, such as GBSS, increasing the yield obtained per plant.

Example 16

Plasmids Useful for the Preparation of Transgenic Plants with Increased Starch Accumulation Capacity MIVOISAP is transcriptionally regulated. Therefore, as described above, reproduction by means of transgenesis of the MIVOISAP-induced metabolic changes must give way to transgenic plants in which starch accumulation increases with respect to wild-type plants of the same species. It is necessary to have the suitable vectors to produce those plants.

To that end, the Gateway protocol for vector constructs for plant transformation was used (Nakagawa et al., 2007: Journal of Bioscience and Bioengineering 104: 34-41), based on the insertion of double-stranded DNA sequence fragments into specific vector sites, making use of the site-specific properties of bacteriophage lambda, the use of recombinases and in the presence of recognition sequences for same both in the fragment to be inserted and in the vectors in which it is to be inserted. The process requires the presence of DNA recombination sequences of phage lambda (att sites) flanking, on one hand, the fragment to be inserted, and on the other hand, the presence of complementary att sequences in the vector in which said DNA fragment is to be inserted. The process necessarily requires the presence of the recombinase capable of recognizing att sequences of the fragment to be inserted (attB: attB1 and attB2, equivalent to the sites found in nature in the *E. coli* genome) and the corresponding sequences in the vector in which they are to be inserted (attP: attP1 and attP2, respectively, corresponding to the sequences present in the bacteriophage lambda). The recombinase will recognize both pairs of sequences and will produce the insertion of the DNA fragment into the vector, between the attP1 and attP2 sequences; the splicing is done such that they disappear in the attB and attP sequences, attL sequences (attL1 and attL2) being generated in the recombinant vector; this step would be the equivalent to inserting the bacteriophage lambda into the genome of the bacteria. If these sequences are in turn recognized by a second recombinase, a second recombination reaction in the presence of a vector having the complementary pair of att sites recognized by that second recombinase (attR: attR1 and attR2) would allow a second recombination event.

Figure 40B:
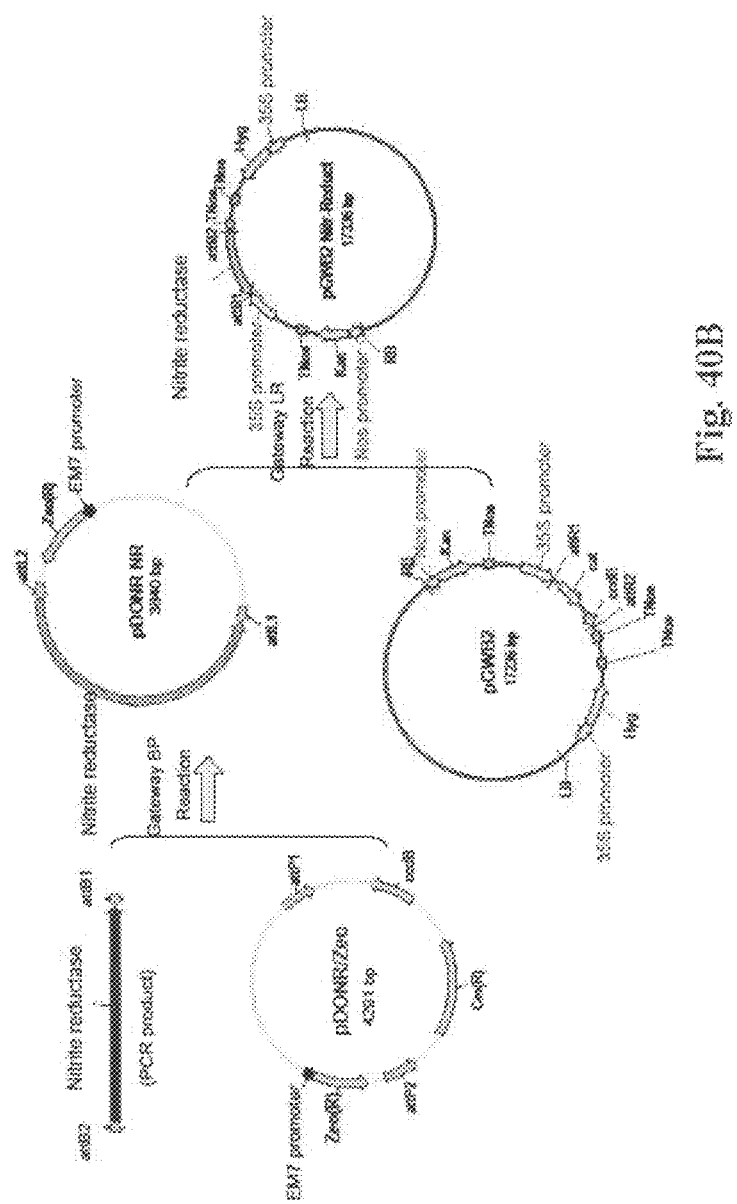
Figure 40C:
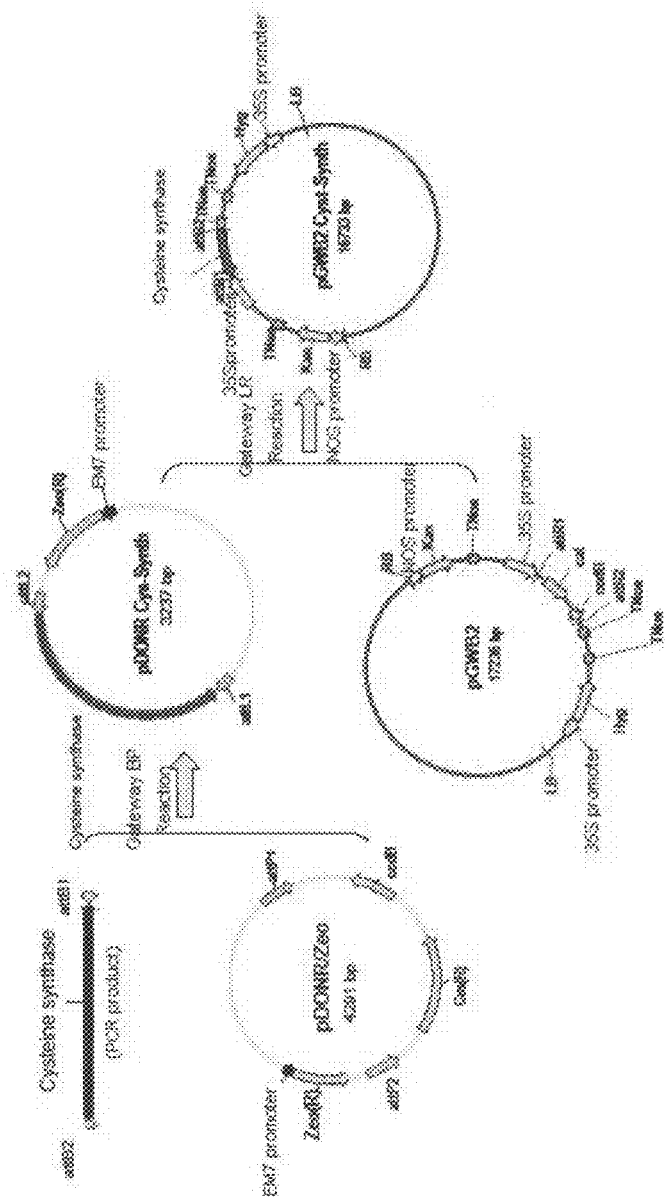
Figure 43:
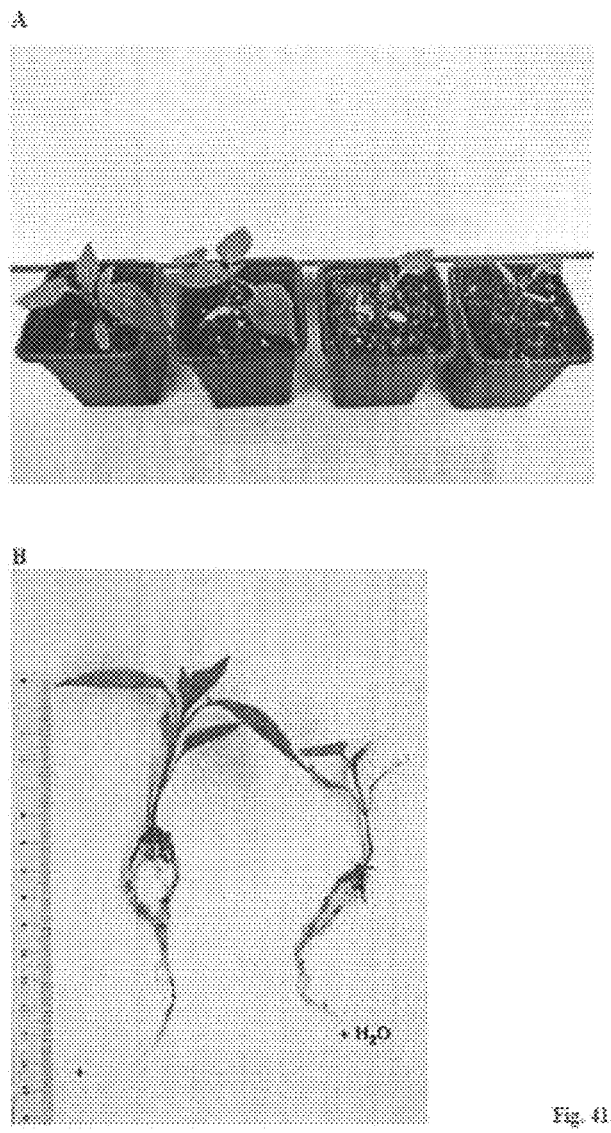

In the present example, Gateway technology of Invitrogen was used following the manufacturer's instructions (Gateway® Technology protocol: http://www.invitrogen.com/site/us/en/home/Products-and-Services/Applications/Cloning/Gateway-Cloning/GatewayC-Misc/Protocols.html#bp). To produce the constructs necessary for expressing nitrite reductase and plastidial cysteine synthase in antisense, commercial vector pDONR/Zeo, of Invitrogen, which has attP1 and attP2 recombination sequences, and PCR products having an attB2 sequence at 5' and an attB1 sequence at 3', as can be observed in FIGS. 40B (antisense nitrite reductase) and 40C (antisense cysteine synthase). In the case of the construct necessary for expressing the protease inhibitor, the PCR product had an attB1 sequence at the 5' end and an attB2 sequence at the 3' end (FIG. 40A). These of PCR products were obtained by performing PCR reactions with attB primers. The attB primers are designed with the following arrangement:

Primer for the insertion of the attB1 sequence:

```
5-GGG-ACA-AGT-TTG-TAC-AAA-AAA-GCA-GGC-TNN-
(sequence specific for the DNA mold to be
amplified)-3'
```

Primer for the insertion of the attB2 sequence:

```
5'-GGGG-AC-CAC-TTT-GTA-CAA-GAA-AGC-TGG-GTN-
(sequence specific for the DNA mold to be
amplified)-3'
```

In both cases, the underlined fragment represents the attB1 and attB2 sequences per se and N represents any nucleotide.

This same strategy was followed for the amplification of encoding DNA fragments corresponding to the genes of the potato plant (*Solanum tuberosum*) of the protease inhibitor (SEQ ID NO:67), antisense nitrite reductase (SEQ ID NO:69) and antisense cysteine synthase (SEQ ID NO:71). The specific primers used in each case were the following:

Protease Inhibitor:

```
proteinase inh attB1 (SEQ ID NO: 73):
5'-GGGGACAAGTTTGTACAAAAAAGCAGGCTTAATGGAGTCAAAGTGT
GCTCACATC-3' proteinase inh attB2 (SEQ ID NO: 74):
5'-GGGGACCACTTTGTACAAGAAAGCTGGGTATTAACCAACCACAGGA
ATCTGTAC-3'
```

Nitrite Reductase:

```
Nitrite reductase attB1 (SEQ ID NO: 75):
5'-GGGGACAAGTTTGTACAAAAAAGCAGGCTTATTAATCTTCTGTTTC
TTCTCTTTCTC-3'
```

```
Nitrite reductase attB2 (SEQ ID NO: 76):
5'-GGGGACCACTTTGTACAAGAAAGCTGGGTAATGGCATCTTTTTCTA
TCAAATTTTTG-3'
```

Cysteine Synthase:

```
pCys synthase attB1 (SEQ ID NO: 77):
5'-GGGGACAAGTTTGTACAAAAAAGCAGGCTTATCACAATTCTGGCTT
CATTTTCTC-3' pCys synthase attB2 (SEQ ID NO: 78):
5'-GGGGACCACTTTGTACAAGAAAGCTGGGTAATGGCATCTTTCATCA
ACAATCC-3
```

The sequence fragments in bold print correspond to the amplified genes, whereas the underlined parts correspond to the attB1 sequences (sequences with an odd order number) or to the attB2 sequences (sequences with an even order number).

The double-stranded sequences depicted by SEQ ID NO:67, SEQ ID NO:69 and SEQ ID NO:71 were thus amplified. The sequences encoding nitrite reductase and cysteine synthase (SEQ ID NO:69 and SEQ ID NO:71, respectively) had an attB2 sequence at their 5' end and an attB1 sequence at their 3' end, whereas the sequence encoding the protease inhibitor had an attB1 sequence at its 5' end and an attB2 sequence at its 3' end. The Gateway insertion protocol for inserting these fragments into plasmids is based on performing two successive recombination reactions; BP reaction (to produce the introduction vector) and LR reaction (resulting in the expression vector) following Invitrogen's manufacturer's instructions). To that end, commercial vector pDON/Zeo (Invitrogen; structure. Page 50 of the Gateway® Technology Protocol) was used in all cases, containing between the attP recombination sites a chloramphenicol resistance gene ($Cm^R$) and the sequence of the ccdB gene. Outside the recombination region it has zeocin resistance gene ($Zeo^R$) under the control of the EM7 promoter which allows the selection of the bacteria transformed with this vector. The incubation of the double-stranded sequences represented by SEQ ID NO:67, SEQ ID NO:69 or SEQ ID NO:71, flanked by the corresponding attB sequences, with said pDON/Zeo vector in the presence of Invitrogen BP Clonase®, following the manufacturer's instructions (page 22 of the of Gateway® Technology Protocol) resulted in a recombination vector in which the desired double-stranded DNA fragment had been inserted between the attP1 and attP2 sequences of the plasmid, generating attL1 and attL2 sequences and making the fragment in which chloramphenicol resistance genes and the ccdB gene were located disappear (plasmids: Prot-Inhb pDONR, NR pDONR and Cys-Synth pDONR, respectively). Each of these plasmids was amplified after its transformation into competent TOP 10 *E. coli* cells, selecting the transformants by using the zeocin resistance conferred by the plasmid.

Once the recombinant plasmid was amplified, it was inserted into plasmid pGWB2 (Nakagawa T, Kurose T, Hino T, Tanaka K, Kawamukai M, Niwa A N D, Toyooka K, Matsuoka K, Jinbo T, Kimura T. 2007 Development of series of gateway binary vectors, pGWBs, for realizing efficient construction of fusion genes for plant transformation. J. Biosci. Bioeng. 104(1): 34-41), containing attR1 and attR2 recombination sequences, which allow insertion therebetween of a fragment flanked by attL1 and attL2 sequences in the presence of the LR Clonase® recombinase (Invitrogen). This vector allows the constitutive expression of encoding sequences by means of the cauliflower mosaic virus (CaMV) 35S promoter. This vector has two transformed plant selection markers: the hygromycin phosphotransferase (Hyg) gene under the control of the CaMV 35S promoter, and a kanamycin (Kan) resistance gene under the control of the Nos promoter. The attR1 and attR2 sequences flank a fragment of the vector in which are the ccdB and cat genes are located, which genes would be replaced by the genes of interest after the recombination reaction performed by the LR recombinase. The recombination reaction results in the insertion of the gene of interest between the attR1 and attR2 sequences, the attB1 and attB2 sequences flanking the ends of the gene of interest being regenerated and the ccdB and cat genes being lost but the final plasmid maintains the kanamycin resistance gene (Kan) and the hygromycin phosphotransferase (Hyg) gene. When *Agrobacterium tumefaciens* transforms a plant cell, it will transfer a DNA fragment of the plasmid pGBW2 to the plant genome comprised between the sequences referred to as LB (left border) and RB (right border), which includes the kanamycin resistance and hygromycin genes and the gene of interest.

These plasmids would be suitable for the generation of transgenic plants expressing at least one nucleotide sequence selected from the gene encoding a protease inhibitor and the antisenses of the genes encoding plastidial nitrite reductase and cysteine synthase, which would allow using said plants to obtain an increase in starch accumulation.

Example 17

Effect of the Supply of Microbial Volatiles in Irrigation Water

To check if the irrigation water may be a valid medium for supplying mixtures of microbial volatiles to the plants, resulting in the desired effects of growth increase and increase in the amount of starch accumulated, an assay was performed with pepper plants.

To obtain the volatiles, the *Alternaria alternata* fungus was cultured in solid MS medium supplemented with 90 mM sucrose. After forming a large mycelium, it was transferred to a liquid MS medium without sucrose where it remained for a couple of days. This medium was filtered and used to irrigate the plant, being referred to as "culture medium".

Pepper plants were cultured in 25 liter plastic boxes. Plants were irrigated every 4 days: control plants were irrigated with water, whereas plants being assayed were irrigated with the liquid medium obtained from the culture of *Alternaria alternata*. Photos of the plants were taken when they were 3 weeks old (21 days) or 45 days old.

The results can be observed in FIG. 41. Panels A and B correspond to 3-week old plants, whereas the plants of Panels C and D are 45 days old. It can be seen that the size differences between plants irrigated with culture medium and with water are very noticeable. Panel C further shows that irrigation with culture medium of *A. alternata* entails the formation of adventitious roots assuring better plant growth. In the last photograph, a plant irrigated with water but cultured for 2 weeks next to a recipient containing filtered "culture medium" of *A. alternata* can be seen. The results obtained with it, which are reproducible, allow concluding that part of the promoter effect of the growth of the "culture medium" of *A. alternata* is due to volatile compounds existing in the mentioned medium. In other words, volatiles promoting plant growth can be provided by irrigating with filtered "culture medium" of *A. alternata.*

Assays to check starch accumulation in these plants were additionally performed. The results are shown in FIG. 42, where it can be seen that both plants irrigated with "culture medium" of *A. alternata* and plants grown in an atmosphere in which the volatiles evaporated from it were present showed a significant increase of accumulated starch with respect to control plants.

These tests demonstrate the validity of providing mixtures of microbial volatiles in irrigation water to cause growth increase and an increase in the starch accumulated in plants.

The invention claimed is:

1. A method for increasing plant growth comprising:
culturing at least one microorganism selected from the group consisting of *Escherichia coli*, *Salmonella enterica*, *Agrobacterium tumefaciens*, *Saccharomyces cerevisiae*, *Alternaria alternata*, *Penicillium aurantogriseum*, and *Penicillium charlessi* in a medium that contains no protein and no amino acids;
contacting a plant with volatile compounds, which are emitted during culturing by said at least one microorganism, without direct contact between the plant and the microorganism;
wherein said plant growth is increased compared to that of an otherwise identical control plant not exposed to said volatile compounds or compared to that of an otherwise identical control plant exposed to volatile compounds produced by said microorganism when grown in a medium containing protein or amino acids.

2. The method of claim 1, wherein said microorganism is not a plant growth promoting rhizobacterium ("PGPR").

3. The method of claim 1, wherein said microorganism is not a rhizobacterium.

4. The method of claim 1, wherein increased plant growth is characterized by an increase in plant length, leaf size, stem thickness, or root size compared to a plant grown by an otherwise identical method which was not grown in the presence of said volatile compounds.

5. The method of claim 1, wherein increased plant growth is characterized by an increase in the numbers of leaves, branches, flower buds, flowers, or seeds compared to a plant grown by an otherwise identical method which was not grown in the presence of said volatile compounds.

6. The method of claim 1, wherein increased plant growth is characterized by an increase in chlorophyll production compared to a plant grown by an otherwise identical method which was not grown in the presence of said volatile compounds.

7. The method of claim 1, wherein increased plant growth is characterized by an increase in starch accumulation compared to a plant grown by an otherwise identical method which was not grown in the presence of said volatile compounds.

8. The method of claim 1, wherein increased plant growth is characterized by an increase in resistance to water stress compared to a plant grown by an otherwise identical method which was not grown in the presence of said volatile compounds.

9. The method of claim 1, wherein said plant is a monocotyledon.

10. The method of claim 1, wherein said plant is maize.

11. The method of claim 1, wherein said plant is barley.

12. The method of claim 1, wherein said plant is a dicotyledon.

13. The method of claim 1, wherein said plant is *Arabidopsis*.

14. The method of claim 1, wherein said plant is a pepper.

15. The method of claim 1, wherein said plant is a potato.

16. The method of claim 1, wherein said plant is tobacco.

17. The method of claim 1, wherein said microorganism is *Salmonella enterica*.

18. The method of claim 1, wherein said microorganism is *Escherichia coli*.

19. The method of claim 1, wherein said microorganism is *Agrobacterium tumefaciens*.

20. The method of claim 1, wherein said microorganism is *Alternaria alternata*.

21. The method of claim 1, wherein said volatile compounds are produced by a microorganism grown in a medium that contains no protein and no amino acids, which is supplemented with a carbon source that is an organic compound.

22. The method of claim 1, wherein the plant is a maize plant, a tobacco plant, or a plant from the *Arabidopsis thaliana* species; and wherein said volatile compounds are produced by a microorganism grown in a minimal medium supplemented with an organic carbon source.

23. The method of claim 1, wherein said plant growth occurs in an atmosphere containing volatile compounds emitted by said microorganism.

24. The method of claim 1, wherein said plant growth occurs in an atmosphere containing volatile compounds emitted by said microorganism from a solution containing the volatile compounds.

25. The method of claim 1, wherein the volatile compounds are contained in a filtered culture medium used to culture said microorganism.

26. The method of claim 1, wherein the volatile compounds are contained in irrigation water for the plant.

27. The method of claim 1, wherein the volatile compounds are insufflated to the culture atmosphere.

28. The method of claim 1, wherein the plant is cultured in a greenhouse.

29. The method of claim 1, wherein the volatile compounds are administered to a culture atmosphere of the plant by fumigating or spraying.

30. The method of claim 1, wherein the volatile compounds are administered to a culture atmosphere of the plant along with a fertilizer, a pesticide, or a mixture thereof.

31. The method of claim 1, wherein said volatile compounds do not contain ammonia.

32. A method of claim 1, wherein said volatile compounds are produced by *Saccharomyces cerevisiae*.

33. A method of claim 1, wherein said volatile compounds are produced by *Penicillium aurantogriseum*.

34. The method of claim 1, wherein said volatile compounds are produced by *Penicillium charlessi*.

35. The method of claim 1, further comprising not contacting the plant with a non-volatile component of said microorganism.

36. The method of claim 1, wherein said medium contains no other component that produces an amount of volatile ammonium that inhibits plant growth when metabolized by said microorganisms.

37. A method for increasing growth of a plant consisting essentially of:
   culturing at least one microorganism selected from the group consisting of *Escherichia coli*, *Salmonella enterica*, and *Agrobacterium tumefaciens* in a medium that contains no protein and no amino acids;
   contacting a plant with volatile compounds, which are emitted during culturing by said at least one microorganism, without direct contact between the plant and the microorganism;
   wherein said plant growth is increased compared to that of an otherwise identical control plant not exposed to said volatile compounds or compared to that of an otherwise identical control plant exposed to volatile compounds produced by said microorganism when grown in a medium containing protein or amino acids.

38. The method of claim 37, further comprising not contacting the plant with a non-volatile component of said microorganism.

39. The method of claim 37, wherein said medium contains no other component that produces an amount of volatile ammonium that inhibits plant growth when metabolized by said microorganisms.

40. A method for increasing plant growth consisting essentially of:
   culturing at least one microorganism selected from the group consisting of *Saccharomyces cerevisiae*, *Alternaria alternata*, *Penicillium aurantogriseum*, and *Penicillium charlessi* in a medium that contains no protein and no amino acids;
   contacting a plant with volatile compounds, which are emitted during culturing by said at least one microorganism, without direct contact between the plant and the microorganism;
   wherein said plant growth is increased compared to that of an otherwise identical control plant not exposed to said volatile compounds or compared to that of an otherwise identical control plant exposed to volatile compounds produced by said microorganism when grown in a medium containing protein or amino acids.

41. The method of claim 40, further comprising not contacting the plant with a non-volatile component of said microorganism.

42. The method of claim 40, wherein said medium contains no other component that produces an amount of volatile ammonium that inhibits plant growth when metabolized by said microorganisms.

* * * * *